(12) United States Patent
Panda

(10) Patent No.: US 10,660,967 B2
(45) Date of Patent: May 26, 2020

(54) CURCUMIN CONJUGATES AND METHODS OF USE THEREOF

(71) Applicant: Augusta University Research Institute, Inc., Augusta, GA (US)

(72) Inventor: Siva Panda, Augusta, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

(21) Appl. No.: 15/790,498

(22) Filed: Oct. 23, 2017

(65) Prior Publication Data

US 2018/0110861 A1    Apr. 26, 2018

Related U.S. Application Data

(60) Provisional application No. 62/411,425, filed on Oct. 21, 2016.

(51) Int. Cl.
*C07C 69/96* (2006.01)
*C07C 229/08* (2006.01)
(Continued)

(52) U.S. Cl.
CPC .......... *A61K 47/542* (2017.08); *A61K 9/0053* (2013.01); *A61K 47/545* (2017.08); *C07C 69/96* (2013.01); *C07C 229/08* (2013.01); *C07C 229/18* (2013.01); *C07C 229/36* (2013.01); *C07C 233/25* (2013.01); *C07C 233/47* (2013.01); *C07C 233/51* (2013.01); *C07C 237/06* (2013.01); *C07C 243/14* (2013.01); *C07C 271/22* (2013.01); *C07C 323/52* (2013.01); *C07C 323/58* (2013.01); *C07C 323/59* (2013.01); *C07D 209/20* (2013.01);
(Continued)

(58) Field of Classification Search
CPC ..... C07C 69/96; C07C 229/08; C07C 229/18; C07C 229/36; C07C 233/25; C07C 233/47; C07C 233/51
See application file for complete search history.

(56) References Cited

U.S. PATENT DOCUMENTS 5,948,433 A    9/1999    Burton
5,985,311 A    11/1999   Cordes
(Continued)

FOREIGN PATENT DOCUMENTS

WO    2015/120287 A2    8/2015

OTHER PUBLICATIONS

Mujtaba et al., International Journal of Molecular Medicine 29: 102-106, 2012.*
(Continued)

*Primary Examiner* — Rebecca L Anderson
(74) *Attorney, Agent, or Firm* — Smith, Gambrell & Russell, LLP

(57) ABSTRACT

Curcumin-based conjugates and methods of use thereof are provided. Pharmaceutical compositions including an effective amount of one or more curcumin conjugates are also provided. In particular embodiments, the compositions are formulated for oral delivery. The conjugates and pharmaceutical compositions thereof can be administered to a subject in need thereof to treat a host of diseases and disorders including but not limited to, cancer, inflammation, and microbial growth.

12 Claims, 4 Drawing Sheets

(51) Int. Cl.
| | |
|---|---|
| C07C 229/18 | (2006.01) |
| C07C 229/36 | (2006.01) |
| C07C 233/25 | (2006.01) |
| C07C 233/47 | (2006.01) |
| C07C 233/51 | (2006.01) |
| A61K 47/54 | (2017.01) |
| A61K 9/00 | (2006.01) |
| C07D 209/20 | (2006.01) |
| C07C 323/58 | (2006.01) |
| C07C 323/59 | (2006.01) |
| C07C 323/52 | (2006.01) |
| C07C 237/06 | (2006.01) |
| C07C 243/14 | (2006.01) |
| C07D 209/28 | (2006.01) |
| C07C 271/22 | (2006.01) |

(52) U.S. Cl.
CPC ........ *C07D 209/28* (2013.01); *C07C 2603/18* (2017.05)

(56) References Cited

U.S. PATENT DOCUMENTS

| | | |
|---|---|---|
| 6,461,644 B1 | 10/2002 | Jackson |
| 6,676,961 B1 | 1/2004 | Lichter |
| 2001/0051184 A1 | 12/2001 | Heng |
| 2006/0276536 A1 | 12/2006 | Vander Jagt |
| 2011/0183945 A1 | 7/2011 | Ku |
| 2011/0311444 A1 | 12/2011 | Tooyama |
| 2012/0316203 A1 | 12/2012 | Kuppusamy |
| 2013/0224229 A1 | 8/2013 | Banerjee |
| 2013/0338233 A1 | 12/2013 | Cegelski |
| 2015/0342904 A1 | 12/2015 | Rose |
| 2016/0213626 A1 | 7/2016 | Cegelski |

OTHER PUBLICATIONS

Mishra et al., Bioorganic & Medicinal Chemistry 13 (2005) 1477-1486.*
Cancer and Metastasis Reviews (1998), 17(1), 91-106.*
Science (1999), vol. 286, 531-537.*
Barsoum, Flora, F., et al., "Novel bis(1-acyl-2-pyrazolines) of Potential Anti-Inflammatory and Molluscicidal Properties", Bioorg. Med. Chem, 14: 3929-3937 (2006).
Barsoum, Flora F., et al., "Facile Synthesis of bis(4,5-dihydro-1H-pyrazole-1-carboxamides) and their Thio-Analogues of Potential PGE2 Inhibitory Properties", Eur. J. Med. Chem, 44: 2172-2177 (2009).
Fox, Lizelle T., et al., "Transdermal Drug Delivery Enhancement by Compounds of Natural Origin", Molecules, 16:10507-10540 (2011).
Girgis, Adel S., et al., "Facile Synthesis of Non-Steroidal Anti-Inflammatory Active Bisbenzamide-Containing Compounds", Bioorg. Med. Chem, 14: 8527-8532 (2006).
Girgis, Adel S., "Facile Synthesis of Dithiatetraaza-Macrocycles of Potential Anti-Inflammatory Activity", Eur. J. Med. Chem, 43: 2116-2121 (2008).
Girgis, Adel S., "Regioselective Synthesis of Dispiro[1H-indene-2,3'-pyrrolidine-2',3"-[3H]indole]-1,2" (1"H)-Diones of Potential Anti-Tumor Properties", Eur. J. Med. Chem, 44: 91-100 (2009).
Girgis, Adel S., "Regioselective Synthesis and Stereochemical Structure of Anti-Tumor Active Dispiro[3H-indole-3,2'-pyrrolidine-3',3"-piperidine]-2(1H),4"-Diones", Eur. J. Med. Chem, 44: 1257-1264 (2009).
Girgis, Adel S., et al., "Synthesis of [1,2,4]Triazolo[1,5-α]Pyridines of Potential PGE2 Inhibitory Properties", Eur. J. Med. Chem, 44: 1972-1977 (2009).
Girgis, Adel S., et al., "Computer-Assisted Rational Design, Synthesis, and Bioassay of Non-Steroidal Anti-Inflammatory Agents", Eur. J. Med. Chem, 50: 1-8 (2012).
Goel, Ajay, et al., "Curcumin as "Curecumin": From Kitchen to Clinic", Biochemical Pharmacology, 75(4):787-809 (2008).
Inayat, Bashir P., et al., "Chemical Penetration Enhancers for Transdermal Drug Delivery Systems", Tropical Journal of Pharmaceutical Research, 8(2):173-179 (2009).
Isidro-Llobet, Albert, et al., "Amino Acid-Protecting Groups", Chem. Rev., 109 (6):2455-2504 (2009).
Naumov, Roman N., et al., "Synthesis and QSAR Study of Novel Anti-inflammatory Active Mesalazine-Metronidazole Conjugates", Bioorg. Med. Chem. Lett., 25: 2314-2320 (2015).
Panda, Siva S., et al., "Aminoacyl Benzotriazolides: Versatile Reagents for the Preparation of Peptides and Their Mimetics and Conjugates", Aldrichimica Acta, 46: 43-55 (2013).
Panda, Siva S., et al., "Novel Antibacterial Active Quinolone-Fluoroquinolone Conjugates and 2D-QSAR Studies", Bioorg. Med. Chem. Lett., 25: 3816-3821 (2015).
Perrone, Donatella, et al., "Biological and Therapeutic Activities, and Anticancer Properties of Curcumin (Review)", Exp. Ther. Med., 10: 1615-1823 (2015).
Salem, Melessa, et al., "Curcumin, A Promising Anti-Cancer Therapeutic: A Review of its Chemical Properties, Bioactivity and Approaches to Cancer Cell Delivery", RSC Adv., 4: 10815-10829 (2014).
Tiwari, Dipak Kumar, et al., "Divergent Total Synthesis of 1,6,8a-tri-epi-castanospermine and 1-deoxy-6,8a-di-epi-castanospermine from Substituted Azetidin-2-One (β-lactam), Involving a Cascade Sequence of Reactions as a Key Step", Org. Biomol. Chem, 12: 7238-7249 (2014).

* cited by examiner

CURCUMIN CONJUGATES AND METHODS OF USE THEREOF

CROSS REFERENCE TO RELATED APPLICATION

This application claims benefit of and priority to U.S. Provisional Patent Application 62/411,425 filed on Oct. 21, 2016, and is incorporated by reference in its entirety.

FIELD OF THE INVENTION

This invention is generally in the field of curcumin-based drugs and methods of use thereof, particularly for treatment of inflammation.

BACKGROUND OF THE INVENTION

Curcumin, a component of turmeric (*Curcuma longa*), is used as a remedy to treat a wide variety of ailments through a number of separate pharmacological pathways. Among the range of diseases curcumin is used to treat, it is more commonly used to treat inflammation without chronic side effects including gastrointestinal ulceration, kidney failure, and liver failure, and a considerable amount of research is currently being conducted to determine its anticancer, anti-inflammatory and antimicrobial capacity. Similarly, dichloroacetic acid (DCA), a synthetic antitumor drug, causes cancer cell apoptosis by correcting metabolic oddities.

Current anti-inflammatory medications and cancer treatments, although effective, can produce serious side effects, which in some cases can be irreversible. For example, although common anti-inflammatory drugs such as analgesics and non-steroidal anti-inflammatory drugs (NSAIDs) such as ibuprofen, mefenamic acid, diclofenac, naproxen, and indomethacin, have been proven to manage pain and swelling, they are relatively inefficient and can produce significant side effects with prolonged use.

Although curcumin and DCA exhibit qualities that show promise for effectively treating certain life-threatening diseases, they do come with some drawbacks. Curcumin, while non-toxic, has low bioavailability and DCA can cause neurotoxicity in high concentrations. Eliminating these complications are important in developing possible curcumin and DCA drug treatments.

Therefore, there remains a need for improved compositions for treatment of inflammation.

It is an object of the invention to provide compositions with higher potency, greater bioavailability, fewer or decreased side effects, or a combination thereof and methods of using them for treating a range of diseases and disorders.

SUMMARY OF THE INVENTION

Curcumin-based conjugates and methods of use thereof are provided. One embodiment provides curcumin conjugates having the general formula

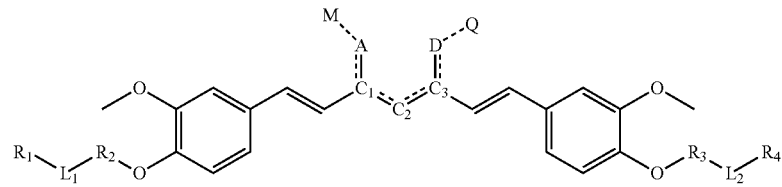

Formula I wherein the dotted lines between A and $C_1$, $C_1$ and $C_2$, $C_2$ and $C_3$, and $C_3$ and D indicate that a single or double bond may be present, as valence permits, wherein the dotted lines A and M, and D and Q indicate that a single bond or no bond may be present, as valence permit, wherein $C_1$, $C_2$, and $C_3$ are carbon atoms, wherein A and D are oxygen atoms, wherein M and Q are independently absent, or hydrogen, as valence permits, wherein $R_2$ and $R_3$ can be independently absent, one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms, inclusive, preferably between $C_1$ and $C_{20}$ carbon atoms, inclusive, more preferably between $C_1$ and $C_{10}$ carbon atoms, with the proviso that at least one of $R_2$ or $R_3$ is present, wherein $R_1$ and $R_4$ can be independently absent, one or more amino acids or salts thereof, nucleic acids, lipids, polysaccharides, polymers, substituted or unsubstituted alkyl groups, alkenyl groups, alkynyl groups, aryl groups, heteroaryl groups, organic protecting groups, small molecules, or other organic groups containing between $C_1$ and $C_{30}$ carbon atoms, inclusive, preferably between $C_1$ and $C_{20}$ carbon atoms, inclusive, more preferably between $C_1$ and $C_{10}$ carbon atoms, and wherein $L_1$ and $L_2$ can be independently absent, substituted or unsubstituted alkyl groups, alkenyl groups, alkynyl groups, aryl groups, heteroaryl groups, or other organic groups containing between $C_1$ and $C_{20}$ carbon atoms, inclusive, preferably between $C_1$ and $C_{10}$ carbon atoms, inclusive, or pharmaceutically acceptable salt(s), polymorph(s), solvent(s), hydrate(s), crystal forms, and/or enantiomer(s) thereof.

One embodiment provides an optically pure composition containing one or more of the disclosed curcumin compositions. The optical purity is not particularly limited, but is usually about 90%, 95%, or 99% optically pure. Another embodiment provides a composition containing one or more of the disclosed curcumin compositions that is at least 99% optically pure.

In some aspects, $R_1$ and $R_4$ can be independently organic protecting groups such as carboxybenzyl (Cbz), fluorenylmethyloxycarbonyl (FMOC), tert-butyloxycarbonyl (BOC), or a small molecule such as dichloroacetic acid.

In some aspects, the curcumin can be in the keto form, i.e., M and Q are absent, the bond between A and $C_1$, and D and $C_3$ are double bonds, and the bonds between $C_1$ and $C_2$, and $C_2$ and $C_3$ are single bonds.

In some aspects, the curcumin can be in the enol form, i.e., (i) the bond between $C_1$ and A is a double bond, M is absent, the bond between $C_1$ and $C_2$ is a single bond, the bond between $C_2$ and $C_3$ is a double bond, the bond between $C_3$ and D is a single bond, and Q is hydrogen, or (ii) the bond between $C_3$ and D is a double bond, Q is absent, the bond between $C_2$ and $C_3$ is a single bond, the bond between $C_1$ and $C_2$ is a double bond, the bond between $C_1$ and A is a single bond, and M is hydrogen.

In other aspects, $R_2$ and $R_3$ are each independently an amino acid and $R_1$ and $R_4$ are each independently an organic protecting group or a small molecule.

Pharmaceutical compositions including an effective amount of one or more curcumin conjugates, for example, a mixture of two or more different curcumin conjugates, are also provided. The pharmaceutical compositions may include a pharmaceutically acceptable excipient. In particular embodiments, the compositions are formulated for oral delivery.

One embodiment provides a pharmaceutical composition containing Cbz-DL-Ala-Cur, Cbz-Met-Cur, Fmoc-Gly-Cur, Fmoc-Met-Cur, Z-D-Ala-Cur, Z-D-Met-Cur, Boc-L-Met-Cur, Boc-D-Met-Cur, HCl-Gly-Cur, HCl-L-Phe-Cur, HCl-DL-Ala-Cur, HCl-D-Ala-Cur, HCl-β-Ala-Cur, HCl-L-Met-Cur, HCl-D-Met-Cur, HCl-L-Ile-Cur, or a combination thereof or pharmaceutically acceptable salt(s), polymorph(s), solvent(s), hydrate(s), crystal forms, and/or enantiomer(s) thereof.

The conjugates and pharmaceutical compositions thereof can be administered to a subject in need thereof to treat a host of diseases and disorders including, but not limited to, wounds, diabetes, neurodegenerative diseases, cardiovascular diseases, pulmonary disease, arthritis, cancer (for example, melanoma, colon cancer, lung cancer, breast cancer, prostate cancer, cervical cancer, liver cancer, testicular cancer, brain cancer, pancreatic cancer, or renal cancer), inflammation (for example, an inflammatory disorder), autoimmune diseases, and microbial growth (for example, a bacterial or fungal infection).

DETAILED DESCRIPTION OF THE INVENTION

I. Definitions

Figure 1:
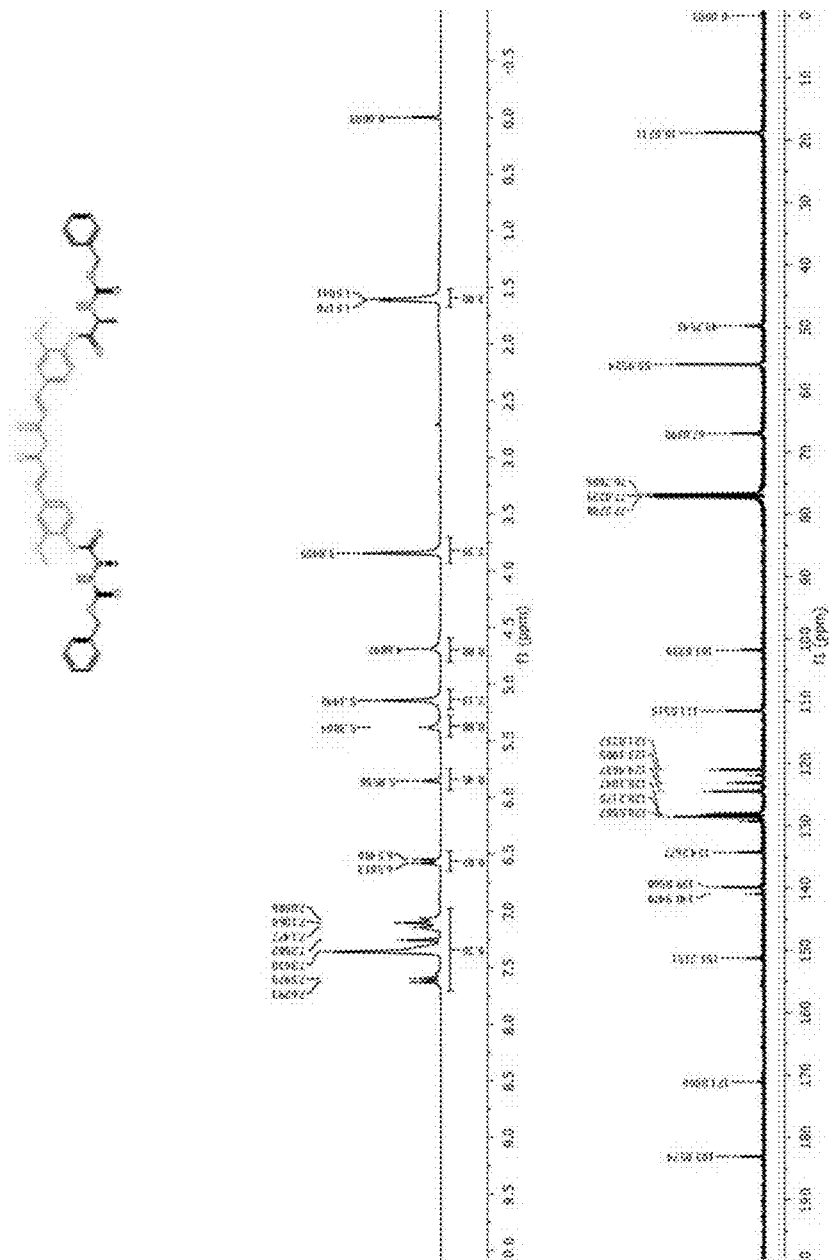
FIG. 1 is an exemplary proton and carbon nuclear magnetic resonance spectrum for a Cbz-Gly-Cur conjugate.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the term "pharmaceutically acceptable salts" includes acid addition salts or addition salts of free bases. "Pharmaceutically acceptable salts" of the disclosed compounds also include all the possible isomers and their mixtures, and any pharmaceutically acceptable metabolite, bioprecursor and/or pro-drug.

As used herein, the term "pro-drug" means a compound which has a structural formula different from a reference compound, and yet is directly or indirectly converted in vivo into the reference compound, upon administration to a subject, such as a mammal, particularly a human being.

The term, "alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, cycloalkynyl groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone, preferably 20 or fewer, and more preferably 10 or fewer.

The term, "alkyl," also includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CONR$_2$, wherein R is hydrogen, alkyl, or aryl; azide, aralkyl, alkoxyl, imino, phosphonate, phosphinate, silyl, ether, sulfonyl, sulfonamido, heterocyclic, aromatic or heteroaromatic moieties, —CF$_3$; —CN; —NCOCOCH$_2$CH$_2$; —NCOCOCHCH; —NCS; and combinations thereof.

The terms "alkenyl" and "alkynyl", as used herein, refer to unsaturated aliphatic groups analogous in length and possible substitution to the alkyls described above, but that contain at least one double or triple bond respectively.

The term "aryl" refers to a mono- or multi-cyclic aromatic radical having in the range of 6 up to 30 carbon atoms such as phenyl, naphthyl, tetrahydronapthyl, indanyl, and biphenyl.

The term, "heteroaryl," as used herein, refers to straight or branched chain, or cyclic carbon-containing radicals, or combinations thereof, having 3 to 30 carbon atoms where one or more of the carbon atoms are replaced by heteroatoms. Suitable heteroatoms include, but are not limited to, O, N, Si, P and S, where the nitrogen, phosphorous and sulfur atoms are optionally oxidized, and the nitrogen heteroatom is optionally quaternized. One of the rings may also be aromatic. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

The term "racemic" as used herein refers to a mixture of the (+) and (−) enantiomers of a compound wherein the (+) and (−) enantiomers are present in approximately a 1:1 ratio.

The terms "substantially optically pure," "optically pure," and "optically pure enantiomers," as used herein, mean that the composition contains greater than about 90% of a single stereoisomer by weight, preferably greater than about 95% of the desired enantiomer by weight, and more preferably greater than about 99% of the desired enantiomer by weight, based upon the total weight.

II. Compositions

A. Curcumin Conjugates

1. Structure of the Conjugates

Curcumin conjugates are provided. One embodiment provides curcumin conjugates having the following general formula:

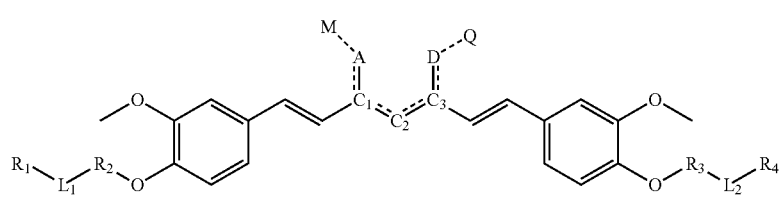

Formula I wherein the dotted lines between A and $C_1$, $C_1$ and $C_2$, $C_2$ and $C_3$, and $C_3$ and D indicate that a single or double bond may be present, as valence permits, wherein the dotted lines A and M, and D and Q indicate that a single bond or no bond may be present, as valence permit, wherein $C_1$, $C_2$, and $C_3$ are carbon atoms, wherein A and D are oxygen atoms, wherein M and Q are independently absent, or hydrogen, as valence permits, wherein $R_2$ and $R_3$ can be independently absent, one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{30}$ carbon atoms, inclusive, preferably between $C_1$ and $C_{20}$ carbon atoms, inclusive, more preferably between $C_1$ and $C_{10}$ carbon atoms, with the proviso that at least one of $R_2$ or $R_3$ is present, wherein $R_1$ and $R_4$ can be independently absent, one or more amino acids or salts thereof, nucleic acids, lipids, polysaccharides, polymers, substituted or unsubstituted alkyl groups, alkenyl groups, alkynyl groups, aryl groups, heteroaryl groups, organic protecting groups, small molecules, or other organic groups containing between $C_1$ and $C_{30}$ carbon atoms, inclusive, preferably between $C_1$ and $C_{20}$ carbon atoms, inclusive, more preferably between $C_1$ and $C_{10}$ carbon atoms, and wherein $L_1$ and $L_2$ can be independently absent, substituted or unsubstituted alkyl groups, alkenyl groups, alkynyl groups, aryl groups, heteroaryl groups, or other organic groups containing between $C_1$ and $C_{20}$ carbon atoms, inclusive, preferably between $C_1$ and $C_{10}$ carbon atoms, inclusive, or pharmaceutically acceptable salt(s), polymorph(s), solvent(s), hydrate(s), crystal forms, and/or enantiomer(s) thereof.

One embodiment provides an optically pure composition containing one or more of the disclosed curcumin compositions. The optical purity is not particularly limited, but is usually about 90%, 95%, or 99% optically pure. Another embodiment provides a composition containing one or more of the disclosed curcumin compositions that is at least 99% optically pure.

In some aspects, $R_1$ and $R_4$ can be independently organic protecting groups such as carboxybenzyl (Cbz), fluorenylmethyloxycarbonyl (FMOC), tert-butyloxycarbonyl (BOC), or a small organic molecule such as dichloroacetic acid.

The polymer can be, for example, a biodegradable polymer such as those known in the art. The polymer can be a hydrophobic polymer such as poly(ethylene glycol) (PEG), wherein the molecular weight is determined by the number of ethylene glycol units. For example, in some embodiments the PEG is between about 500 Da and 20,000 Da.

In some aspects, the curcumin can be in the keto form, i.e., M and Q are absent, the bond between A and $C_1$ and D and $C_3$ are double bonds, and the bonds between $C_1$ and $C_2$ and $C_2$ and $C_3$ are single bonds.

In some aspects, the curcumin can be in the enol form, i.e., (i) the bond between $C_1$ and A is a double bond, M is absent, the bond between $C_1$ and $C_2$ is a single bond, the bond between $C_2$ and $C_3$ is a double bond, the bond between $C_3$ and D is a single bond, and Q is hydrogen, or (ii) the bond between $C_3$ and D is a double bond, Q is absent, the bond between $C_2$ and $C_3$ is a single bond, the bond between $C_1$ and $C_2$ is a double bond, the bond between $C_1$ and A is a single bond, and M is hydrogen.

In some embodiments, the conjugates have one or more amino acids conjugated directly or indirectly thereto. The two or more amino acids can be the same or different amino acids. Thus, the curcumin conjugates disclosed herein can include the formula: AA1-C or C-AA1 or AA1-C-AA1 or AA2-C-AM or AA1-C-AA2, wherein "AA1" and "AA2" represent different amino acids, and "C" represents curcumin. In some embodiments, there is a linker or another molecule or moiety between curcumin and one or both amino acids. In a particularly preferred embodiment, the curcumin conjugate has the structure AA1-C-AA1.

As discussed in more detail below, one or both amino acids are typically conjugated to the curcumin or a linker linking it to curcumin by its C-terminal end. In other embodiments, one or both amino acids are conjugated to curcumin or a linker linking it to curcumin by its N-terminal end, its side group, or a combination thereof. In some embodiments, the end of the amino acid that is not conjugated to curcumin is free. In other embodiments, the end of the amino acid that is not conjugated to curcumin is conjugated to another moiety.

a. Curcumin

One embodiment provides (1E,6E)-1,7-Bis(4-hydroxy-3-methoxyphenyl)hepta-1,6-diene-3,5-dione having the structure

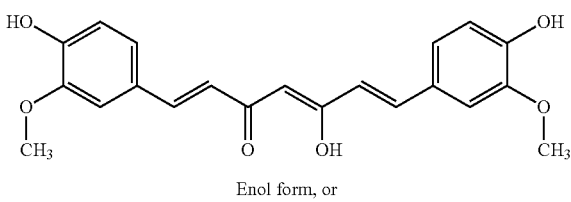

Enol form, or

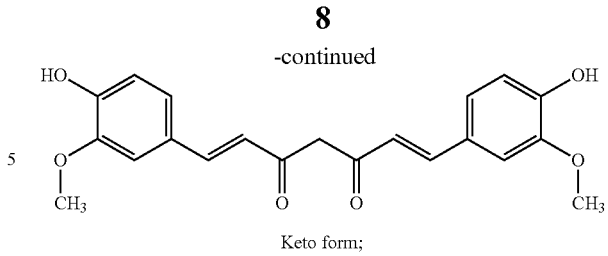

Keto form;

or a variant, derivative, derivative, mimetic, prodrug, or mixtures thereof, or pharmaceutically acceptable salts thereof. The term "derivative" or "derivatized" as used herein includes one or more chemical modifications of (1E,6E)-1,7-Bis(4-hydroxy-3-methoxyphenyl)hepta-1,6-diene-3,5-dione. The term curcumin derivative means natural and synthetic curcumin derivatives. Examples include naturally occurring curcuminoids. These are plant secondary metabolites that occur in the rootstocks of different curcuma plants such as e.g. turmeric [curcuma Tonga]. The term curcuminoids covers the three substances curcumin, demethoxycurcumin and bisdemethoxycurcumin. From a chemical point of view, curcuminoids are conjugated diarylheptanoids, i.e., polyphenols in the broader sense. Curcumin derivatives are discussed in, for example, U.S. Published Application Nos. 2016/0213626, 2015/0342904, 2013/0338233, 2013/0224229, 2012/0316203, 2011/0311444, 2011/0183945, 2006/0276536, and 2001/0051184.

The disclosed compounds include compounds that are chemically modified to increase the resistance of the compound to enzymatic degradation, increase the half-life of the compound in vivo, reduce dosing frequency of the compound, decrease immunogenicity of the compound, increase the physical and/or thermal stability of the compound, increase the solubility of compound, increase the liquid stability of compound and/or reduce the aggregation of compound, and increase the purity of the active pharmaceutical ingredient in the final drug product. The addition of a soluble polymer or carbohydrate to compound may affect all of these pharmacokinetic parameters. The compound can also be one that has been chemically modified. Other forms of curcumin such as pharmaceutically acceptable salt(s), polymorph(s), solvent(s), hydrate(s), crystal forms, and/or enantiomer(s) may are also provided for use in the disclosed compositions and methods.

b. Amino Acids

As discussed above, some of the curcumin conjugates include one or more amino acids. The amino acid(s) can be a standard or non-standard amino acid. "Standard amino acid" or "canonical amino acid" typically refers to the twenty amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Non-standard amino acid (nsAA)" refers to any and all amino acids that are not a standard amino acid. nsAA can be created by enzymes through posttranslational modifications; or those that are not found in nature and are entirely synthetic (e.g., synthetic amino acids (sAA)). In both classes, the nsAAs can be made synthetically. For example, in some embodiments, a tyrosine residue is substituted for a synthetic tyrosine derivative. WO 2015/120287 provides a non-exhaustive list of exemplary non-standard and synthetic amino acids that are known in the art (see, e.g., Table 11 of WO 2015/120287).

The amino acid(s) can be "D" amino acid(s), "L" amino acid(s), or a combination thereof. In some embodiments, the composition includes a mixture of curcumin conjugates. In some embodiments the mixture of curcumin conjugates includes one or more of the conjugates include one or more D amino acids and one or more of the conjugates include one or more L amino acids. In some embodiments, a curcumin conjugate includes at least one D amino acid and one L amino acid. The D and L amino acids can have the same or different side chains.

In some embodiments, the curcumin conjugates may include a salt form of the amino acid. That is, the one or more amino acids conjugated directly or indirectly to the disclosed curcumin conjugates may include a salt form of the amino acid. For example, the curcumin conjugates may include hydrochloride salt forms of the amino acid. In another embodiment, the curcumin conjugates may include acetate salt forms of the amino acid.

c. Additional Moieties and Linkers

In some embodiments, there is a linker or another molecule or moiety between curcumin and one or both amino acids; a linker or another molecule or moiety attached to the end of the amino acid that is not conjugated or linked to curcumin; or a combination thereof. Exemplary moieties include, but are not limited to nucleic acids and polynucleotides, amino acids and polypeptides, lipids, polysaccharides, small molecules, and protection groups.

In particular embodiments, the small molecule is a drug such as dichloroacetic acid (DCA):

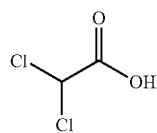

In some embodiments, the amino acid end group is protected. For example in some embodiments the conjugate has the formula Pg-AA1-C-AA1-Pg or Pg-AA2-C-AA1-Pg or Pg-AA1-C-AA2-Pg or C-AA1-Pg, or Pg-AA1-C wherein "AA1" and "AA2" represent different amino acids, and "C" represents curcumin, and "Pg" represents an amino-acid protecting group or diachloroacetic acid. Amino acid-protecting groups and method of use thereof are well known in the art. See, for example, Isidro-Llobet, et al., *Chem. Rev.*, 109 (6):2455-2504 (2009), which is specifically incorporated by reference herein in its entirety. Suitable amine protecting groups include, but are not limited to, carbobenzyloxy (Cbz), p-Methoxybenzyl carbonyl (Moz or MeOZ), tert-butyloxycarbonyl (Boc), Fluorenylmethyloxycarbonyl (FMOC) carbamate, acetyl (Ac), benzoyl (Bz), benzyl (Bn), p-Methoxybenzyl (PMB), 3,4-Dimethoxybenzyl (DMPM), p-methoxyphenyl (PMP) group, tosyl (Ts), and trichloroethyl chloroformate (Troc). In particular embodiments, the protecting group is carboxybenzyl (Cbz), Fluorenylmethyloxycarbonyl (FMOC) carbamate, or tert-butyloxycarbonyl (Boc).

2. Exemplary Curcumin Conjugates

It is believed that coupling curcumin with amino acids and DCA, will yield potent hybrid molecules with greater than additive qualities and diminished side effects. To do this, optimal reaction conditions were established, which involved utilizing different coupling reagents and solvents at varied temperatures. Once favorable conditions were obtained, several curcumin-amino acid conjugates and curcumin-amino acid-DCA hybrid conjugates were successfully synthesized in excellent yield without alterations to chirality. In doing so, an efficient methodology for synthesizing these conjugates was developed. Exemplary curcumin conjugates are illustrated in Tables 1-4 below.

a. Without Protecting Group

In some embodiments, the curcumin conjugate includes or is any one of compounds 1-1 to 1-11 of Table 1.

TABLE 1

Amino acid-Curcumin Conjugates without Protecting Group

| S. No | Structure | IUPAC name |
|---|---|---|
| 1-1 | [structure of curcumin conjugate with two phenylalanine groups] | ((1E,6E)-3,5-dioxohepta-1,6-diene-1,7-diyl)bis(2-methoxy-4,1-phenylene) (2S,2'S)-bis(2-amino-3-phenylpropanoate) |

TABLE 1-continued

| | Amino acid-Curcumin Conjugates without Protecting Group | |
|---|---|---|
| S. No | Structure | IUPAC name |
| 1-2 | | ((1E,6E)-3,5-dioxohepta-1,6-diene-1,7-diyl)bis(2-methoxy-4,1-phenylene) bis(2-aminoacetate) |
| 1-3 | | ((1E,6E)-3,5-dioxohepta-1,6-diene-1,7-diyl)bis(2-methoxy-4,1-phenylene) (2S,2'S)-bis(2-aminopropanoate) |
| 1-4 | | ((1E,6E)-3,5-dioxohepta-1,6-diene-1,7-diyl)bis(2-methoxy-4,1-phenylene) (2S,2'S)-bis(2,4-diamino-4-oxobutanoate) |
| 1-5 | | ((1E,6E)-3,5-dioxohepta-1,6-diene-1,7-diyl)bis(2-methoxy-4,1-phenylene) (2S,2'S)-bis(2,5-diamino-5-oxopentanoate) |
| 1-6 | | ((1E,6E)-3,5-dioxohepta-1,6-diene-1,7-diyl)bis(2-methoxy-4,1-phenylene) (2S,2'S,3R,3'R)-bis(2-amino-3-methylpentanoate) |

TABLE 1-continued

Amino acid-Curcumin Conjugates without Protecting Group

| S. No | Structure | IUPAC name |
|---|---|---|
| 1-7 | 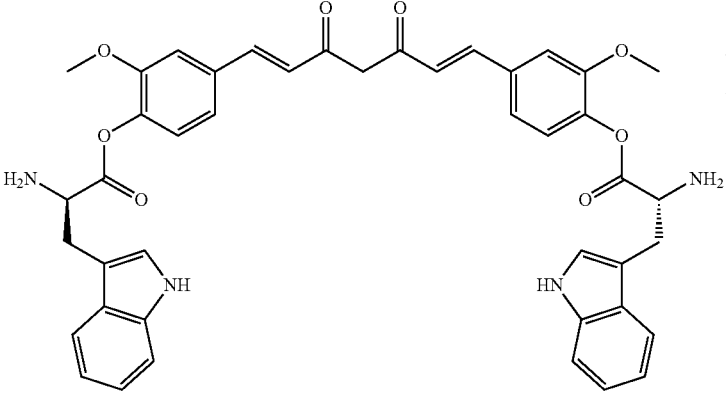 [SMILES: COc1cc(/C=C/C(=O)CC(=O)/C=C/c2ccc(OC(=O)[C@H](N)Cc3c[nH]c4ccccc34)c(OC)c2)ccc1OC(=O)[C@H](N)Cc1c[nH]c2ccccc12] | ((1E,6E)-3,5-dioxohepta-1,6-diene-1,7-diyl)bis(2-methoxy-4,1-phenylene) (2R,2′R)-bis(2-amino-3-(1H-indol-3-yl)propanoate) |
| 1-8 | 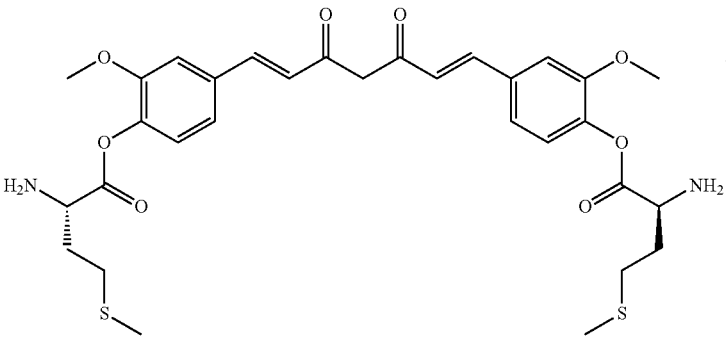 [SMILES: COc1cc(/C=C/C(=O)CC(=O)/C=C/c2ccc(OC(=O)[C@@H](N)CCSC)c(OC)c2)ccc1OC(=O)[C@@H](N)CCSC] | ((1E,6E)-3,5-dioxohepta-1,6-diene-1,7-diyl)bis(2-methoxy-4,1-phenylene) (2S,2′S)-bis(2-amino-4-(methylthio)butanoate) |
| 1-9 | 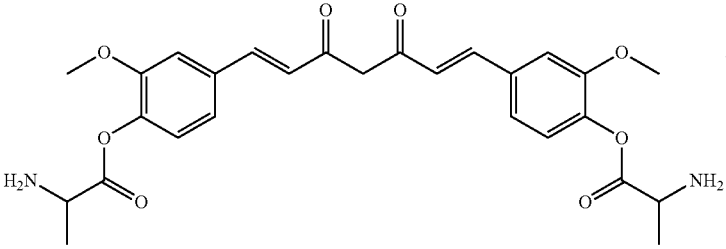 [SMILES: COc1cc(/C=C/C(=O)CC(=O)/C=C/c2ccc(OC(=O)C(C)N)c(OC)c2)ccc1OC(=O)C(C)N] | ((1E,6E)-3,5-dioxohepta-1,6-diene-1,7-diyl)bis(2-methoxy-4,1-phenylene) bis(2-aminopropanoate) |
| 1-10 | 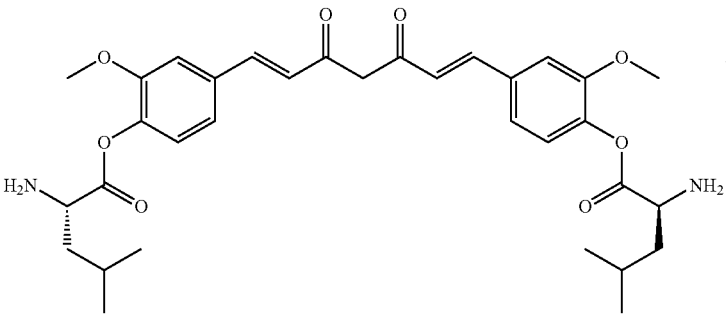 [SMILES: COc1cc(/C=C/C(=O)CC(=O)/C=C/c2ccc(OC(=O)[C@@H](N)CC(C)C)c(OC)c2)ccc1OC(=O)[C@@H](N)CC(C)C] | ((1E,6E)-3,5-dioxohepta-1,6-diene-1,7-diyl)bis(2-methoxy-4,1-phenylene) (2S,2′S)-bis(2-amino-4-methylpentanoate) |

TABLE 1-continued

Amino acid-Curcumin Conjugates without Protecting Group

| S. No | Structure | IUPAC name |
|---|---|---|
| 1-11 | 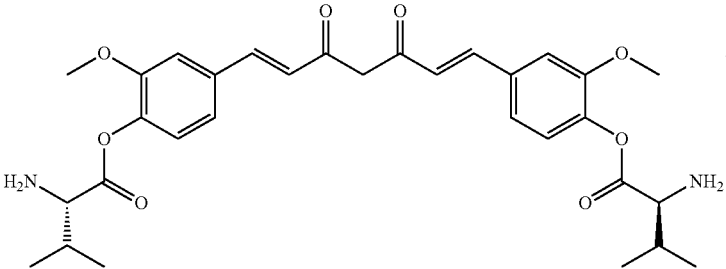 [SMILES: COc1cc(/C=C/C(=O)CC(=O)/C=C/c2ccc(OC(=O)[C@@H](N)C(C)C)c(OC)c2)ccc1OC(=O)[C@@H](N)C(C)C] | ((1E,6E)-3,5-dioxohepta-1,6-diene-1,7-diyl)bis(2-methoxy-4,1-phenylene) (2S,2'S)-bis(2-amino-3-methylbutanoate) | b. With Protecting Group

In some embodiments, the curcumin conjugate includes or is any one of compounds 2-4 to 2-31 of Table 2.

Compounds 2-1, 2-2, and 2-3 (indomethancin, ibuprofen, and unconjugated curcumin, respectively) in Table 2 were utilized as control compounds in the experiments discussed in more detail below.

TABLE 2

Amino acid-Curcumin Conjugates with Protecting Group

| S. No. | Structure | IUPAC name |
|---|---|---|
| 2-1 | Indomethacin | 2-(1-(4-chlorobenzoyl)-5-methoxy-2-methyl-1H-indol-3-yl)acetic acid |
| 2-2 | Ibuprofen | 2-(4-isobutylphenyl)propanoic acid |
| 2-3 | Curcumin | (1E,6E)-1,7-bis(4-hydroxy-3-methoxyphenyl)hepta-1,6-diene-3,5-dione |

TABLE 2-continued

Amino acid-Curcumin Conjugates with Protecting Group

| S. No. | Structure | IUPAC name |
|---|---|---|
| 2-4 | Cbz-Gly-Cur | ((1E,6E)-3,5-dioxohepta-1,6-diene-1,7-diyl)bis(2-methoxy-4,1-phenylene) bis(2-(((benzyloxy)carbonyl)amino)acetate) |
| 2-5 | Cbz-Ala-Cur | ((1E,6E)-3,5-dioxohepta-1,6-diene-1,7-diyl)bis(2-methoxy-4,1-phenylene) (2S,2'S)-bis(2-(((benzyloxy)carbonyl)amino)propanoate) |
| 2-6 | Cbz-DL-Ala-Cur | ((1E,6E)-3,5-dioxohepta-1,6-diene-1,7-diyl)bis(2-methoxy-4,1-phenylene) bis(2-(((benzyloxy)carbonyl)amino)propanoate) |

TABLE 2-continued
Amino acid-Curcumin Conjugates with Protecting Group
| S. No. | Structure | IUPAC name |
|---|---|---|
| 2-7 | 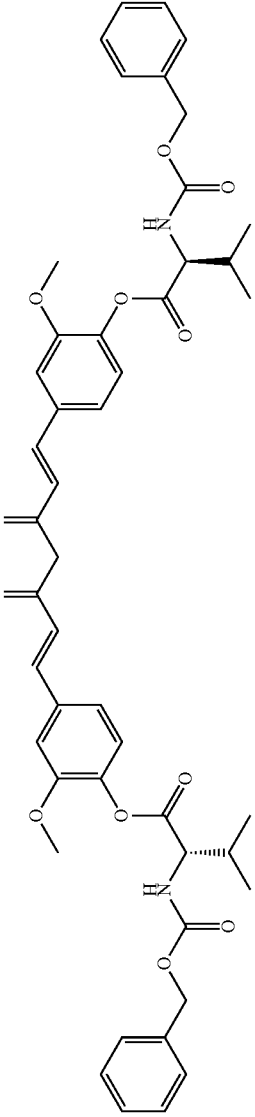 Cbz-Val-Cur | ((1E,6E)-3,5-dioxohepta-1,6-diene-1,7-diyl)bis(2-methoxy-4,1-phenylene) (2S,2'S)-bis(2-(((benzyloxy)carbonyl)amino)-3-methylbutanoate) |
| 2-8 | 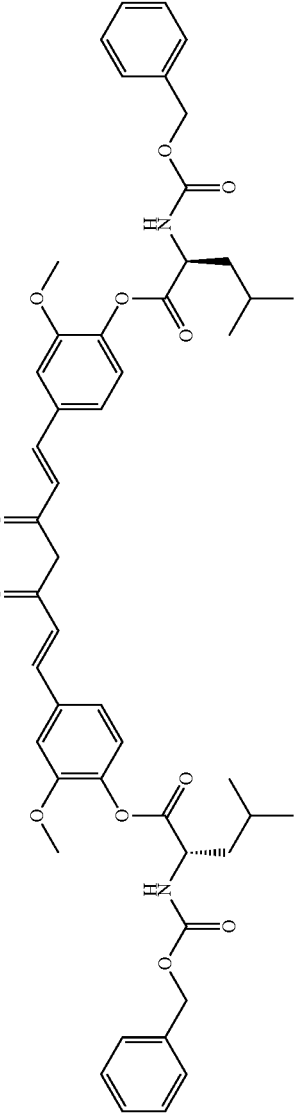 Cbz-Leu-Cur | ((1E,6E)-3,5-dioxohepta-1,6-diene-1,7-diyl)bis(2-methoxy-4,1-phenylene) (2S,2'S)-bis(2-(((benzyloxy)carbonyl)amino)-4-methylpentanoate) |

TABLE 2-continued

Amino acid-Curcumin Conjugates with Protecting Group

| S. No. | Structure | IUPAC name |
|---|---|---|
| 2-9 | Cbz-Met-Cur | (((1E,6E)-3,5-dioxohepta-1,6-diene-1,7-diyl)bis(2-methoxy-4,1-phenylene) (2S,2'S)-bis(2-(((benzyloxy)carbonyl)amino)-4-(methylthio)butanoate) |
| 2-10 | Cbz-Phe-Cur | (((1E,6E)-3,5-dioxohepta-1,6-diene-1,7-diyl)bis(2-methoxy-4,1-phenylene) (2S,2'S)-bis(2-(((benzyloxy)carbonyl)amino)-3-phenylpropanoate) |

TABLE 2-continued

Amino acid-Curcumin Conjugates with Protecting Group

| S. No. | Structure | IUPAC name |
|---|---|---|
| 2-11 | Cbz-Trp-Cur | (((1E,6E)-3,5-dioxohepta-1,6-diene-1,7-diyl)bis(2-methoxy-4,1-phenylene) (2S,2'S)-bis(2-(((benzyloxy)carbonyl)amino)-3-(1H-indol-3-yl)propanoate) |
| 2-12 | Z-D-Ala-Cur | (((1E,6E)-3,5-dioxohepta-1,6-diene-1,7-diyl)bis(2-methoxy-4,1-phenylene) (2R,2'R)-bis(2-(((benzyloxy)carbonyl)amino)propanoate) |

TABLE 2-continued
Amino acid-Curcumin Conjugates with Protecting Group
| S. No. | Structure | IUPAC name |
|---|---|---|
| 2-13 | 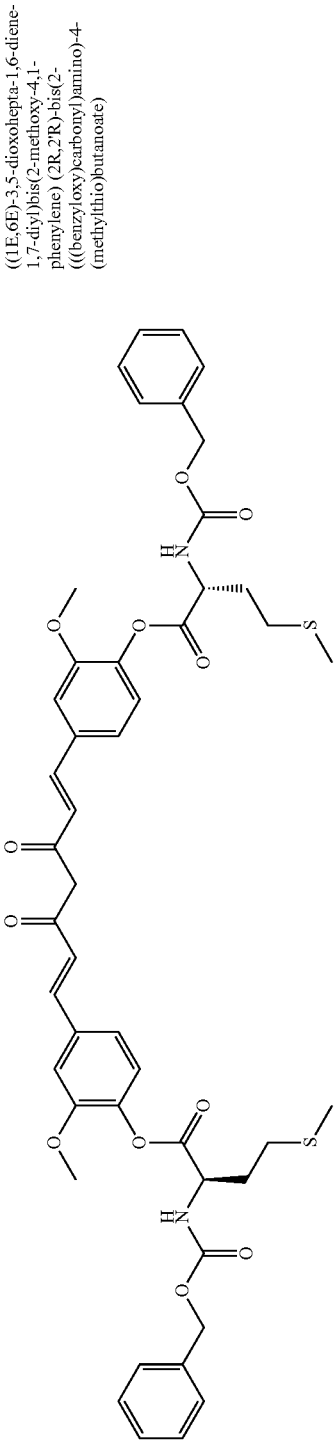<br>Z-D-Met-Cur | ((1E,6E)-3,5-dioxohepta-1,6-diene-1,7-diyl)bis(2-methoxy-4,1-phenylene) (2R,2'R)-bis(2-(((benzyloxy)carbonyl)amino)-4-(methylthio)butanoate) |
| 2-14 | 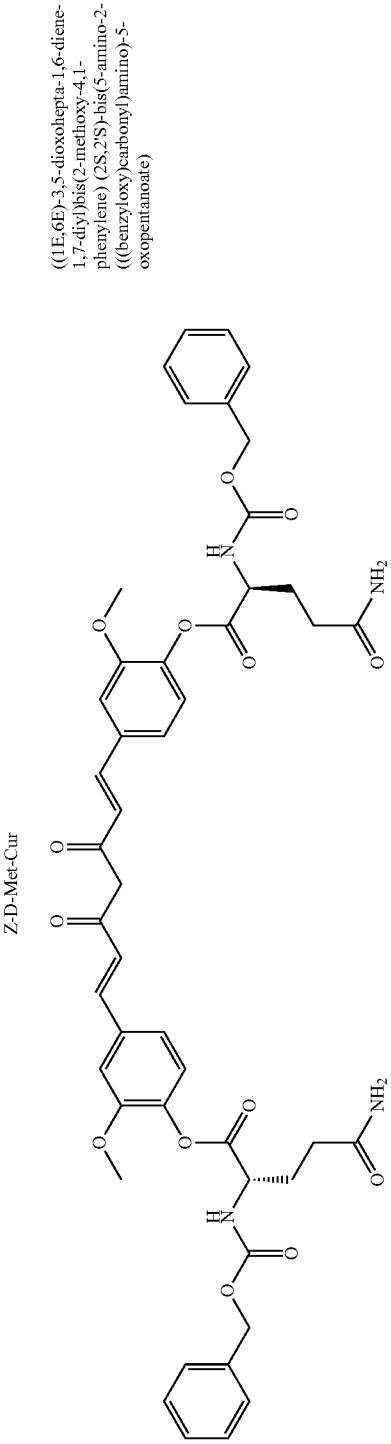<br>Z-L-Gln-Cur | ((1E,6E)-3,5-dioxohepta-1,6-diene-1,7-diyl)bis(2-methoxy-4,1-phenylene) (2S,2'S)-bis(5-amino-2-(((benzyloxy)carbonyl)amino)-5-oxopentanoate) |

TABLE 2-continued

Amino acid-Curcumin Conjugates with Protecting Group

| S. No. | Structure | IUPAC name |
|---|---|---|
| 2-15 |  Fmoc-Gly-Cur | (((1E,6E)-3,5-dioxohepta-1,6-diene-1,7-diyl)bis(2-methoxy-4,1-phenylene) bis(2-((((9H-fluoren-9-yl)methoxy)carbonyl)amino)acetate) |
| 2-16 |  Fmoc-Ala-Cur | (((1E,6E)-3,5-dioxohepta-1,6-diene-1,7-diyl)bis(2-methoxy-4,1-phenylene) (2S,2'S)-bis(2-((((9H-fluoren-9-yl)methoxy)carbonyl)amino)propanoate) |
| 2-17 | 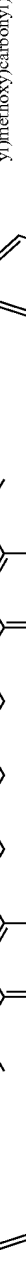 Fmoc-Val-Cur | (((1E,6E)-3,5-dioxohepta-1,6-diene-1,7-diyl)bis(2-methoxy-4,1-phenylene) (2S,2'S)-bis(2-((((9H-fluoren-9-yl)methoxy)carbonyl)amino)-3-methylbutanoate) |

TABLE 2-continued

Amino acid-Curcumin Conjugates with Protecting Group

| S. No. | Structure | IUPAC name |
|---|---|---|
| 2-18 | Fmoc-Leu-Cur | (((1E,6E)-3,5-dioxohepta-1,6-diene-1,7-diyl)bis(2-methoxy-4,1-phenylene) (2S,2'S)-bis(2-((((9H-fluoren-9-yl)methoxy)carbonyl)amino)-4-methylpentanoate) |
| 2-19 | Fmoc-Met-Cur | (((1E,6E)-3,5-dioxohepta-1,6-diene-1,7-diyl)bis(2-methoxy-4,1-phenylene) (2S,2'S)-bis(2-((((9H-fluoren-9-yl)methoxy)carbonyl)amino)-4-(methylthio)butanoate) |

TABLE 2-continued

Amino acid-Curcumin Conjugates with Protecting Group

| S. No. | Structure | IUPAC name |
|---|---|---|
| 2-20 | Fmoc-Phe-Cur | (((1E,6E)-3,5-dioxohepta-1,6-diene-1,7-diyl)bis(2-methoxy-4,1-phenylene) (2S,2'S)-bis(2-((((9H-fluoren-9-yl)methoxy)carbonyl)amino)-3-phenylpropanoate) |
| 2-21 | Boc-Gly-Cur | (((1E,6E)-3,5-dioxohepta-1,6-diene-1,7-diyl)bis(2-methoxy-4,1-phenylene) bis(2-((tert-butoxycarbonyl)amino)acetate) |

TABLE 2-continued

Amino acid-Curcumin Conjugates with Protecting Group

| S. No. | Structure | IUPAC name |
|---|---|---|
| 2-22 | Boc-L-Phe-Cur | (((1E,6E)-3,5-dioxohepta-1,6-diene-1,7-diyl)bis(2-methoxy-4,1-phenylene) (2S,2'S)-bis(2-((tert-butoxycarbonyl)amino)-3-phenyl)propanoate) |
| 2-23 | Boc-L-Ala-Cur | (((1E,6E)-3,5-dioxohepta-1,6-diene-1,7-diyl)bis(2-methoxy-4,1-phenylene) (2S,2'S)-bis(2-((tert-butoxycarbonyl)amino)propanoate) |
| 2-24 | Boc-DL-Ala-Cur | (((1E,6E)-3,5-dioxohepta-1,6-diene-1,7-diyl)bis(2-methoxy-4,1-phenylene) bis(2-((tert-butoxycarbonyl)amino)propanoate) |

TABLE 2-continued

Amino acid-Curcumin Conjugates with Protecting Group

| S. No. | Structure | IUPAC name |
|---|---|---|
| 2-25 | Boc-D-Ala-Cur | ((1E,6E)-3,5-dioxohepta-1,6-diene-1,7-diyl)bis(2-methoxy-4,1-phenylene) (2R,2R)-bis(2-((tert-butoxycarbonyl)amino)propanoate) |
| 2-26 | Boc-β-Ala-Cur | ((1E,6E)-3,5-dioxohepta-1,6-diene-1,7-diyl)bis(2-methoxy-4,1-phenylene) bis(3-((tert-butoxycarbonyl)amino)propanoate) |
| 2-27 | Boc-L-Met-Cur | ((1E,6E)-3,5-dioxohepta-1,6-diene-1,7-diyl)bis(2-methoxy-4,1-phenylene) (2S,2'S)-bis(2-((tert-butoxycarbonyl)amino)-4-(methylthio)butanoate) |

TABLE 2-continued

Amino acid-Curcumin Conjugates with Protecting Group

| S. No. | Structure | IUPAC name |
|---|---|---|
| 2-28 | Boc-D-Met-Cur | (((1E,6E)-3,5-dioxohepta-1,6-diene-1,7-diyl)bis(2-methoxy-4,1-phenylene) (2R,2'R)-bis(2-((tert-butoxycarbonyl)amino)-4-(methylthio)butanoate) |
| 2-29 | Boc-L-Val-Cur | (((1E,6E)-3,5-dioxohepta-1,6-diene-1,7-diyl)bis(2-methoxy-4,1-phenylene) (2S,2'S)-bis(2-((tert-butoxycarbonyl)amino)-3-methylbutanoate) |

TABLE 2-continued

Amino acid-Curcumin Conjugates with Protecting Group

| S. No. | Structure | IUPAC name |
|---|---|---|
| 2-30 | Boc-L-Ile-Cur | (((1E,6E)-3,5-dioxohepta-1,6-diene-1,7-diyl)bis(2-methoxy-4,1-phenylene) (2S,2'S,3S,3'S)-bis(2-((tert-butoxycarbonyl)amino)-3-methylpentanoate) |
| 2-31 | Boc-L-Gln-Cur | (((1E,6E)-3,5-dioxohepta-1,6-diene-1,7-diyl)bis(2-methoxy-4,1-phenylene) (2S,2'S)-bis(5-amino-2-((tert-butoxycarbonyl)amino)-5-oxopentanoate) | c. Curcumin-DCA Hybrids

In some embodiments, the curcumin conjugate is a curcumin-DCA hybrid conjugate that includes or is any one of compounds 3-1 to 3-13 of Table 3.

TABLE 3

DCA-Amino acid-Curcumin Hybrid Conjugates

| S. No | Structure | IUPAC name |
|---|---|---|
| 3-1 | 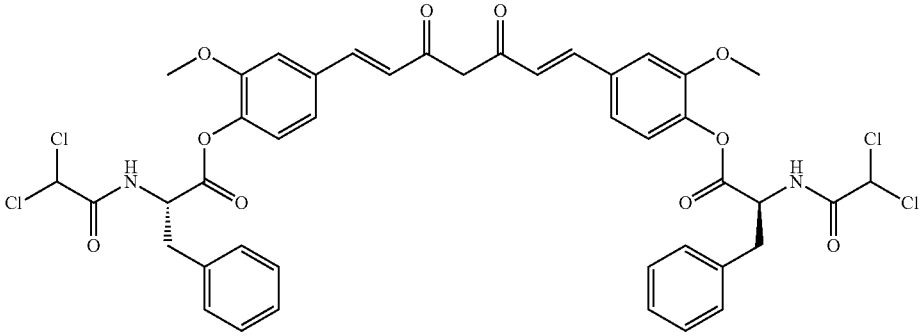 [SMILES: COc1cc(/C=C/C(=O)CC(=O)/C=C/c2ccc(OC(=O)[C@H](Cc3ccccc3)NC(=O)C(Cl)Cl)c(OC)c2)ccc1OC(=O)[C@H](Cc1ccccc1)NC(=O)C(Cl)Cl] | ((1E,6E)-3,5-dioxohepta-1,6-diene-1,7-diyl)bis(2-methoxy-4,1-phenylene) (2S,2'S)-bis(2-(2,2-dichloroacetamido)-3-phenylpropanoate) |
| 3-2 | 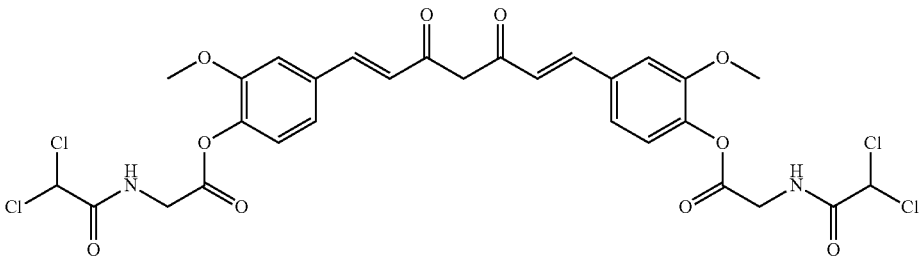 [SMILES: COc1cc(/C=C/C(=O)CC(=O)/C=C/c2ccc(OC(=O)CNC(=O)C(Cl)Cl)c(OC)c2)ccc1OC(=O)CNC(=O)C(Cl)Cl] | ((1E,6E)-3,5-dioxohepta-1,6-diene-1,7-diyl)bis(2-methoxy-4,1-phenylene) bis(2-(2,2-dichloroacetamido)acetate) |
| 3-3 | 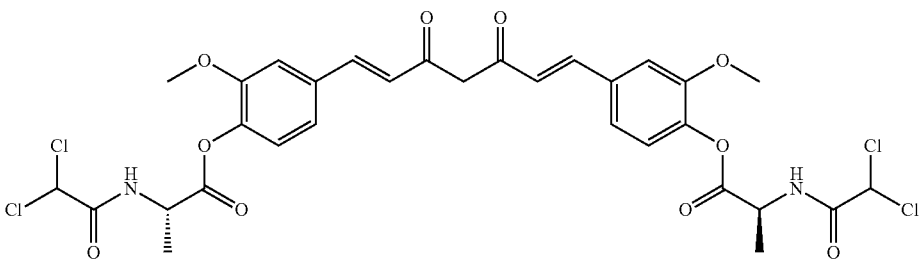 [SMILES: COc1cc(/C=C/C(=O)CC(=O)/C=C/c2ccc(OC(=O)[C@H](C)NC(=O)C(Cl)Cl)c(OC)c2)ccc1OC(=O)[C@H](C)NC(=O)C(Cl)Cl] | ((1E,6E)-3,5-dioxohepta-1,6-diene-1,7-diyl)bis(2-methoxy-4,1-phenylene) (2S,2'S)-bis(2-(2,2-dichloroacetamido)propanoate) |
| 3-4 | 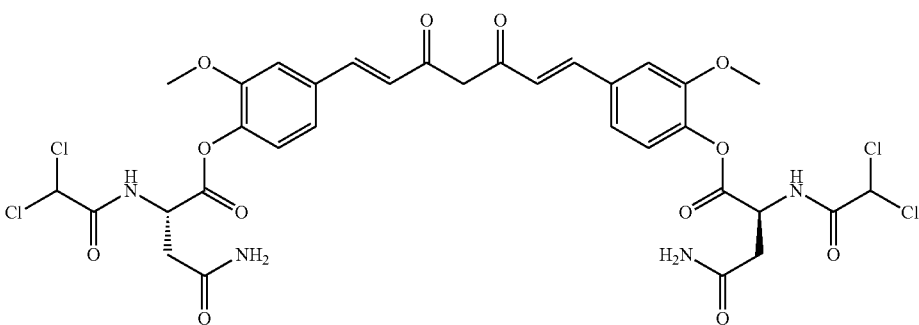 [SMILES: COc1cc(/C=C/C(=O)CC(=O)/C=C/c2ccc(OC(=O)[C@H](CC(N)=O)NC(=O)C(Cl)Cl)c(OC)c2)ccc1OC(=O)[C@H](CC(N)=O)NC(=O)C(Cl)Cl] | ((1E,6E)-3,5-dioxohepta-1,6-diene-1,7-diyl)bis(2-methoxy-4,1-phenylene) (2S,2'S)-bis(4-amino-2-(2,2-dichloroacetamido)-4-oxobutanoate) |

TABLE 3-continued

DCA-Amino acid-Curcumin Hybrid Conjugates

| S. No | Structure | IUPAC name |
|---|---|---|
| 3-5 | 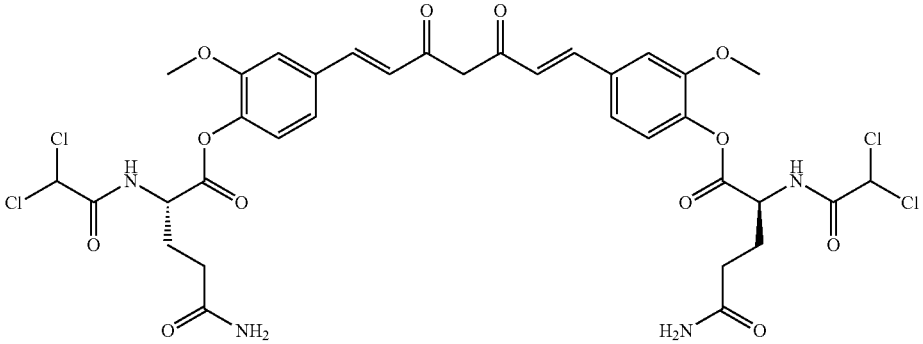 [SMILES: COc1cc(/C=C/C(=O)CC(=O)/C=C/c2ccc(OC(=O)[C@H](CCC(N)=O)NC(=O)C(Cl)Cl)c(OC)c2)ccc1OC(=O)[C@H](CCC(N)=O)NC(=O)C(Cl)Cl] | ((1E,6E)-3,5-dioxohepta-1,6-diene-1,7-diyl)bis(2-methoxy-4,1-phenylene) (2S,2'S)-bis(5-amino-2-(2,2-dichloroacetamido)-5-oxopentanoate) |
| 3-6 | 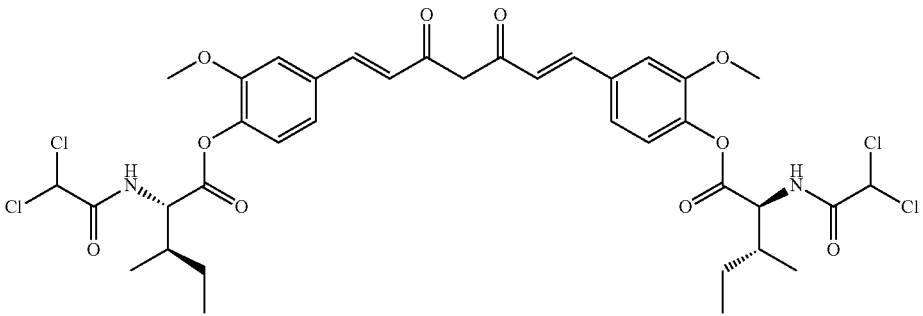 [SMILES: CC[C@@H](C)[C@H](NC(=O)C(Cl)Cl)C(=O)Oc1ccc(/C=C/C(=O)CC(=O)/C=C/c2ccc(OC(=O)[C@@H](NC(=O)C(Cl)Cl)[C@H](C)CC)c(OC)c2)cc1OC] | ((1E,6E)-3,5-dioxohepta-1,6-diene-1,7-diyl)bis(2-methoxy-4,1-phenylene) (2S,2'S,3R,3'R)-bis(2-(2,2-dichloroacetamido)-3-methylpentanoate) |
| 3-7 | 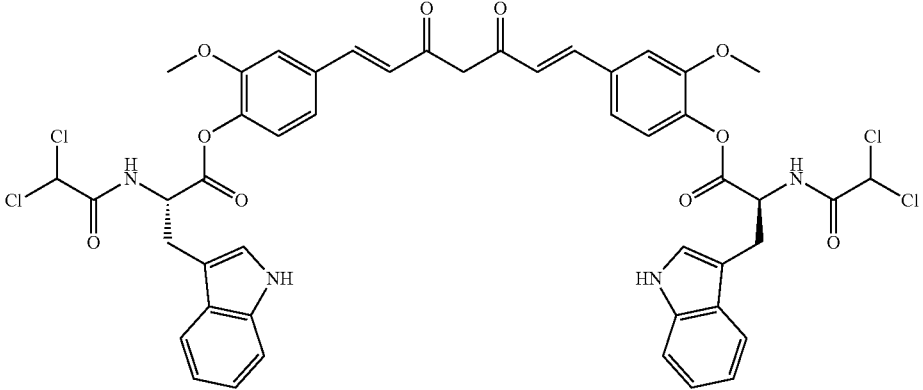 [SMILES: COc1cc(/C=C/C(=O)CC(=O)/C=C/c2ccc(OC(=O)[C@H](Cc3c[nH]c4ccccc34)NC(=O)C(Cl)Cl)c(OC)c2)ccc1OC(=O)[C@H](Cc1c[nH]c2ccccc12)NC(=O)C(Cl)Cl] | ((1E,6E)-3,5-dioxohepta-1,6-diene-1,7-diyl)bis(2-methoxy-4,1-phenylene) (2S,2'S)-bis(2-(2,2-dichloroacetamido)-3-(1H-indol-3-yl)propanoate) |
| 3-8 | 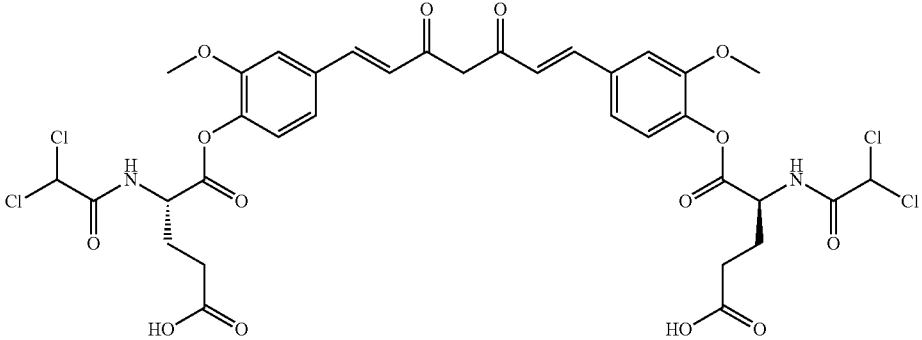 [SMILES: COc1cc(/C=C/C(=O)CC(=O)/C=C/c2ccc(OC(=O)[C@H](CCC(=O)O)NC(=O)C(Cl)Cl)c(OC)c2)ccc1OC(=O)[C@H](CCC(=O)O)NC(=O)C(Cl)Cl] | (4S,4'S)-5,5'-((((1E,6E)-3,5-dioxohepta-1,6-diene-1,7-diyl)bis(2-methoxy-4,1-phenylene))bis(oxy))bis(4-(2,2-dichloroacetamido)-5-oxopentanoic acid) |

TABLE 3-continued

DCA-Amino acid-Curcumin Hybrid Conjugates

| S. No | Structure | IUPAC name |
|---|---|---|
| 3-9 | 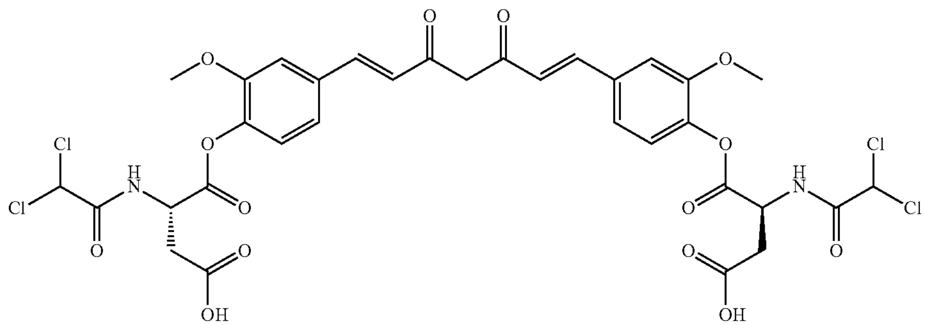 [SMILES: COc1cc(/C=C/C(=O)CC(=O)/C=C/c2ccc(OC(=O)[C@H](CC(=O)O)NC(=O)C(Cl)Cl)c(OC)c2)ccc1OC(=O)[C@H](CC(=O)O)NC(=O)C(Cl)Cl] | (3S,3'S)-4,4'-(((((1E,6E)-3,5-dioxohepta-1,6-diene-1,7-diyl)bis(2-methoxy-4,1-phenylene))bis(oxy))bis(3-(2,2-dichloroacetamido)-4-oxobutanoic acid) |
| 3-10 | 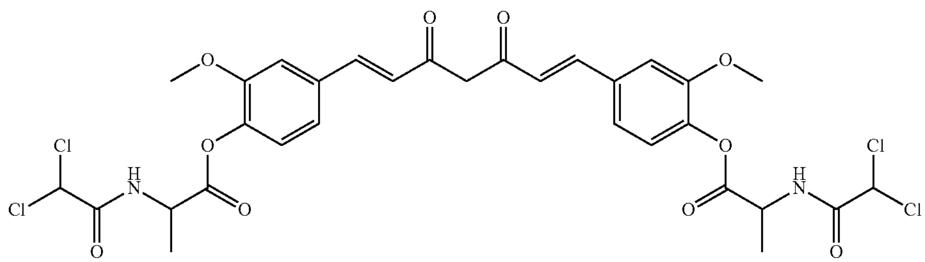 [SMILES: COc1cc(/C=C/C(=O)CC(=O)/C=C/c2ccc(OC(=O)C(C)NC(=O)C(Cl)Cl)c(OC)c2)ccc1OC(=O)C(C)NC(=O)C(Cl)Cl] | ((1E,6E)-3,5-dioxohepta-1,6-diene-1,7-diyl)bis(2-methoxy-4,1-phenylene) bis(2-(2,2-dichloroacetamido)propanoate) |
| 3-11 | 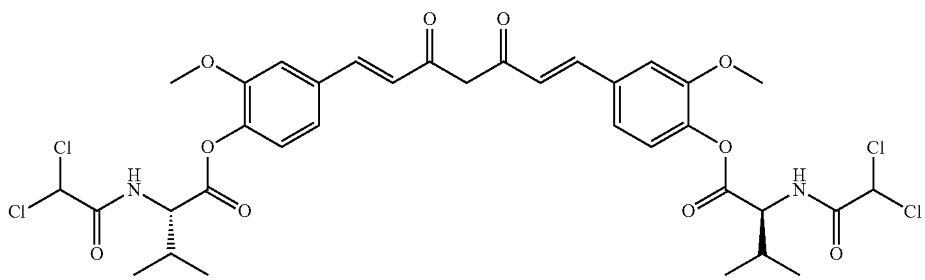 [SMILES: COc1cc(/C=C/C(=O)CC(=O)/C=C/c2ccc(OC(=O)[C@@H](NC(=O)C(Cl)Cl)C(C)C)c(OC)c2)ccc1OC(=O)[C@@H](NC(=O)C(Cl)Cl)C(C)C] | ((1E,6E)-3,5-dioxohepta-1,6-diene-1,7-diyl)bis(2-methoxy-4,1-phenylene) (2S,2'S)-bis(2-(2,2-dichloroacetamido)-3-methylbutanoate) |
| 3-12 | 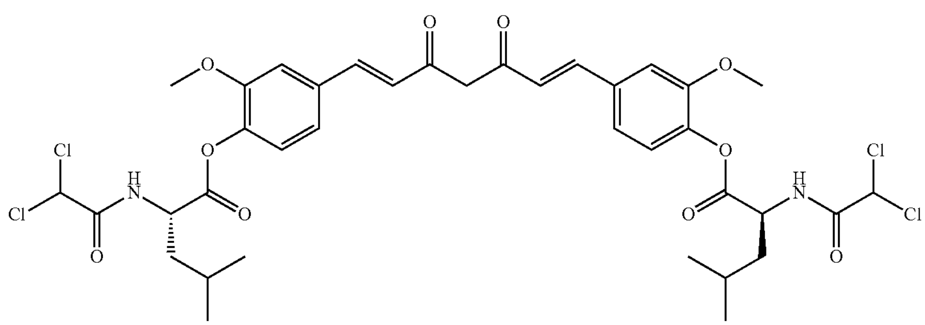 [SMILES: COc1cc(/C=C/C(=O)CC(=O)/C=C/c2ccc(OC(=O)[C@H](CC(C)C)NC(=O)C(Cl)Cl)c(OC)c2)ccc1OC(=O)[C@H](CC(C)C)NC(=O)C(Cl)Cl] | ((1E,6E)-3,5-dioxohepta-1,6-diene-1,7-diyl)bis(2-methoxy-4,1-phenylene) (2S,2'S)-bis(2-(2,2-dichloroacetamido)-4-methylpentanoate) |
| 3-13 | | ((1E,6E)-3,5-dioxohepta-1,6-diene-1,7-diyl)bis(2-methoxy-4,1-phenylene) bis(2-(2,2-dichloroacetamido)-4-(methylthio)butanoate) | d. Other Exemplary Curcumin Conjugates

In some embodiments, the curcumin conjugate is or includes any one of compounds 4-1 to 4-24 of Table 4.

TABLE 4
Other Exemplary Curcumin Conjugates
| S. No | Structure | IUPAC name |
|---|---|---|
| 4-1 | 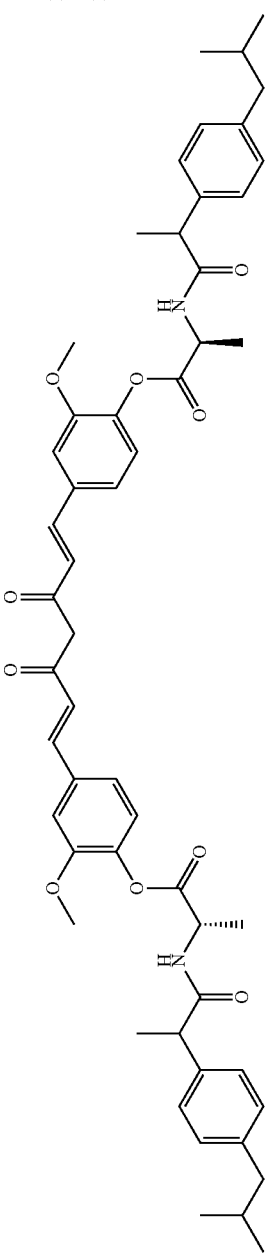 | (((1E,6E)-3,5-dioxohepta-1,6-diene-1,7-diyl)bis(2-methoxy-4,1-phenylene) (2S,2'S)-bis(2-(2-(4-isobutylphenyl)propanamido)propanoate) |
| 4-2 | 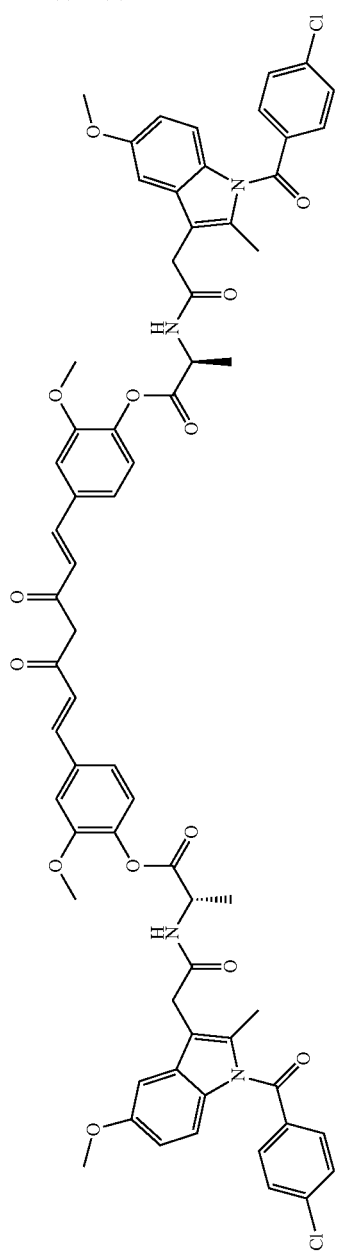 | (((1E,6E)-3,5-dioxohepta-1,6-diene-1,7-diyl)bis(2-methoxy-4,1-phenylene) (2S,2'S)-bis(2-(1-(4-chlorobenzoyl)-5-methoxy-2-methyl-1H-indol-3-yl)acetamido)propanoate) |
| 4-3 | 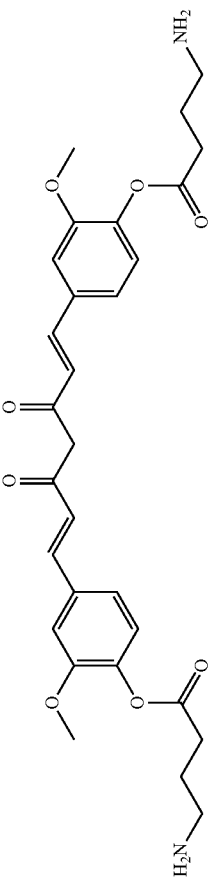 | (((1E,6E)-3,5-dioxohepta-1,6-diene-1,7-diyl)bis(2-methoxy-4,1-phenylene) bis(4-aminobutanoate) |

TABLE 4-continued

Other Exemplary Curcumin Conjugates

| S. No | Structure | IUPAC name |
|---|---|---|
| 4-4 | 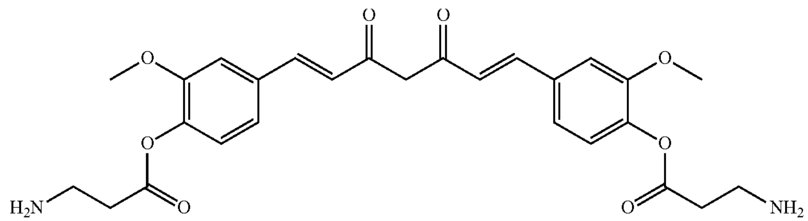 [SMILES: COc1cc(/C=C/C(=O)CC(=O)/C=C/c2ccc(OC(=O)CCN)c(OC)c2)ccc1OC(=O)CCN] | ((1E,6E)-3,5-dioxohepta-1,6-diene-1,7-diyl)bis(2-methoxy-4,1-phenylene) bis(3-aminopropanoate) |
| 4-5 | 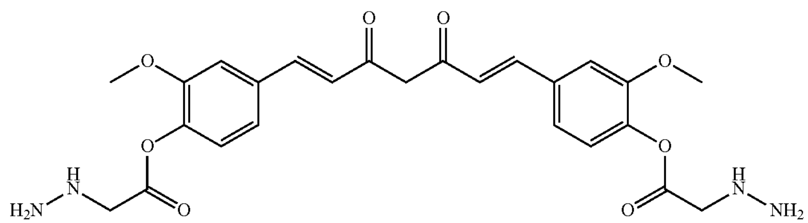 [SMILES: COc1cc(/C=C/C(=O)CC(=O)/C=C/c2ccc(OC(=O)CNN)c(OC)c2)ccc1OC(=O)CNN] | ((1E,6E)-3,5-dioxohepta-1,6-diene-1,7-diyl)bis(2-methoxy-4,1-phenylene) bis(2-hydrazinylacetate) |
| 4-6 | 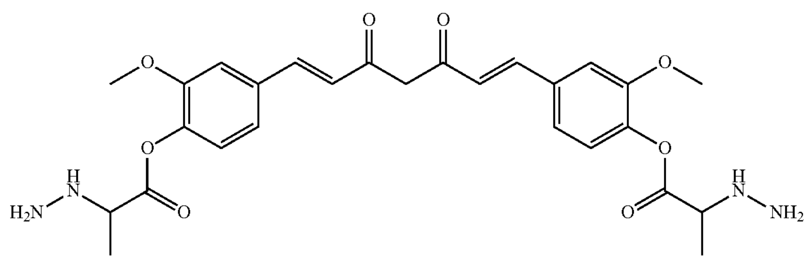 [SMILES: COc1cc(/C=C/C(=O)CC(=O)/C=C/c2ccc(OC(=O)C(C)NN)c(OC)c2)ccc1OC(=O)C(C)NN] | ((1E,6E)-3,5-dioxohepta-1,6-diene-1,7-diyl)bis(2-methoxy-4,1-phenylene) bis(2-hydrazinylpropanoate) |
| 4-7 | 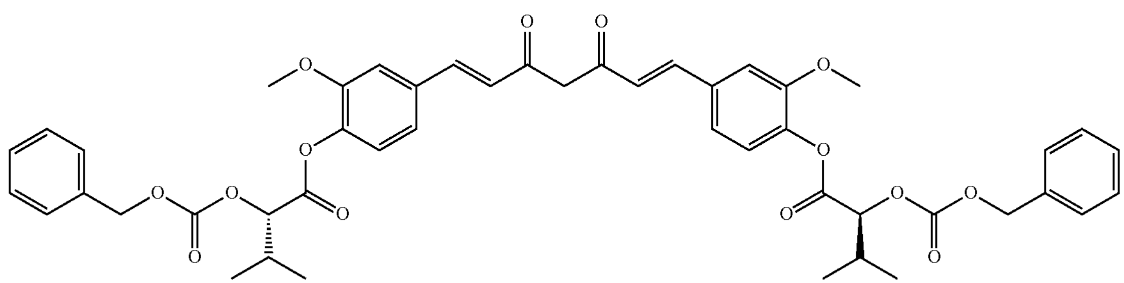 [SMILES: COc1cc(/C=C/C(=O)CC(=O)/C=C/c2ccc(OC(=O)[C@@H](OC(=O)OCc3ccccc3)C(C)C)c(OC)c2)ccc1OC(=O)[C@@H](OC(=O)OCc1ccccc1)C(C)C] | ((1E,6E)-3,5-dioxohepta-1,6-diene-1,7-diyl)bis(2-methoxy-4,1-phenylene) (2S,2'S)-bis(2-(((benzyloxy)carbonyl)oxy)-3-methylbutanoate) |

TABLE 4-continued

Other Exemplary Curcumin Conjugates

| S. No | Structure | IUPAC name |
|---|---|---|
| 4-8 | 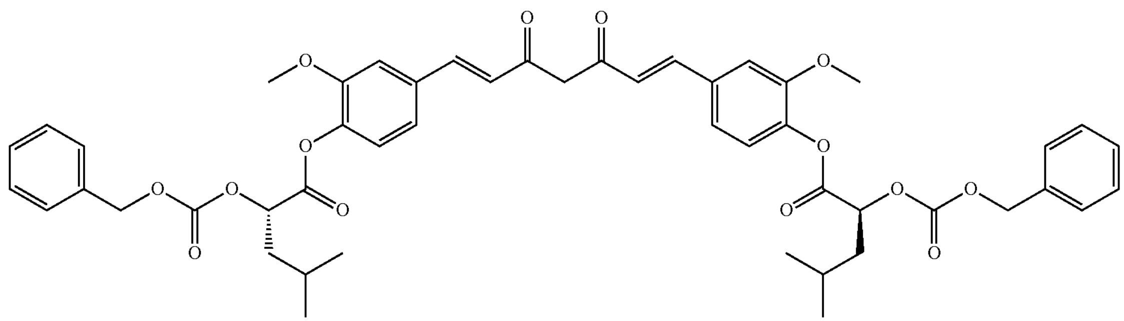 [SMILES: COc1cc(/C=C/C(=O)CC(=O)/C=C/c2ccc(OC(=O)[C@H](CC(C)C)OC(=O)OCc3ccccc3)c(OC)c2)ccc1OC(=O)[C@H](CC(C)C)OC(=O)OCc1ccccc1] | (((1E,6E)-3,5-dioxohepta-1,6-diene-1,7-diyl)bis(2-methoxy-4,1-phenylene) (2S,2'S)-bis(((benzyloxy)carbonyl)oxy)-4-methylpentanoate) |
| 4-9 | 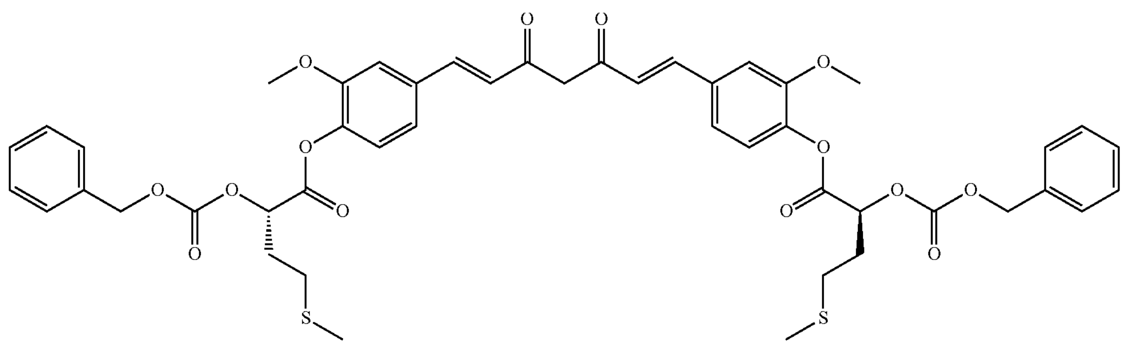 [SMILES: COc1cc(/C=C/C(=O)CC(=O)/C=C/c2ccc(OC(=O)[C@H](CCSC)OC(=O)OCc3ccccc3)c(OC)c2)ccc1OC(=O)[C@H](CCSC)OC(=O)OCc1ccccc1] | (((1E,6E)-3,5-dioxohepta-1,6-diene-1,7-diyl)bis(2-methoxy-4,1-phenylene) (2S,2'S)-bis(((benzyloxy)carbonyl)oxy)-4-(methylthio)butanoate) |

TABLE 4-continued

Other Exemplary Curcumin Conjugates

| S. No | Structure | IUPAC name |
|---|---|---|
| 4-10 | 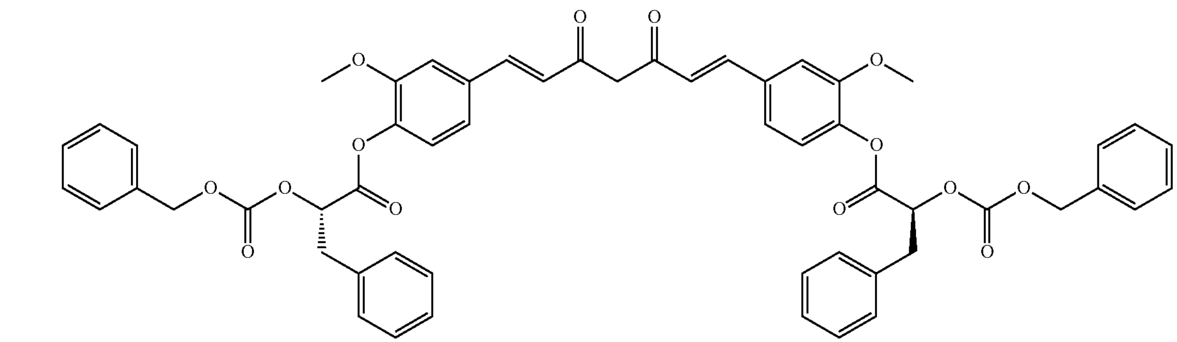 [SMILES: COc1cc(/C=C/C(=O)CC(=O)/C=C/c2ccc(OC(=O)[C@H](Cc3ccccc3)OC(=O)OCc3ccccc3)c(OC)c2)ccc1OC(=O)[C@H](Cc1ccccc1)OC(=O)OCc1ccccc1] | ((1E,6E)-3,5-dioxohepta-1,6-diene-1,7-diyl)bis(2-methoxy-4,1-phenylene) (2S,2'S)-bis(2-(((benzyloxy)carbonyl)oxy)-3-phenylpropanoate) |
| 4-11 | 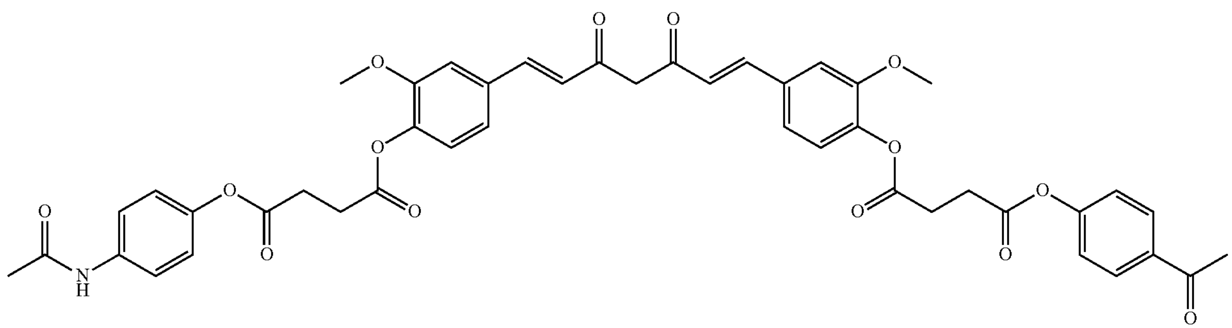 [SMILES: COc1cc(/C=C/C(=O)CC(=O)/C=C/c2ccc(OC(=O)CCC(=O)Oc3ccc(C(C)=O)cc3)c(OC)c2)ccc1OC(=O)CCC(=O)Oc1ccc(NC(C)=O)cc1] | 4-((1E,6E)-7-(4-((4-(4-acetamidophenoxy)-4-oxobutanoyl)oxy)-3-methoxyphenyl)-3,5-dioxohepta-1,6-dien-1-yl)-2-methoxyphenyl (4-acetylphenyl) succinate |
| 4-12 | 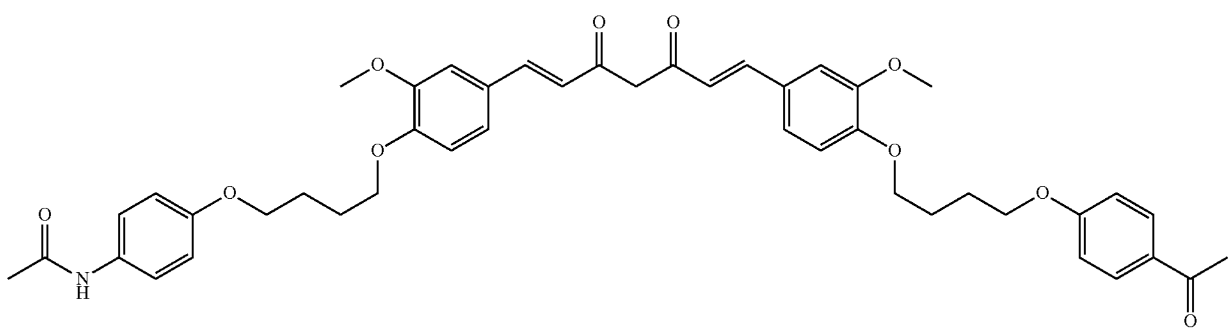 [SMILES: COc1cc(/C=C/C(=O)CC(=O)/C=C/c2ccc(OCCCCOc3ccc(C(C)=O)cc3)c(OC)c2)ccc1OCCCCOc1ccc(NC(C)=O)cc1] | N-(4-(4-(4-((1E,6E)-7-(4-(4-acetylphenoxy)butoxy)-3-methoxyphenyl)-3,5-dioxohepta-1,6-dien-1-yl)-2-methoxyphenoxy)butoxy)phenyl) acetamide |

TABLE 4-continued

Other Exemplary Curcumin Conjugates

| S. No | Structure | IUPAC name |
|---|---|---|
| 4-13 | | 3-bis(4-acetamidophenyl) O1,O1'-((((1E,6E)-3,5-dioxohepta-1,6-diene-1,7-diyl)bis(2-methoxy-4,1-phenylene)) bis(2-methylmalonate) |
| 4-14 | HCl-Gly-Cur | 2,2'-(((1E,6E)-3,5-dioxohepta-1,6-diene-1,7-diyl)bis(2-methoxy-4,1-phenylene)bis(oxy)bis(2-oxoethan-1-aminium) chloride |
| 4-15 | HCl-L-Phe-Cur | (2S,2'S)-1,1'-((((1E,6E)-3,5-dioxohepta-1,6-diene-1,7-diyl)bis(2-methoxy-4,1-phenylene)bis(oxy))bis(1-oxo-3-phenylpropan-2-aminium) chloride |

TABLE 4-continued

Other Exemplary Curcumin Conjugates

| S. No | Structure | IUPAC name |
|---|---|---|
| 4-16 | HCl-L-Ala-Cur | (2S,2'S)-1,1'-((((1E,6E)-3,5-dioxohepta-1,6-diene-1,7-diyl)bis(2-methoxy-4,1-phenylene))bis(oxy))bis(1-oxopropan-2-aminium) chloride |
| 4-17 | HCl-DL-Ala-Cur | 1,1'-((((1E,6E)-3,5-dioxohepta-1,6-diene-1,7-diyl)bis(2-methoxy-4,1-phenylene))bis(oxy))bis(1-oxopropan-2-aminium) chloride |
| 4-18 | HCl-D-Ala-Cur | (2R,2'R)-1,1'-((((1E,6E)-3,5-dioxohepta-1,6-diene-1,7-diyl)bis(2-methoxy-4,1-phenylene))bis(oxy))bis(1-oxopropan-2-aminium) chloride |

TABLE 4-continued

Other Exemplary Curcumin Conjugates

| S. No | Structure | IUPAC name |
|---|---|---|
| 4-19 | HCl-β-Ala-Cur | 3,3'-((((1E,6E)-3,5-dioxohepta-1,6-diene-1,7-diyl)bis(2-methoxy-4,1-phenylene)bis(oxy))bis(3-oxopropan-1-aminium) chloride |
| 4-20 | HCl-L-Met-Cur | (2S,2'S)-1,1'-((((1E,6E)-3,5-dioxohepta-1,6-diene-1,7-diyl)bis(2-methoxy-4,1-phenylene)bis(oxy))bis(4-(methylthio)-1-oxobutan-2-aminium) chloride |

TABLE 4-continued
Other Exemplary Curcumin Conjugates
| S. No | Structure | IUPAC name |
|---|---|---|
| 4-21 | 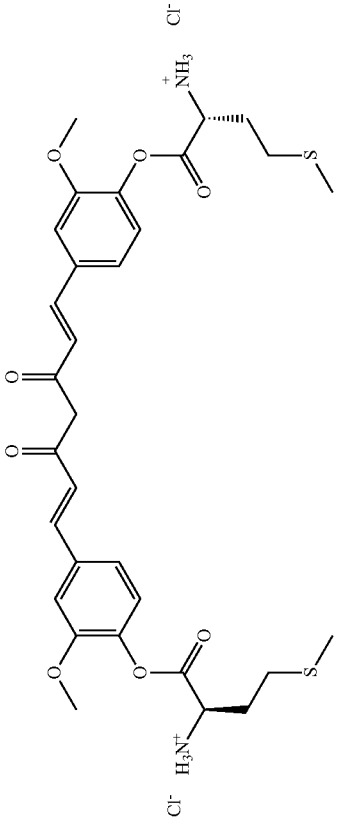 HCl-D-Met-Cur | (2R,2'R)-1,1'-((((1E,6E)-3,5-dioxohepta-1,6-diene-1,7-diyl)bis(2-methoxy-4,1-phenylene))bis(oxy))bis(4-(methylthio))-1-oxobutan-2-aminium) chloride |
| 4-22 | 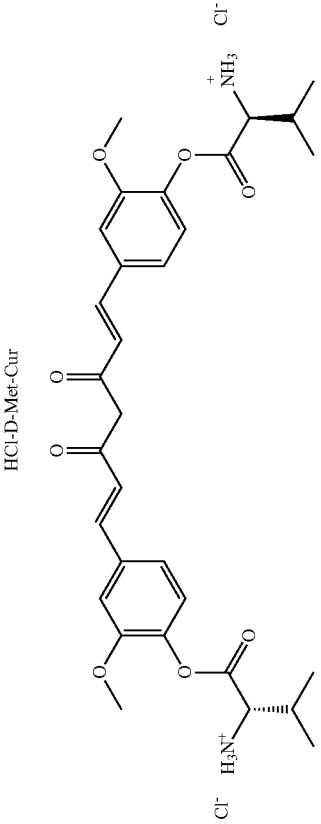 HCl-L-Val-Cur | (2S,2'S)-1,1'-((((1E,6E)-3,5-dioxohepta-1,6-diene-1,7-diyl)bis(2-methoxy-4,1-phenylene))bis(oxy))bis(3-methyl-1-oxobutan-2-aminium) chloride |

TABLE 4-continued
Other Exemplary Curcumin Conjugates
| S. No | Structure | IUPAC name |
|---|---|---|
| 4-23 | HCl-L-Ile-Cur 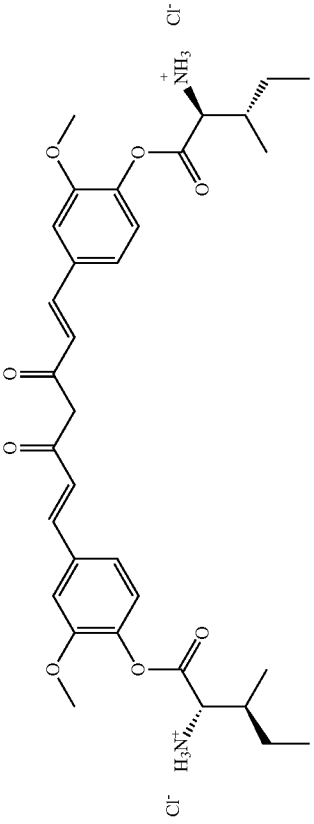 | (2S,2'S,3S,3'S)-1,1'-(((1E,6E)-3,5-dioxohepta-1,6-diene-1,7-diyl)bis(2-methoxy-4,1-phenylene)bis(oxy))bis(3-methyl-1-oxopentan-2-aminium) chloride |
| 4-24 | HCl-L-Gln-Cur 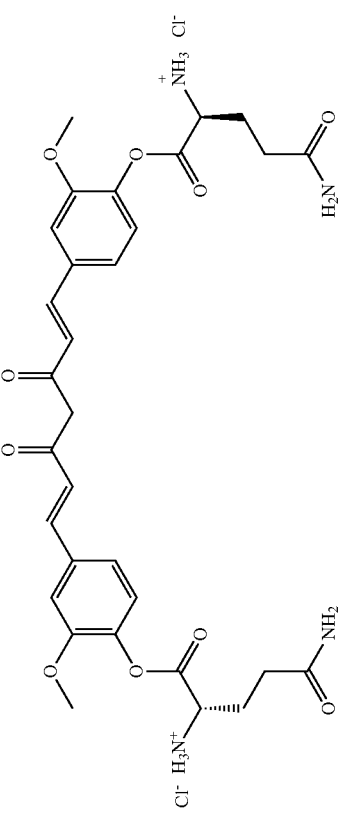 | (2S,2'S)-1,1'-(((1E,6E)-3,5-dioxohepta-1,6-diene-1,7-diyl)bis(2-methoxy-4,1-phenylene)bis(oxy))bis(5-amino-1,5-dioxopentan-2-aminium) chloride |

B. Formulations and Pharmaceutical Compositions

The disclosed compounds and mixtures thereof can be formulated in a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration. The compositions can be administered systemically.

Drugs can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995) which provides information on carriers, materials, equipment and process for preparing tablets and capsules and delayed release dosage forms of tablets, capsules, and granules.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Formulations for Parenteral Administration

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Oral Immediate Release Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudrage (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER' 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

3. Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

4. Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

5. Formulations for Mucosal and Pulmonary Administration

Active agent(s) and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PART LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

6. Topical and Transdermal Formulations

Transdermal formulations may also be prepared. These will typically be gels, ointments, lotions, sprays, or patches, all of which can be prepared using standard technology. Transdermal formulations can include penetration enhancers.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophillic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited to, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ' 721 (stearyl poly (21) oxyethylene ether) (ICI Americas Inc. Corp.). Chemical penetrations and methods of increasing transdermal drug delivery are described in Inayat, et al., Tropical Journal of Pharmaceutical Research, 8(2):173-179 (2009) and Fox, et al., Molecules, 16:10507-10540 (2011). In some embodiments, the penetration enhancer is, or includes, an alcohol such ethanol, or others disclosed herein or known in the art.

Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption.

Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676,961, 5,985,311, and 5,948,433.

In some embodiments, the composition is formulated for transdermal delivery and administered using a transdermal patch. In some embodiments, the formulation, the patch, or both are designed for extended release of the curcumin conjugate.

Exemplary symptoms, pharmacologic, and physiologic effects are discussed in more detail below.

III. Methods of Treatment

The curcumin conjugates and pharmaceutical compositions thereof can be used in dietary, cosmetic, and medical applications. For example, a curcumin conjugate can be administered to a subject in need thereof in an effective amount to treat a disease or disorder or otherwise provide a desired pharmacologic and/or physiologic effect.

In some embodiments, the curcumin conjugates are used to treat a disease or disorder or induce or increase a physiological effect previously identified as treatable by curcumin. For example, curcumin regulates the expression of inflammatory enzymes, cytokines, adhesion molecules, and cell survival proteins by modulating the activation of various transcription factors (Goel, et al., *Biochemical Pharmacology*, 75(4):787-809 (2008).

Curcumin also downregulates cyclin D1, cyclin E and MDM2; and upregulates p21, p27, and p53, and various preclinical cell culture and animal studies indicate that curcumin can be used as an antiproliferative, anti-invasive, and antiangiogenic agent; as a mediator of chemoresistance and radioresistance; as a chemopreventive agent; and as a therapeutic agent in wound healing, diabetes, neurodegenerative diseases such as Alzheimer disease and Parkinson disease, cardiovascular disease, pulmonary disease, and arthritis (Goel, et al., *Biochemical Pharmacology*, 75(4): 787-809 (2008). Clinical trials clinical trial support a therapeutic role for curcumin in diseases such as familial adenomatous polyposis, inflammatory bowel disease, ulcerative colitis, colon cancer, pancreatic cancer, hypercholesteremia, atherosclerosis, pancreatitis, psoriasis, chronic anterior uveitis and arthritis. As discussed in more detail below, in some embodiments, the conjugates are used to treat inflammation, cancer, or an infection.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects).

In some embodiments, the effect of the treatment is compared to a conventional treatment that is known the art, such as one of those discussed herein. Preferably, the disclosed compositions have less toxicity than curcumin at the same dosage, a greater potency or other pharmacological effect than curcumin at the same dosage, or a combination thereof. In some embodiments, the compositions can be administered at a lower dosage than curcumin, but achieve a greater therapeutic effect, lower toxicity, or a combination thereof.

Pilot phase I clinical trials have shown curcumin to be safe even when consumed at a daily dose of 12 g for 3 months (Goel, et al., *Biochemical Pharmacology*, 75(4):787-809 (2008)). In general, by way of example only, dosage forms useful in the disclosed methods can include doses in the range of 0.1 mg to 25 g, 100 mg to 20 g, 100 mg to 15 g, with doses of 1 mg, 5 mg, 7.5 mg, 10 mg, 25 mg, 50 mg, 75 mg, 100 mg, 250 mg, 500 mg, 750 mg, 1 g, 2.5 g, 5 g, 7.5 g, an 10 g being specific examples of doses. Typically, such dosages are administered once, twice, or three times daily, or once every 1, 2, 3, 4, 5, 6, or 7 days day to a human.

A. Treatment of Inflammation

Methods for treating, preventing and/or managing inflammation in a subject can include administering to a subject in need thereof an effective amount of the composition.

Administering the composition to a subject can, for example, reduce inflammation in the subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the inflammation in an subject not administered the composition. A reduction in inflammation can be measured by a reduction in a molecular manifestation of inflammation, for example, cytokine secretion (e.g., tumor necrosis factor alpha, interferon gamma), or a by a physical manifestation of inflammation, for example, swelling or redness.

In some embodiments the inflammation is associated with an inflammatory disorder or autoimmune disease. Methods for treating, preventing and/or managing an autoimmune disorder or inflammatory disorder in a subject, can include administering to a subject in need thereof an effective amount of the disclosed composition.

Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders.

Non-limiting examples of autoimmune disorders and inflammatory disorders include transplant rejection and graft versus host disease (GVHD). GVHD occurs when a donor's immune cells (e.g., donor's T cells) attack cells in the recipient subject's body. Transplant rejection occurs when a transplanted organ or tissue fails to be accepted by the body of the transplant recipient. In general, the transplant rejection is due to the immune system of the recipient (e.g., recipient's T cells) attacking the transplanted organ or tissue.

In some embodiments, the composition achieves one, two, three, four, or more of the following effects: (i) reduction or amelioration the severity of an autoimmune or inflammatory disorder or symptom associated therewith; (ii) reduction in the duration of a symptom associated with an autoimmune or inflammatory disorder; (iii) prevention of the progression of an autoimmune or inflammatory disorder, or symptom associated therewith; (iv) regression of an autoimmune or inflammatory disorder, or symptom associated therewith; (v) prevention of the development or onset of a symptom associated with an autoimmune or inflammatory disorder; (vi) prevention of the recurrence of a symptom associated with an autoimmune or inflammatory disorder; (vii) reduction in organ failure associated with an autoimmune or inflammatory disorder; (viii) reduction in the hospitalization of a subject; (ix) reduction in the hospitalization length; (x) an increase in the survival of a subject with an autoimmune or inflammatory disorder; (xi) a reduction in the number of symptoms associated with an autoimmune or inflammatory disorder; (xii) a reduction in inflammation of inflammatory cells; (xiii) a reduction in inflammatory cytokines; (xiv) a reduction in inflammation associated with an autoimmune or inflammatory disorder; (xv) improve life expectancy; (xvi) increase symptom-free survival; (xvii) increase the length of symptom-free remission; and/or (xviii) an enhancement, improvement, supplementation, complementation, or augmentation of the prophylactic or therapeutic effect(s) of another therapy.

B. Treatment of Cancer

Methods for preventing, treating, and/or managing cancer, can include administering to a subject in need thereof an effective amount of the composition. In a specific embodiment, the conjugate or a composition thereof is the only active agent administered to a subject (i.e., monotherapy) relative to a control.

In some embodiments, the composition increases cancer cell death, reduces tumor size, reduces cancer cell proliferation, reduce tumor growth, or a combination thereof relative to a control.

In some embodiments, the composition achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of patients; (xiii) a decrease in hospitalization rate; (ix) the prevention of the development or onset of one or more symptoms associated with cancer; (x) the reduction in the number of symptoms associated with cancer; (xi) an increase in symptom-free survival of cancer patients; (xii) improvement in quality of life as assessed by methods well known in the art; (xiii) the prevention in the recurrence of a tumor; (xiv) the regression of tumors and/or one or more symptoms associated therewith; (xvii) the inhibition of the progression of tumors and/or one or more symptoms associated therewith; (xviii) a reduction in the growth of a tumor; (xix) a decrease in tumor size (e.g., volume or diameter); (xx) a reduction in the formation of a newly formed tumor; (xxi) eradication, removal, or control of primary, regional and/or metastatic tumors; (xxii) a decrease in the number or size of metastases; (xxiii) a reduction in mortality; (xxiv) an increase in the tumor-free survival rate of patients; (xxv) an increase in relapse free survival; (xxvi) an increase in the number of patients in remission; (xxvii) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxviii) an increase in the length of remission in patients.

Cancers and related disorders that can be prevented, treated, or managed in accordance with the methods described herein include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, semi noma, anaplastic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The compositions can be used in the treatment of pre-malignant as well as malignant conditions. Pre-malignant conditions include hyperplasia, metaplasia, and dysplasia. Treatment of malignant conditions includes the treatment of primary as well as metastatic tumors. In a specific embodiment the cancer is melanoma, colon cancer, lung cancer, breast cancer, prostate cancer, cervical cancer, liver cancer, testicular cancer, brain cancer, pancreatic cancer, or renal cancer.

C. Treatment of Infections

Methods for preventing, treating, and/or managing an infectious disease and/or microbial growth can include administering to a subject in need thereof an effective amount of the composition. In a specific embodiment, the conjugate or a composition thereof is the only active agent administered to a subject.

In some embodiments, the composition reduces replication of the infectious agent, reduces tumor size or reduces the titer of the infectious agent relative to a control.

In some embodiments, the composition achieves one, two, three, four, or more of the following effects: (i) reduction or amelioration the severity of an infectious disease or symptom associated therewith; (ii) reduction in the duration of an infectious disease or symptom associated therewith; (iii) prevention of the progression of an infectious disease or symptom associated therewith; (iv) regression of an infectious disease or symptom associated therewith; (v) prevention of the development or onset of an infectious disease or symptom associated therewith; (vi) prevention of the recurrence of an infectious disease or symptom associated therewith; (vii) reduction or prevention of the spread of an infectious agent from one cell to another cell, one tissue to another tissue, or one organ to another organ; (viii) prevention or reduction of the spread/transmission of an infectious agent from one subject to another subject; (ix) reduction in organ failure associated with an infectious disease; (x) reduction in the hospitalization of a subject; (xi) reduction in the hospitalization length; (xii) an increase in the survival of a subject with an infectious disease; (xiii) elimination of an infectious disease; (xiii) inhibition or reduction in replication of an infectious agent; (xiv) inhibition or reduction in the entry of an infectious agent into a cell(s); (xv) inhibition or reduction of replication of the genome of an infectious agent; (xvi) inhibition or reduction in the synthesis of infectious agent proteins; (xvii) inhibition or reduction in the assembly of infectious agents; (xviii) inhibition or reduction in the release of infectious agents from a cell(s); (xviii)

reduction in the number or titer of an infectious agent; (xix) the reduction in the number of symptoms associated with an infectious disease; (xx) enhancement, improvement, supplementation, complementation, or augmentation of the prophylactic or therapeutic effect(s) of another therapy; and (xxi) prevention of the onset or progression of a secondary infection associated with an infectious disease.

Infectious diseases that can be treated, prevented, and/or managed by the compositions can be caused by infectious agents including but not limited to bacteria, fungi, protozae, and viruses. Viral diseases that can be prevented, treated and/or managed in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox.

Bacterial diseases caused by bacteria (e.g., *Escherichia coli, Klebsiella pneumoniae, Staphylococcus aureus, Enterococcus faecalis, Proteus vulgaris, Staphylococcus viridans,* and *Pseudomonas aeruginosa*) that can be prevented, treated and/or managed in accordance with the methods described herein include, but are not limited to, mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium,* pertissus, cholera, plague, diptheria, *chlamydia, S. aureus* and *legionella*.

Protozoal diseases caused by protozoa that can be prevented, treated and/or managed in accordance with the methods described herein include, but are not limited to, *leishmania,* kokzidioa, trypanosome schistosoma or malaria. Parasitic diseases caused by parasites that can be prevented, treated and/or managed in accordance with the methods described herein include, but are not limited to, chlamydia and rickettsia.

Fungal infections that can be prevented, treated and/or managed in accordance with the methods described herein include, but are not limited to, *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis,* paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

IV. Combination Therapies

In some embodiments, the curcumin conjugate(s) is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of curcumin conjugate(s). The different active agents can have the same or different mechanisms of action. In some embodiments, the combination results in an additive effect on the treatment of the disease or disorder. In some embodiments, the combinations results in a more than additive effect on the treatment of the disease or disorder. The additional active ingredients can be chemotherapeutic agents, immunomodulatory agents, and anti-inflammatory agents. For example, the disclosed compositions can be administered to a subject in need thereof in combination with: an antimicrobial such as an antibiotic, or an antifungal, or an antiviral, or an antiparasitic, or an essential oil, or a combination thereof.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

The pharmaceutical compositions can be formulated as a pharmaceutical dosage unit, also referred to as a unit dosage form.

In particular embodiments, a combination therapy includes curcumin conjugate(s) and one or more conventional treatments for the disease or disorder to be treated, such as those discussed herein.

EXAMPLES

Example 1: Synthesis of Curcumin Conjugates

Materials and Methods

Curcumin conjugates were synthesized according to the following reaction scheme and conditions:

TABLE 5

Curcumin Conjugate Synthesis Reaction Conditions

| Entry | Reaction Conditions |
|---|---|
| 1 | Step 1: BtSO$_2$Me, TEA, DMF, MW @ 70° C., 1 h |
|   | Step 2: DMAP, THF, MW @ 70° C., 2 h |
| 2 | Step 1: BtH, SOCl$_2$, THF, 20° C., 2 h |
|   | Step 2: DMAP, THF, MW @ 100° C., 2 h |
| 3 | Step 1: BtH, SOCl$_2$, THF, 20° C., 2 h |
|   | Step 2: TEA, THF, 20° C., Overnight |
| 4 | Step 1: BtH, SOCl$_2$, THF, 20° C., 2 h |
|   | Step 2: DMAP, DCM, 20° C., Overnight |
| 5 | IBCF, NMM, THF, 20° C., Overnight |
| 6 | DCC, DMAP, DCM, 20° C., Overnight |
| 7 | EDAC, DMAP, DCM, 20° C., Overnight |

In order to establish optimal reaction conditions, various coupling reagents and solvents at different temperatures were utilized.

Screened different reaction conditions for all amino acid protecting groups (Cbz and Fmoc).

Results

An efficient methodology for synthesizing various curcumin conjugates was developed. All the synthesized compounds were fully characterized by NMR and Mass spectroscopy. The purity and chiral integrity of the compounds were confirmed by optical rotation, chiral HPLC studies. All the conjugates were screened for anti-inflammatory studies and ulcerogenic liability (discussed in Example 2).

An exemplary reaction is

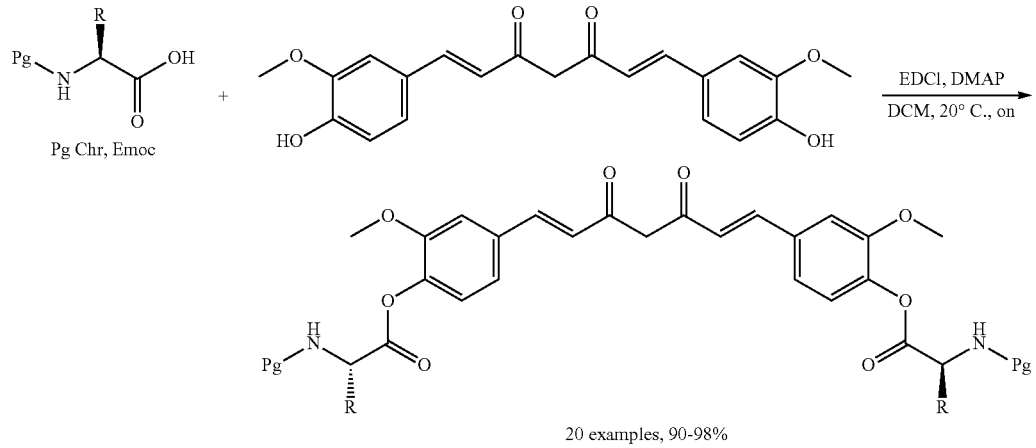

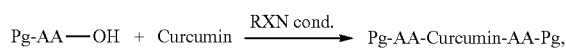

where "AA" is an amino acid,

"curcumin" is (1E,6E)-1,7-Bis(4-hydroxy-3-methoxyphenyl)hepta-1,6-diene-3,5-dione, and "Pg" is an amino acid protecting group.

Several protected amino acid-curcumin conjugates were synthesized using 1-ethyl-3-(3-dimethylaminopropyl)carbodiimide (EDAC) as a coupling reagent in dimethylaminopyridine (DMAP) in dichloromethane (DCM) at room temperature.

wherein "R" is an amino acid side group, and "Pg" and amino acid-protecting group.

Theoretically and experimentally calculated the Log P and Log S values.

The calculated Log P and log S values are varied with respect to protecting groups and amino acids.

TABLE 6

Log P and log S values

| Entry | Compound | Log P | Log S |
|---|---|---|---|
| 1 | Curcumin | 3.62 | −4.81 |
| 2 | Cbz-Gly-Curcumin-Gly-Cbz | 4.41 | −6.98 |

TABLE 6-continued

Log P and log S values

| Entry | Compound | Log P | Log S |
|---|---|---|---|
| 3 | Fmoc-Gly-Curcumin-Gly-Fmoc | 6.03 | −7.46 |
| 4 | Cbz-Ala-Curcumin-Ala-Cbz | 4.84 | −6.88 |
| 5 | Fmoc-Ala-Curcumin-Ala-Fmoc | 6.22 | −7.43 |
| 6 | Cbz-Met-Curcumin-Met-Cbz | 5.41 | −7.05 |
| 7 | Fmoc-Met-Curcumin-Met-Fmoc | 6.90 | −7.54 |

Synthesized several curcuminamino acid conjugates were in excellent yield with retention of chirality.

References: Perrone, *Exp. Ther. Med.*, 2015, 10, 1615-1623; Salem, *RSV Adv.*, 2014, 4, 10815-10829; Panda, et al., *Bioorg. Med. Chem. Lett.*, 2015, 25, 3816-3821; and Panda, et al., *Aldrichimica Acta*, 2013, 46, 43-55.

Example 2: Curcumin Conjugates are Anti-Inflammatory

Materials and Methods

Anti-Inflammatory Activity Screening

The anti-inflammatory activity of the tested compounds was determined in vivo by the acute carrageenan induced paw edema standard method in rats. See, Naumov, et al., *Bioorg. Med. Chem. Lett*, 25: 2314-2320 (2015), Tiwari, et al., *Org. Biomol. Chem*, 12: 7238-7249 (2014), Girgis, et al., *Eur. J. Med. Chem*, 50: 1-8 (2012), Barsoum, et al., *Eur. J. Med. Chem*, 44: 2172-2177 (2009), Girgis, et al., *Eur. J. Med. Chem*, 44: 1972-1977 (2009), Girgis, et al., *Eur. J. Med. Chem*, 44: 1257-1264 (2009), Girgis, et al., *Eur. J. Med. Chem*, 44: 91-100 (2009), Girgis, et al., *Eur. J. Med. Chem*, 43: 2116-2121 (2008), Girgis, et al., *Bioorg. Med. Chem*, 14: 8527-8532 (2006), and Barsoum, et al., *Bioorg. Med. Chem*, 14: 3929-3937 (2006).

Adult Wister rats of either sex (pregnant female animals were excluded) weighing 120-150 g were divided into 18 groups of 6 animals each. Administration of the tested compounds dissolved in DMSO, at a dose of 10 mg kg$^{-1}$ (rat body weight) indomethacin mol equivalent, was given intraperitoneally 1 h before induction of inflammation. The control group was given DMSO only. Carrageenan paw edema was induced by subcutaneous injection of freshly prepared 1% solution of carrageenan in saline (0.9%, 0.1 ml per rat) into subplantar tissue of the right hind paw of rats. The thickness of the paw was measured (in mm) after successive time intervals (1, 2,3,4 and 24 h) and compared with the initial hind paw thickness of each rat for determining the edema thickness. Data were collected, checked, revised and analyzed. Quantitative variables from normal distribution were expressed as means±SE "standard error". The anti-inflammatory activity was expressed as percentage inhibition of edema thickness in treated animals in comparison with the control group according to eqn. (1) (Table 7, FIGS. 2-4).

$$\% \text{ Inhibition of edema} = \frac{V_c - V_t}{V_c} \times 100 \quad (1)$$

Where, $V_c$ and $V_t$ are the mean of edema paw thickness for the control and tested compound treated animal groups, respectively.

Potency of the tested compounds was expressed as % inhibition of edema for the tested compounds relative to % inhibition of edema for indomethacin "reference standard" at 4 h effect according to equation (2).

$$\text{Potency} = (\% \text{ inhibition of edema for the tested compound treated group})/(\% \text{ inhibition of edema for indomethacin treated group}) \quad (2)$$

Results

The anti-inflammatory properties of the synthesized curcumin-amino acid conjugates were determined by the standard method of acute carrageenan induced paw edema in rats at a dose of 10 mg kg$^{-1}$ (rat body weight) indomethacin mol equivalent (reference standard—see citations in Materials and Methods above).

Figure 2:
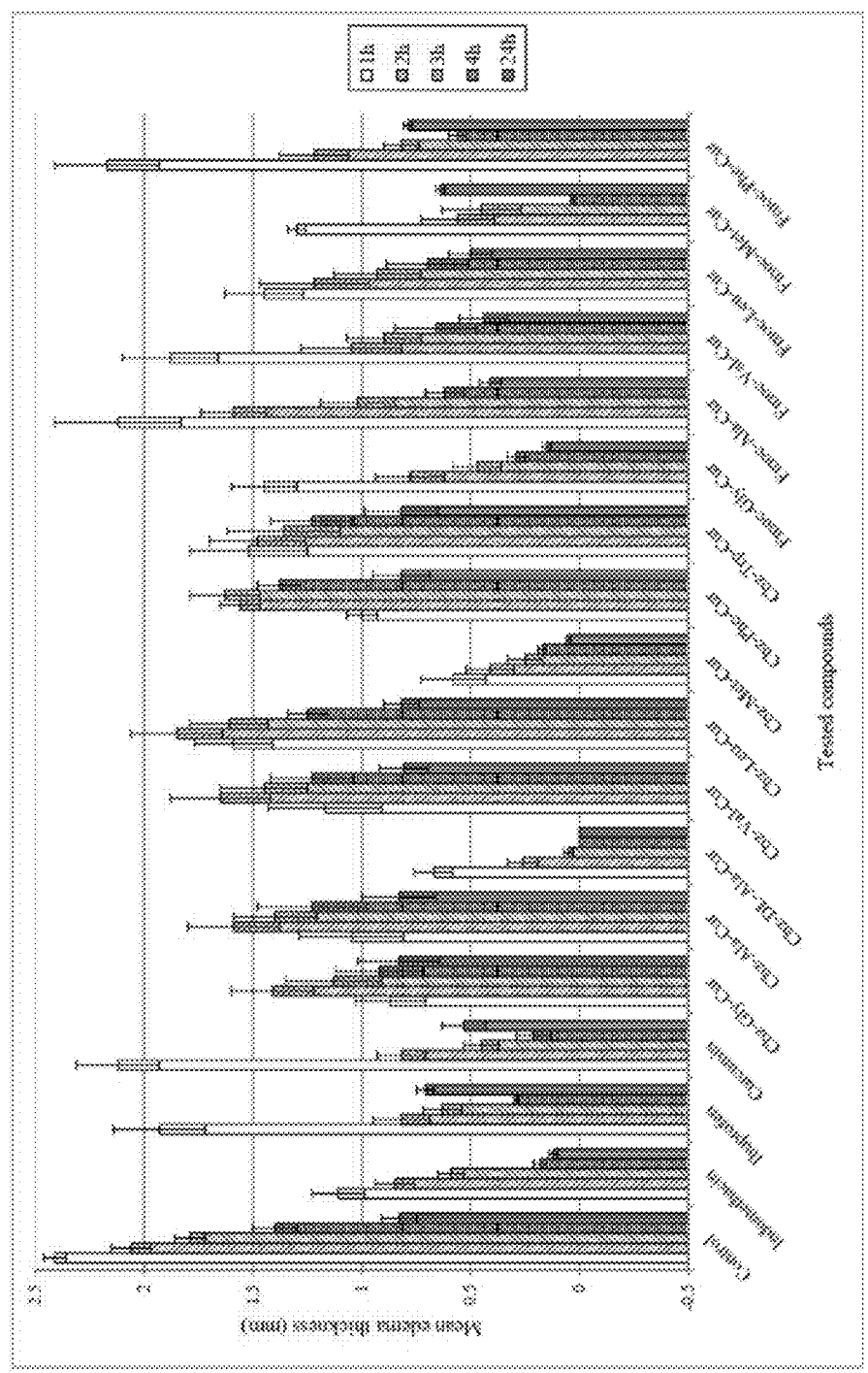
FIG. 2 is a bar graph showing mean edema thickness (mm) of the tested compounds at successive time intervals.
Figure 3:
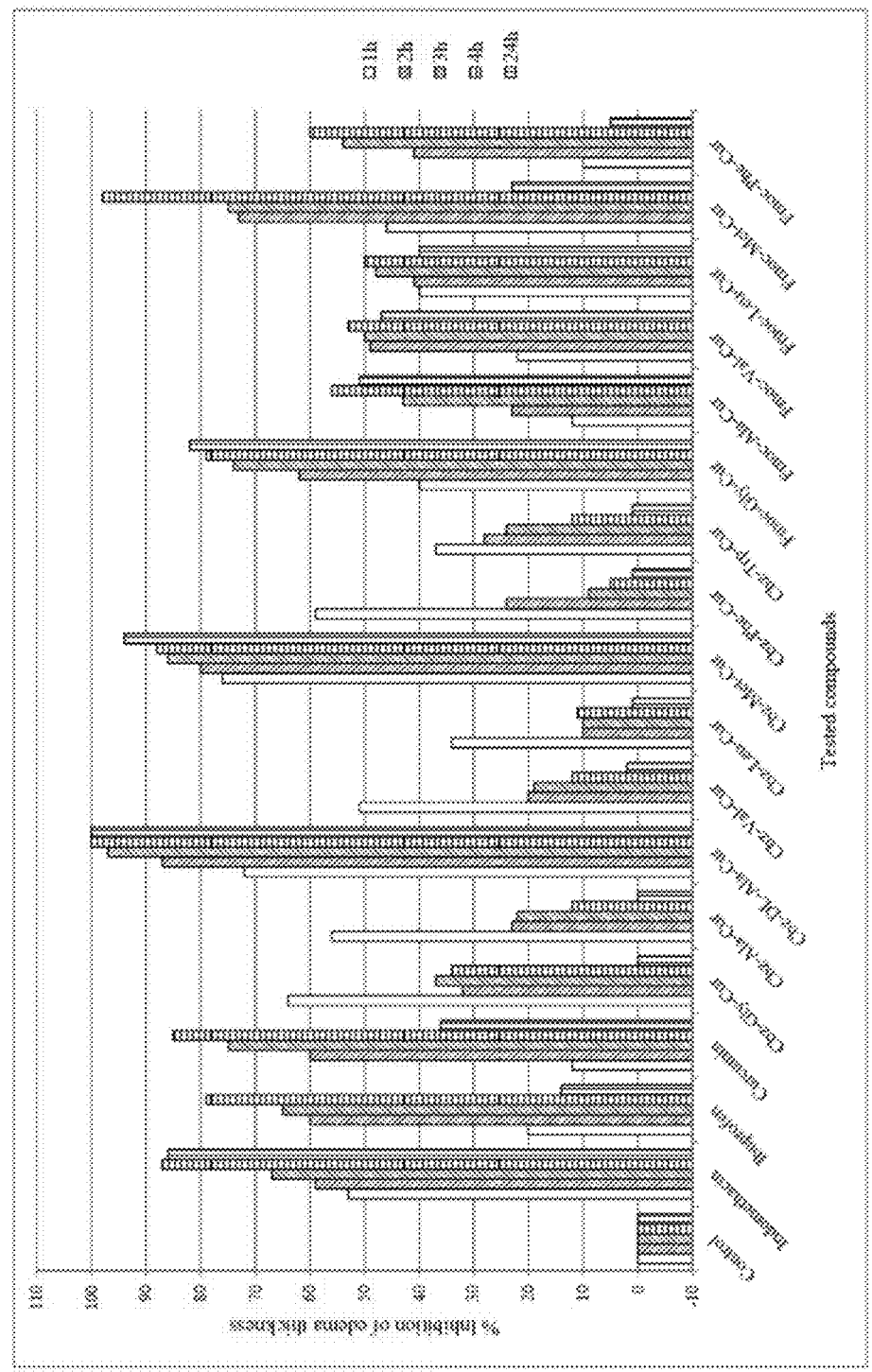
FIG. 3 is a bar graph showing % inhibition of edema for tested compounds.
Figure 4:
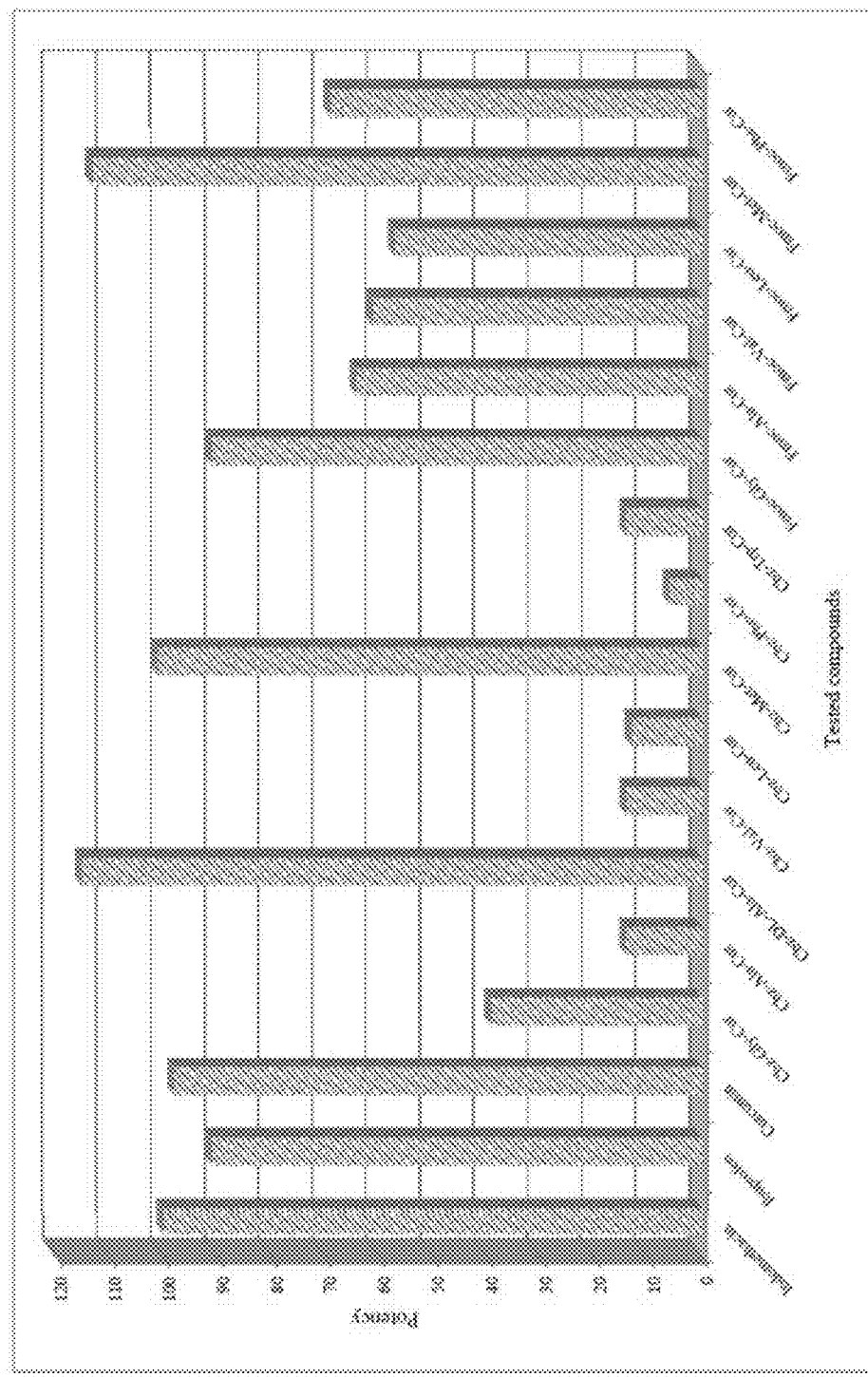
FIG. 4 is a bar graph showing anti-inflammatory potency of tested compounds.

The results in Table 7, FIGS. 2-4 show that the following synthesized conjugates: Cbz-DL-Ala-Cur, Cbz-Met-Cur, Fmoc-Met-Cur, Z-D-Ala-Cur, Z-D-Met-Cur, Boc-L-Met-Cur, Boc-D-Met-Cur, HCl-Gly-Cur, HCl-D-Ala-Cur, HCl-β-Ala-Cur, HCl-L-Met-Cur, and HCl-D-Met-Cur [potency (% inhibition of edema for the tested compounds relative to that of indomethacin "reference standard" at 4 h effect)=115, 101, 113, 115, 108, 101, 102, 101, 110, 102, 111, 113, respectively] exhibited promising anti-inflammatory properties with potency higher than that of indomethacin (standard reference used exhibiting higher potency than that of ibuprofen). Compound Fmoc-Gly-Cur reveals anti-inflammatory activity comparable to that of ibuprofen (potency=91). Structure-activity relationships (SAR) based on the observed results reveal that.

1. The Fmoc seems more favorable than the Cbz for developing anti-inflammatory active conjugates.

2. Methionine is superior relative to all the amino acid type used for developing high bio-properties.

3. Utilization of glycine seems a good choice for developing anti-inflammatory active agents compared with other amino acid possessing alkyl substitution at the α-carbon (alanine, valine, leucine).

4. Compound with DL-Ala function reveals enhanced anti-inflammatory properties than the corresponding analogue with L-Ala.

TABLE 7
Bio-assay results for the tested compounds at 10 mg kg$^{-1}$ (rat body weight) indomethacin mol equivalent.
| ID | Compd. |
|---|---|
| 1 | Control |
| 2 | 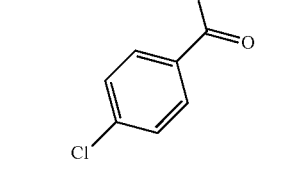 Indomethacin |
| 3 | 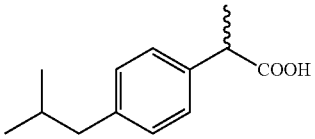 Ibuprofen |
| 4 | 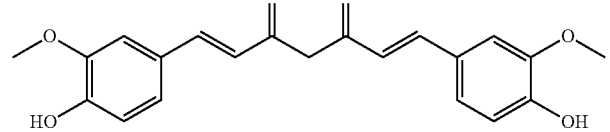 Curcumin |
| 5 | 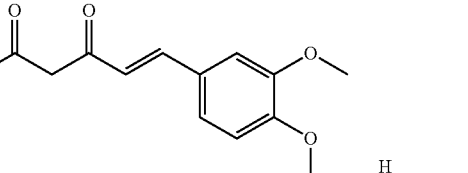 Cbz-Gly-Cur |
| 6 |  Cbz-Ala-Cur |

TABLE 7-continued
7
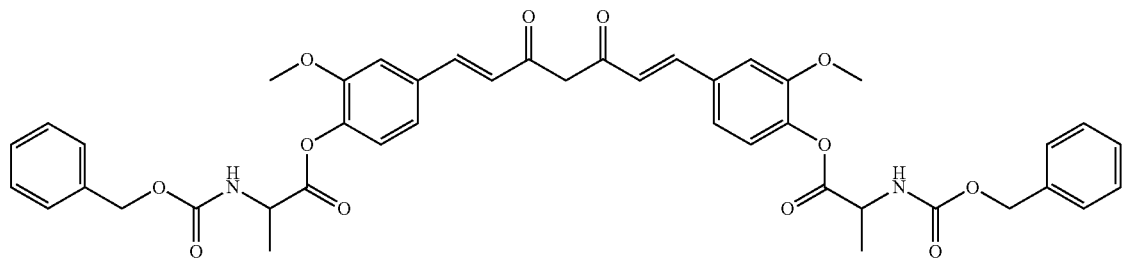
Cbz-DL-Ala-Cur
8
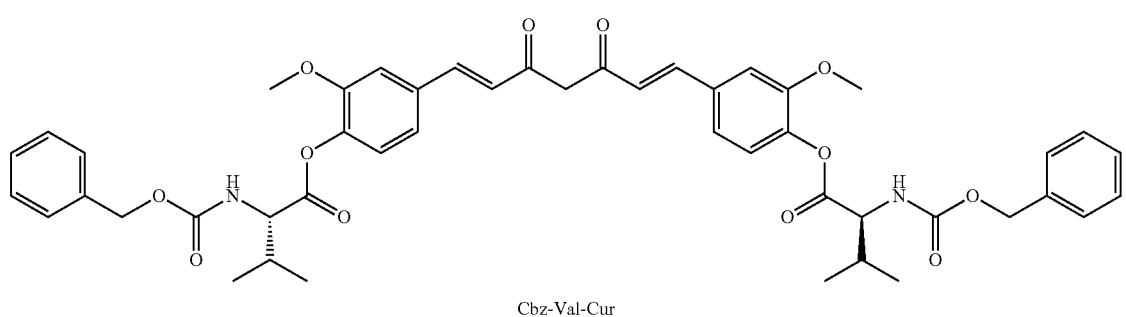 [SMILES: COc1cc(/C=C/C(=O)CC(=O)/C=C/c2ccc(OC(=O)[C@@H](NC(=O)OCc3ccccc3)C(C)C)c(OC)c2)ccc1OC(=O)[C@@H](NC(=O)OCc1ccccc1)C(C)C]
Cbz-Val-Cur
9
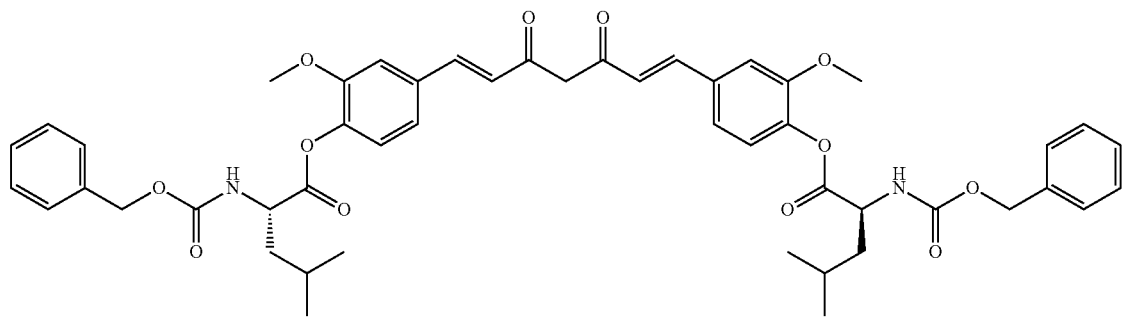
Cbz-Leu-Cur
10
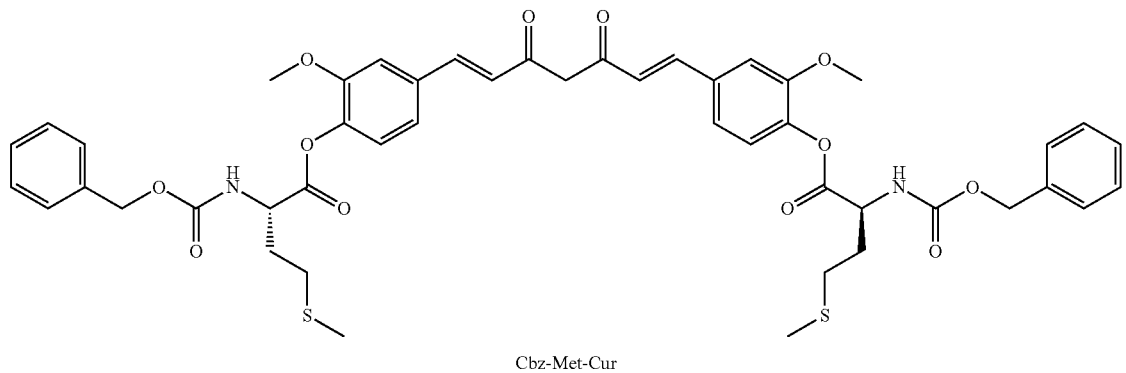 [SMILES: COc1cc(/C=C/C(=O)CC(=O)/C=C/c2ccc(OC(=O)[C@H](CCSC)NC(=O)OCc3ccccc3)c(OC)c2)ccc1OC(=O)[C@H](CCSC)NC(=O)OCc1ccccc1]
Cbz-Met-Cur TABLE 7-continued
| 11 | 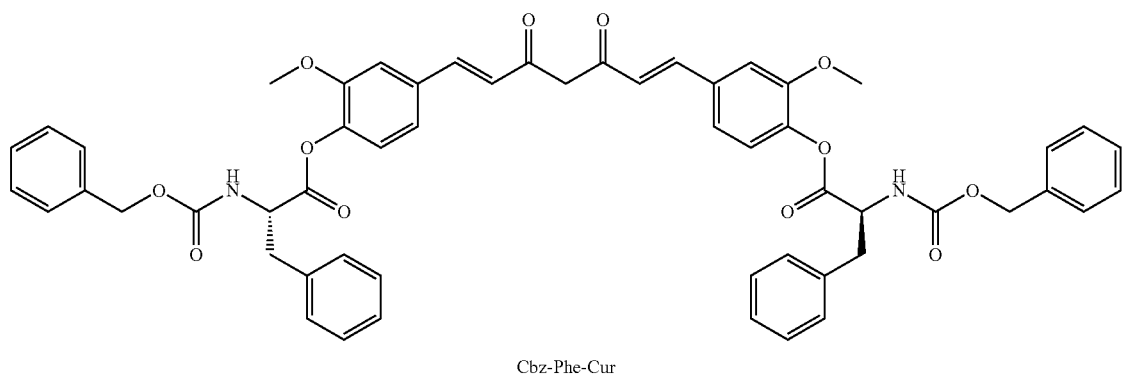 [SMILES: COc1cc(/C=C/C(=O)CC(=O)/C=C/c2ccc(OC(=O)[C@H](Cc3ccccc3)NC(=O)OCc3ccccc3)c(OC)c2)ccc1OC(=O)[C@H](Cc1ccccc1)NC(=O)OCc1ccccc1] |
|----|----------------------|
Cbz-Phe-Cur
| 12 | 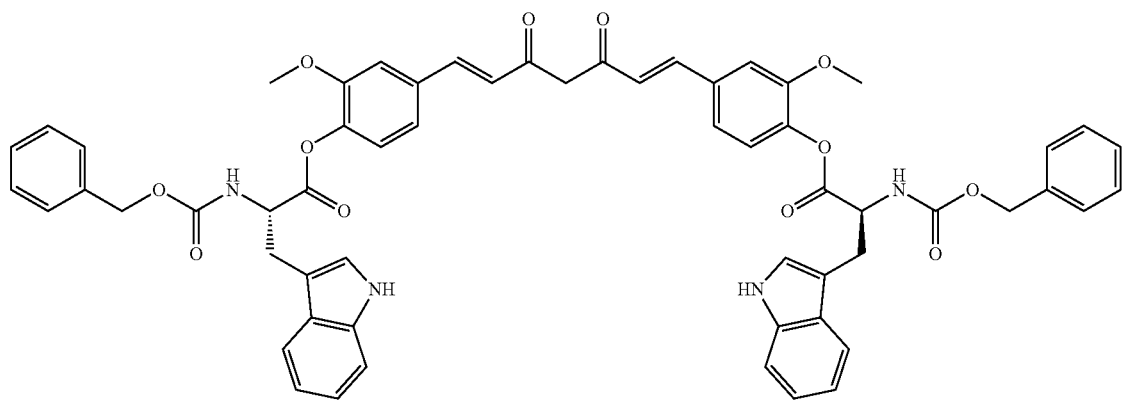 |
|----|----------------------|
Cbz-Trp-Cur
| 13 | 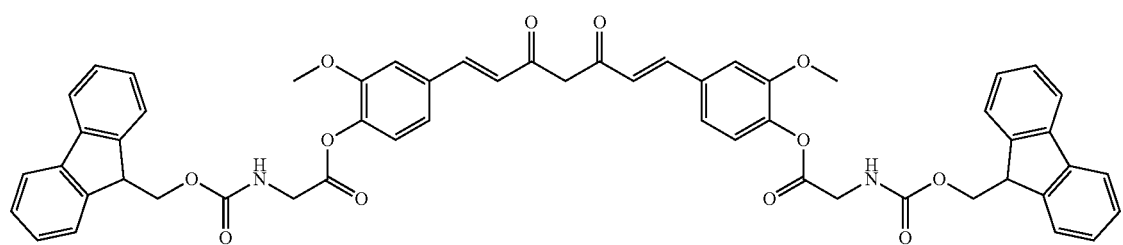 |
|----|----------------------|
Fmoc-Gly-Cur
| 14 | 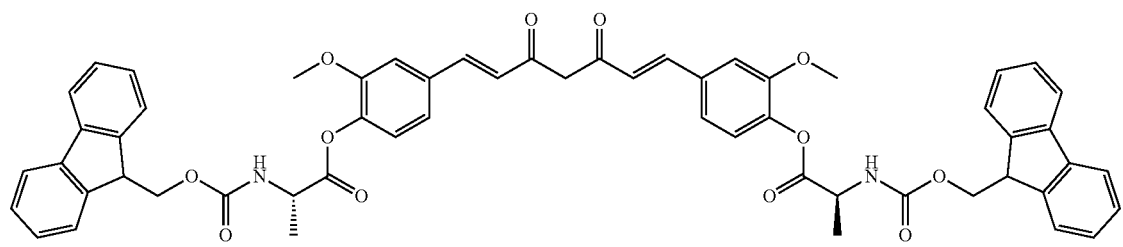 |
|----|----------------------|
Fmoc-Ala-Cur TABLE 7-continued
15
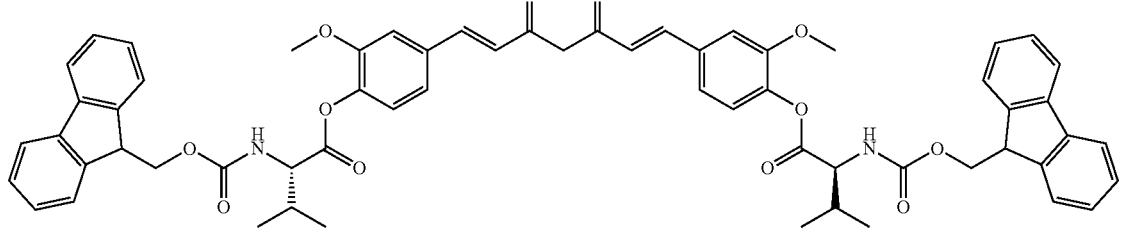
Fmoc-Val-Cur
16
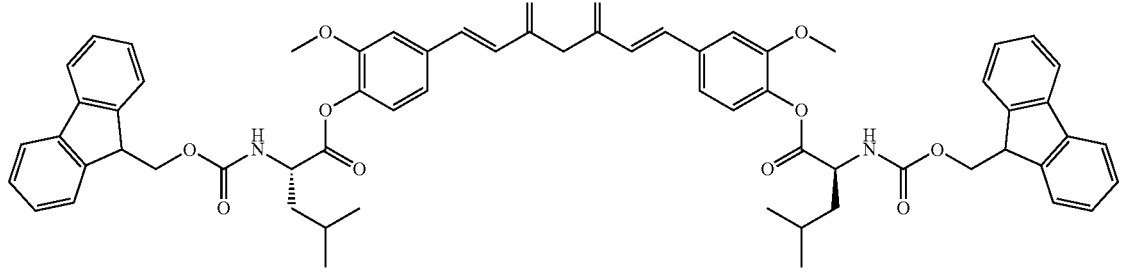
Fmoc-Leu-Cur
17
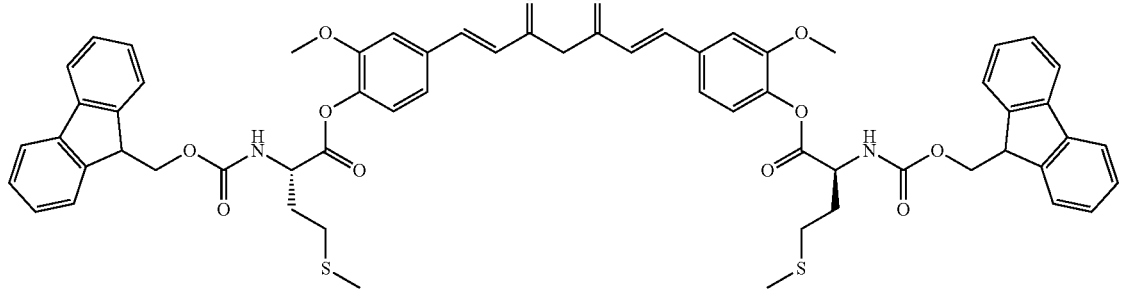
Fmoc-Met-Cur
18
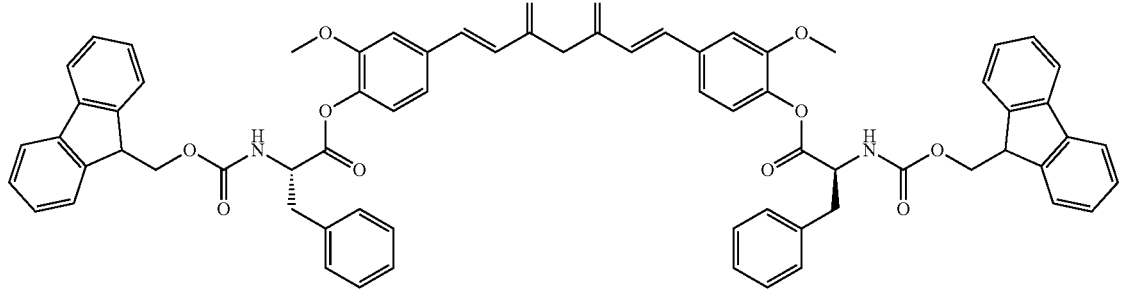
Fmoc-Phe-Cur
19
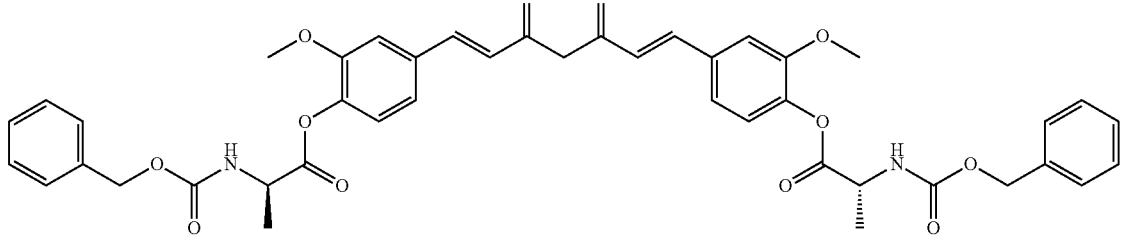
Z-D-Ala-Cur TABLE 7-continued
20
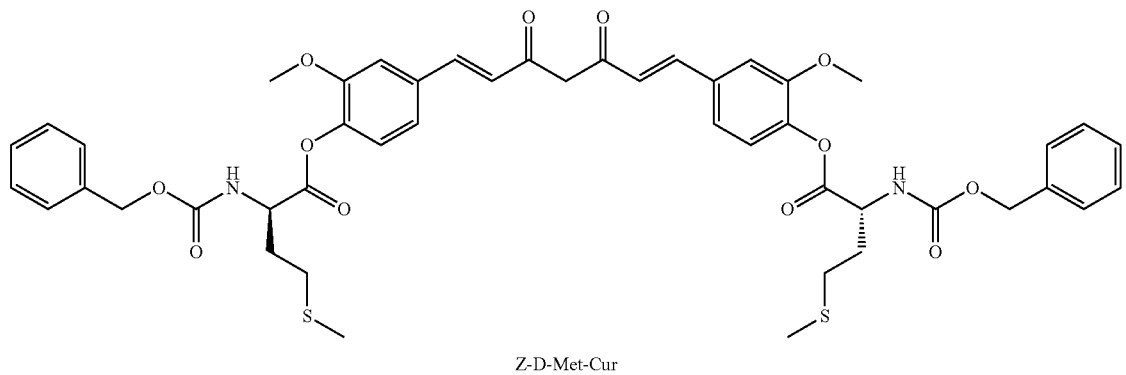 [SMILES: COc1cc(/C=C/C(=O)CC(=O)/C=C/c2ccc(OC(=O)[C@@H](CCSC)NC(=O)OCc3ccccc3)c(OC)c2)ccc1OC(=O)[C@@H](CCSC)NC(=O)OCc1ccccc1]
Z-D-Met-Cur
21
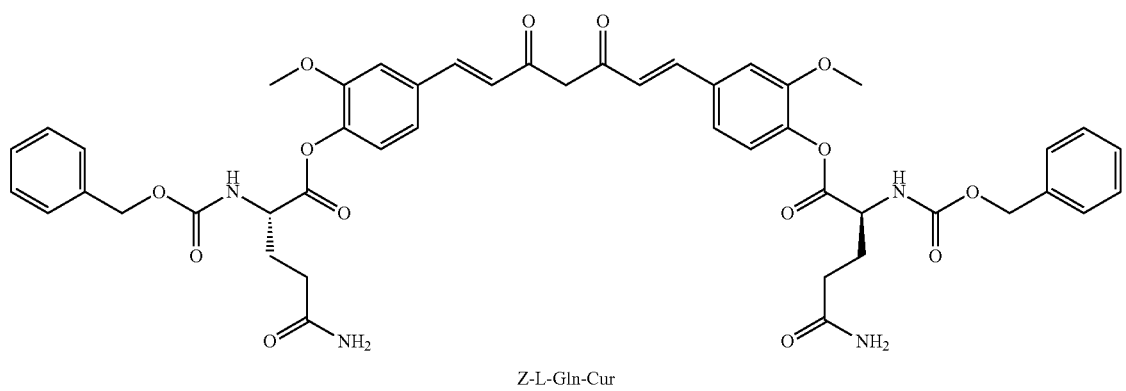 [SMILES: COc1cc(/C=C/C(=O)CC(=O)/C=C/c2ccc(OC(=O)[C@H](CCC(N)=O)NC(=O)OCc3ccccc3)c(OC)c2)ccc1OC(=O)[C@H](CCC(N)=O)NC(=O)OCc1ccccc1]
Z-L-Gln-Cur
22
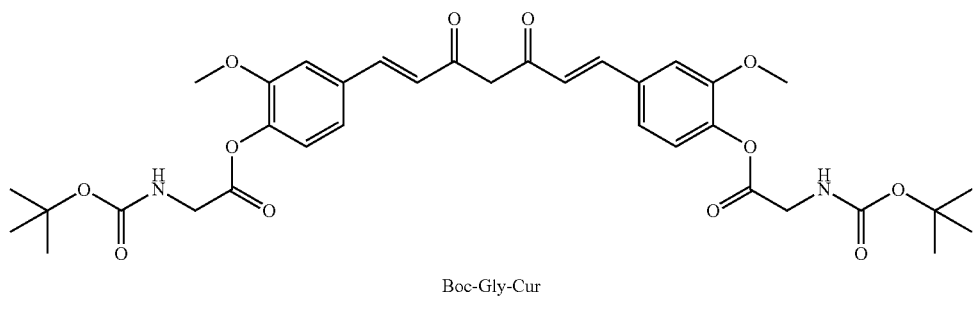 [SMILES: COc1cc(/C=C/C(=O)CC(=O)/C=C/c2ccc(OC(=O)CNC(=O)OC(C)(C)C)c(OC)c2)ccc1OC(=O)CNC(=O)OC(C)(C)C]
Boc-Gly-Cur
23
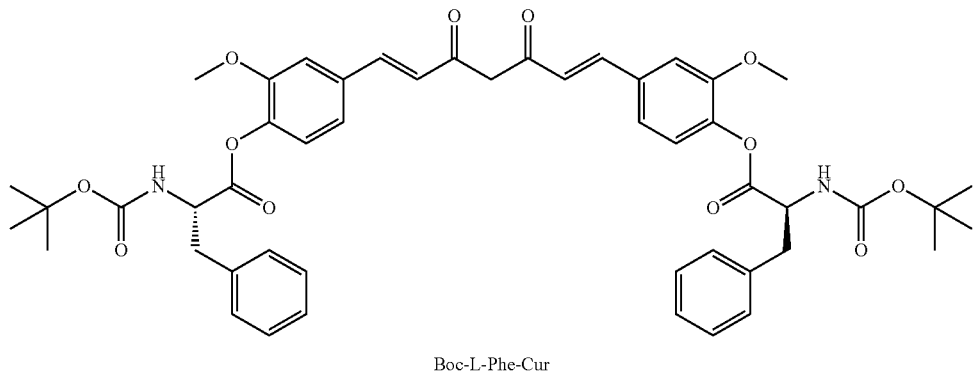 [SMILES: COc1cc(/C=C/C(=O)CC(=O)/C=C/c2ccc(OC(=O)[C@H](Cc3ccccc3)NC(=O)OC(C)(C)C)c(OC)c2)ccc1OC(=O)[C@H](Cc1ccccc1)NC(=O)OC(C)(C)C]
Boc-L-Phe-Cur TABLE 7-continued
24
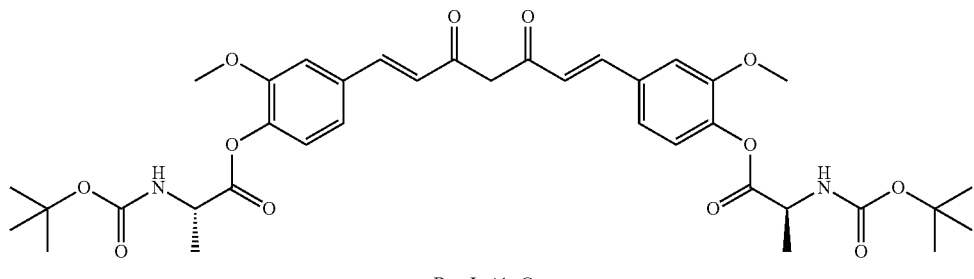
Boc-L-Ala-Cur
25
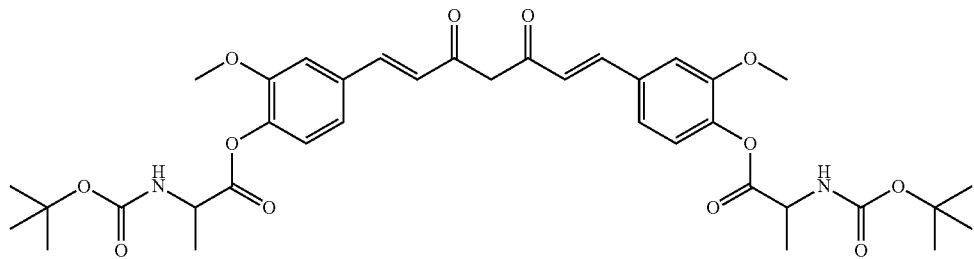
Boc-DL-Ala-Cur
26
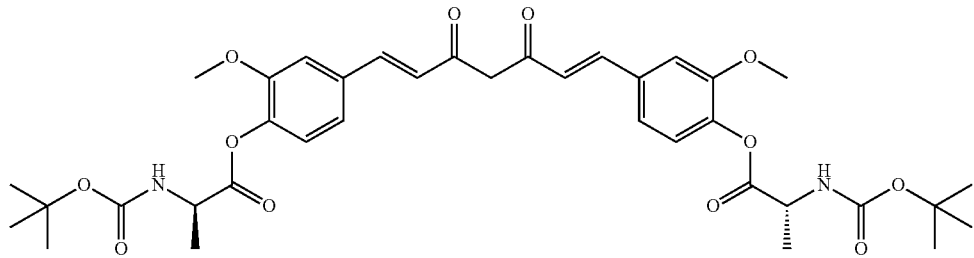
Boc-D-Ala-Cur
27
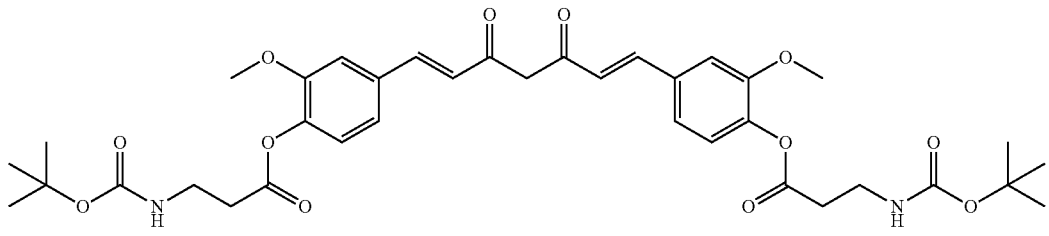
Boc-β-Ala-Cur
28
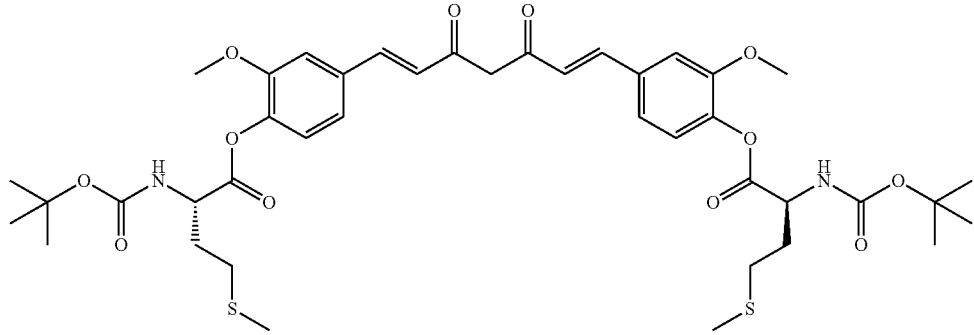
Boc-L-Met-Cur TABLE 7-continued
29
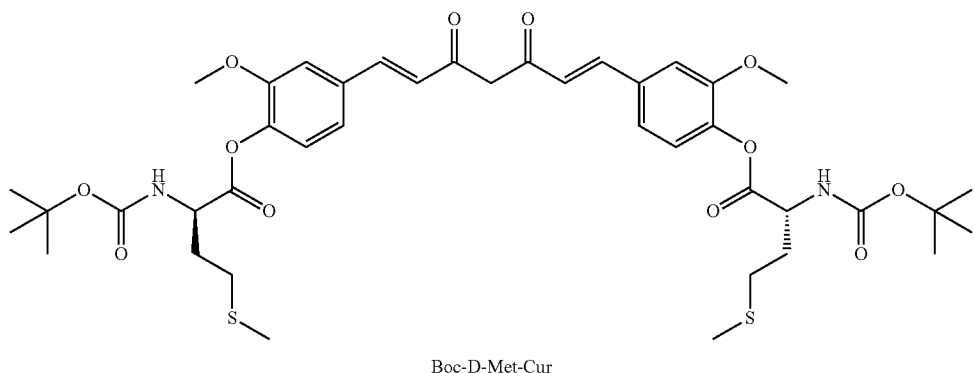 [SMILES: COc1cc(/C=C/C(=O)CC(=O)/C=C/c2ccc(OC(=O)[C@@H](CCSC)NC(=O)OC(C)(C)C)c(OC)c2)ccc1OC(=O)[C@@H](CCSC)NC(=O)OC(C)(C)C]
Boc-D-Met-Cur
30
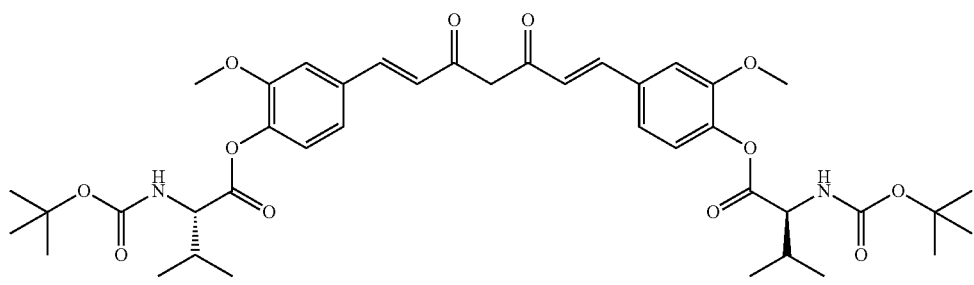
Boc-L-Val-Cur
31
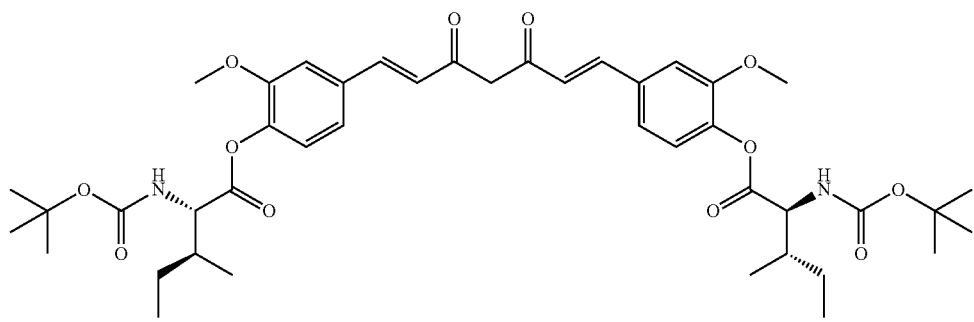
Boc-L-Ile-Cur
32
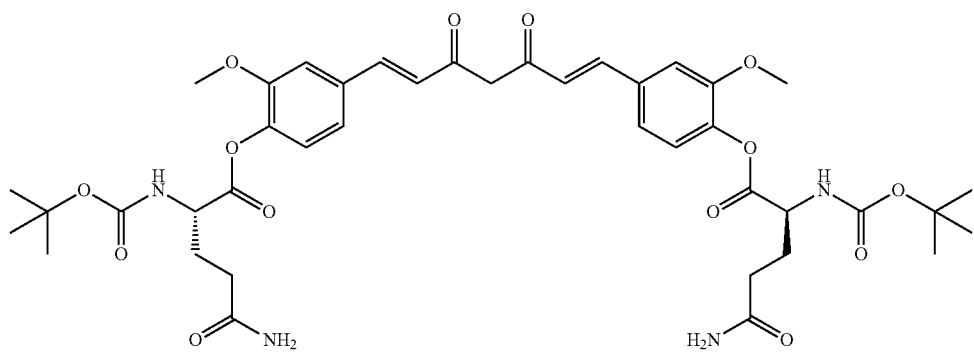
Boc-L-Gln-Cur TABLE 7-continued
33 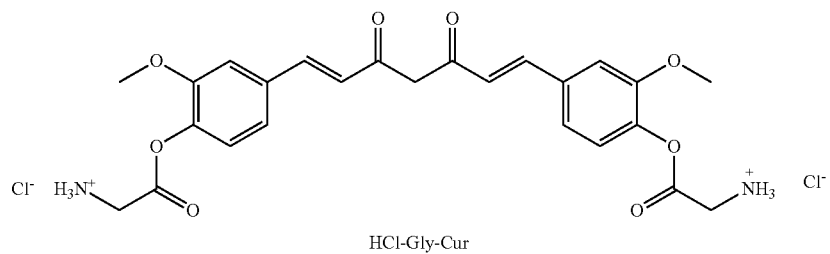 [SMILES: [Cl-] ; COc1cc(/C=C/C(=O)CC(=O)/C=C/c2ccc(OC(=O)C[NH3+])c(OC)c2)ccc1OC(=O)CN ; [Cl-]]
HCl-Gly-Cur
34 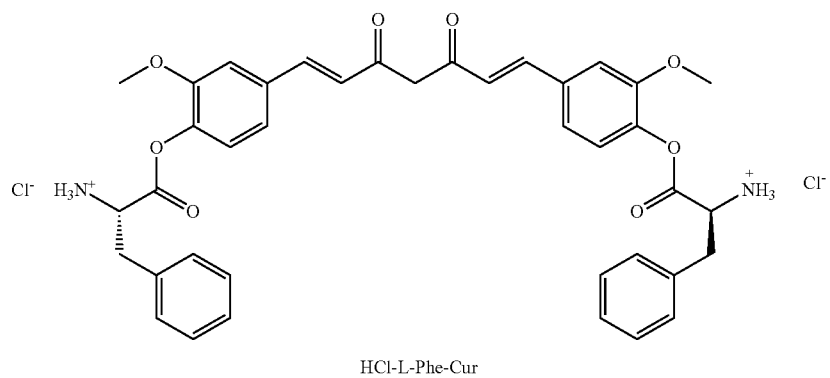 [SMILES: [Cl-] ; COc1cc(/C=C/C(=O)CC(=O)/C=C/c2ccc(OC(=O)[C@@H]([NH3+])Cc3ccccc3)c(OC)c2)ccc1OC(=O)[C@@H](N)Cc1ccccc1 ; [Cl-]]
HCl-L-Phe-Cur
35 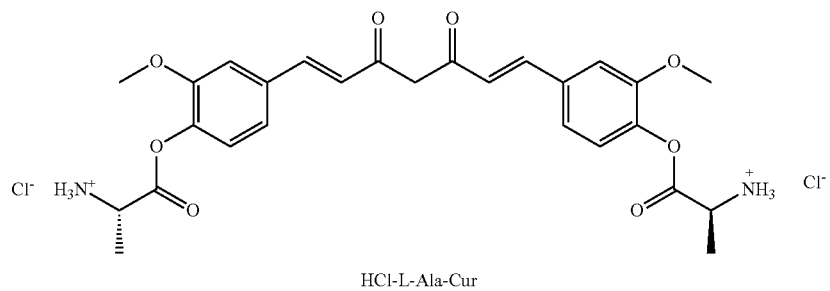 [SMILES: [Cl-] ; COc1cc(/C=C/C(=O)CC(=O)/C=C/c2ccc(OC(=O)[C@H](C)[NH3+])c(OC)c2)ccc1OC(=O)[C@H](C)N ; [Cl-]]
HCl-L-Ala-Cur
36 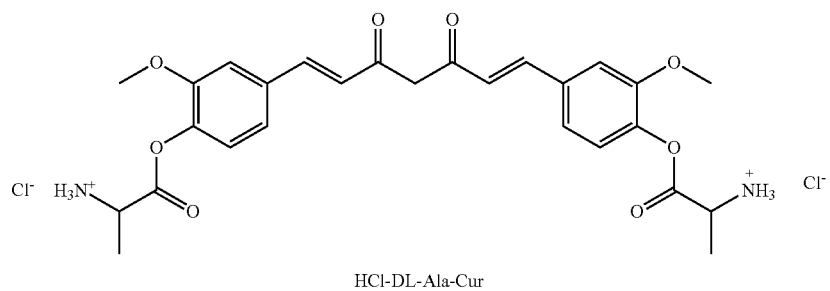 [SMILES: [Cl-] ; COc1cc(/C=C/C(=O)CC(=O)/C=C/c2ccc(OC(=O)C(C)[NH3+])c(OC)c2)ccc1OC(=O)C(C)N ; [Cl-]]
HCl-DL-Ala-Cur
37 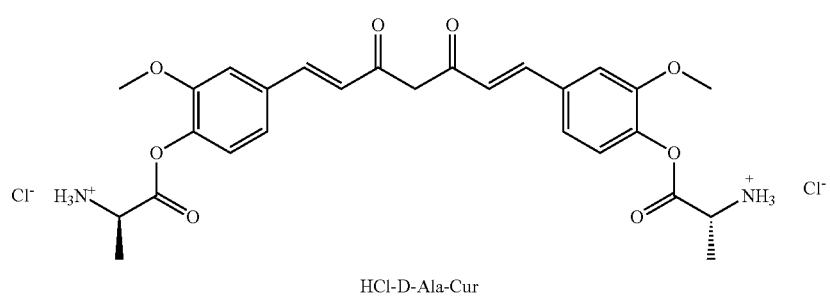 [SMILES: [Cl-] ; COc1cc(/C=C/C(=O)CC(=O)/C=C/c2ccc(OC(=O)[C@@H](C)[NH3+])c(OC)c2)ccc1OC(=O)[C@@H](C)N ; [Cl-]]
HCl-D-Ala-Cur TABLE 7-continued
38
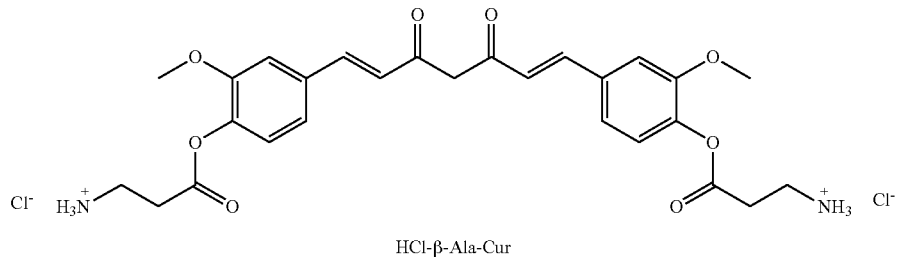 [SMILES: [Cl-] ; COc1cc(/C=C/C(=O)CC(=O)/C=C/c2ccc(OC(=O)CCN)c(OC)c2)ccc1OC(=O)CCN ; [Cl-]]
HCl-β-Ala-Cur
39
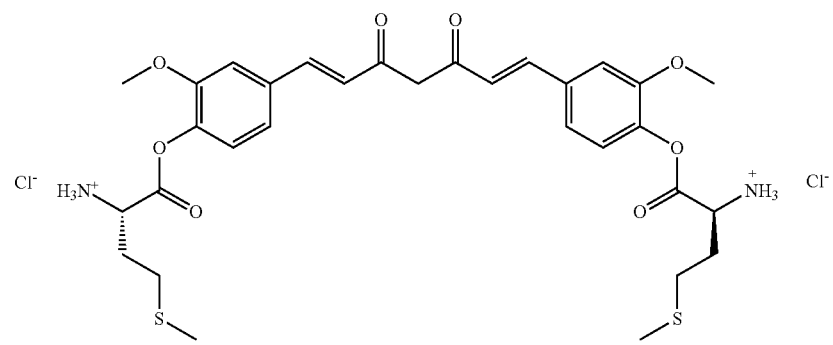
HCl-L-Met-Cur
40
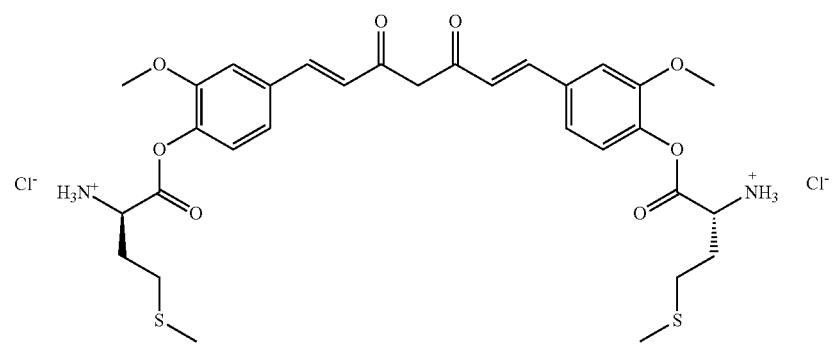
HCl-D-Met-Cur
41
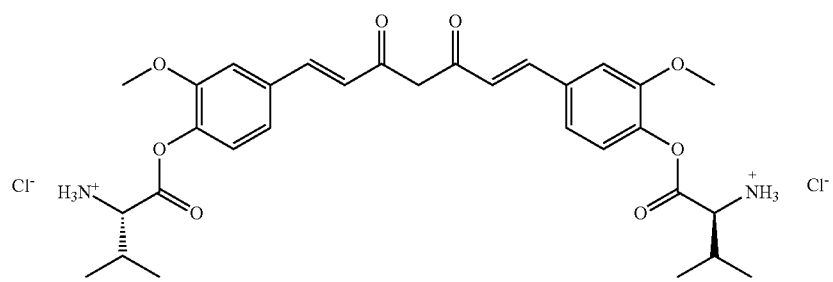
HCl-L-Val-Cur TABLE 7-continued
42
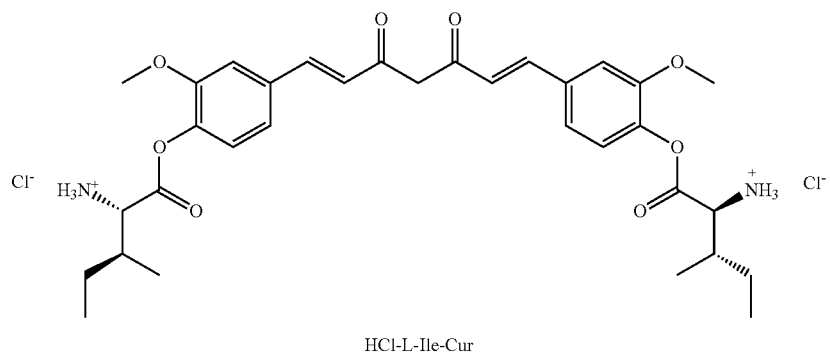 [SMILES: [Cl-] ; CC[C@H](C)[C@H](N)C(=O)Oc1ccc(/C=C/C(=O)CC(=O)/C=C/c2ccc(OC(=O)[C@@H]([NH3+])[C@@H](C)CC)c(OC)c2)cc1OC ; [Cl-]]
HCl-L-Ile-Cur
43
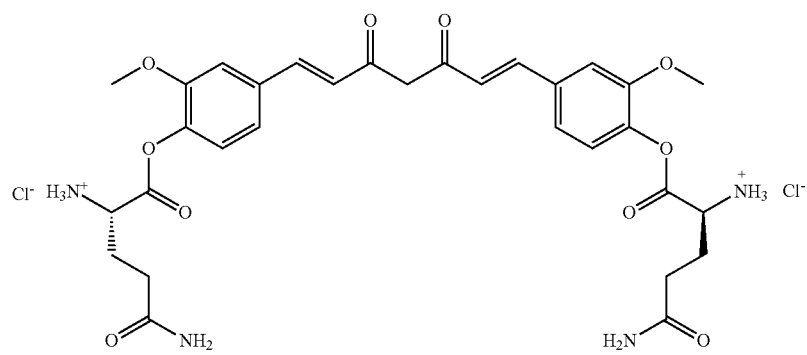
HCl-L-Gln-Cur
| | Mean edema thickness "mm" (% inhibition of edema) | | | | | |
|---|---|---|---|---|---|---|
| ID | 1 h | 2 h | 3 h | 4 h | 24 h | Potency[a] |
| 1 | 2.41 ± 0.05 (0.00) | 2.06 ± 0.09 (0.00) | 1.79 ± 0.07 (0.00) | 1.40 ± 0.10 (0.00) | 0.83 ± 0.08 (0.00) | — |
| 2 | 1.11 ± 0.12 (53) | 0.85 ± 0.09 (59) | 0.59 ± 0.06 (67) | 0.18 ± 0.03 (87) | 0.12 ± 0.02 (86) | 100 |
| 3 | 1.93 ± 0.21 (20) | 0.82 ± 0.13 (60) | 0.63 ± 0.09 (65) | 0.29 ± 0.01 (79) | 0.71 ± 0.04 (14) | 91 |
| 4 | 2.12 ± 0.19 (12) | 0.82 ± 0.11 (60) | 0.45 ± 0.08 (75) | 0.21 ± 0.08 (85) | 0.53 ± 0.10 (36) | 98 |
| 5 | 0.87 ± 0.16 (64) | 1.41 ± 0.19 (32) | 1.13 ± 0.22 (37) | 0.92 ± 0.20 (34) | 0.83 ± 0.19 (0) | 39 |
| 6 | 1.05 ± 0.24 (56) | 1.59 ± 0.21 (23) | 1.40 ± 0.19 (22) | 1.23 ± 0.25 (12) | 0.83 ± 0.17 (0) | 14 |
| 7 | 0.67 ± 0.09 (72) | 0.26 ± 0.07 (87) | 0.05 ± 0.02 (97) | 0.00 ± 0.00 (100) | 0.00 ± 0.00 (100) | 115 |
| 8 | 1.17 ± 0.26 (51) | 1.65 ± 0.23 (20) | 1.45 ± 0.20 (19) | 1.23 ± 0.19 (12) | 0.81 ± 0.11 (2) | 14 |
| 9 | 1.59 ± 0.18 (34) | 1.85 ± 0.21 (10) | 1.61 ± 0.18 (10) | 1.25 ± 0.09 (11) | 0.82 ± 0.08 (1) | 13 |
| 10 | 0.58 ± 0.15 (76) | 0.41 ± 0.11 (80) | 0.25 ± 0.08 (86) | 0.17 ± 0.02 (88) | 0.05 ± 0.01 (94) | 101 |
| 11 | 1.00 ± 0.07 (59) | 1.56 ± 0.09 (24) | 1.63 ± 0.16 (9) | 1.38 ± 0.10 (5) | 0.82 ± 0.13 (1) | 6 |
| 12 | 1.52 ± 0.27 (37) | 1.48 ± 0.22 (28) | 1.36 ± 0.26 (24) | 1.23 ± 0.19 (12) | 0.82 ± 0.17 (1) | 14 |
| 13 | 1.45 ± 0.15 (40) | 0.78 ± 0.16 (62) | 0.47 ± 0.11 (74) | 0.29 ± 0.04 (79) | 0.15 ± 0.02 (82) | 91 |
| 14 | 2.12 ± 0.29 (12) | 1.59 ± 0.15 (23) | 1.02 ± 0.17 (43) | 0.62 ± 0.09 (56) | 0.41 ± 0.05 (51) | 64 |
| 15 | 1.88 ± 0.22 (22) | 1.05 ± 0.23 (49) | 0.90 ± 0.17 (50) | 0.66 ± 0.19 (53) | 0.44 ± 0.11 (47) | 61 |
| 16 | 1.45 ± 0.18 (40) | 1.22 ± 0.25 (41) | 0.93 ± 0.20 (48) | 0.70 ± 0.19 (50) | 0.50 ± 0.10 (40) | 57 |
| 17 | 1.30 ± 0.04 (46) | 0.56 ± 0.17 (73) | 0.45 ± 0.18 (75) | 0.03 ± 0.01 (98) | 0.64 ± 0.02 (23) | 113 |
| 18 | 2.17 ± 0.24 (10) | 1.22 ± 0.16 (41) | 0.82 ± 0.08 (54) | 0.56 ± 0.04 (60) | 0.79 ± 0.02 (5) | 69 |
| 19 | 0.43 ± 0.08 (82) | 0.23 ± 0.04 (89) | 0.09 ± 0.03 (95) | 0.00 ± 0.00 (100) | 0.42 ± 0.06 (49) | 115 |
| 20 | 0.51 ± 0.04 (79) | 0.41 ± 0.03 (80) | 0.27 ± 0.01 (85) | 0.08 ± 0.02 (94) | 0.08 ± 0.01 (90) | 108 |
| 21 | 1.18 ± 0.11 (51) | 1.09 ± 0.19 (47) | 0.99 ± 0.09 (45) | 0.78 ± 0.10 (44) | 0.80 ± 0.05 (4) | 51 |
| 22 | 1.37 ± 0.18 (43) | 1.16 ± 0.14 (44) | 1.00 ± 0.11 (44) | 0.73 ± 0.09 (48) | 0.44 ± 0.05 (47) | 55 |
| 23 | 1.47 ± 0.16 (39) | 1.16 ± 0.09 (44) | 0.85 ± 0.11 (53) | 0.58 ± 0.03 (59) | 0.41 ± 0.02 (51) | 68 |
| 24 | 2.26 ± 0.20 (6) | 1.84 ± 0.17 (11) | 1.44 ± 0.14 (20) | 1.04 ± 0.18 (28) | 0.79 ± 0.17 (5) | 32 |
| 25 | 2.15 ± 0.14 (11) | 1.74 ± 0.18 (16) | 1.34 ± 0.20 (25) | 0.84 ± 0.12 (40) | 0.59 ± 0.09 (29) | 46 |
| 26 | 1.87 ± 0.13 (22) | 1.46 ± 0.21 (29) | 1.09 ± 0.11 (39) | 0.81 ± 0.08 (42) | 0.52 ± 0.05 (37) | 48 |
| 27 | 1.66 ± 0.19 (31) | 1.38 ± 0.11 (33) | 0.99 ± 0.12 (45) | 0.55 ± 0.07 (61) | 0.60 ± 0.03 (28) | 70 |
| 28 | 1.59 ± 0.21 (34) | 1.31 ± 0.18 (36) | 1.01 ± 0.17 (44) | 0.17 ± 0.02 (88) | 0.64 ± 0.05 (23) | 101 |
| 29 | 1.01 ± 0.14 (58) | 0.63 ± 0.11 (69) | 0.47 ± 0.08 (74) | 0.15 ± 0.06 (89) | 0.49 ± 0.09 (41) | 102 |
| 30 | 2.09 ± 0.21 (13) | 1.57 ± 0.19 (24) | 1.34 ± 0.11 (25) | 0.80 ± 0.08 (43) | 0.58 ± 0.10 (30) | 49 |
| 31 | 1.61 ± 0.11 (33) | 1.27 ± 0.07 (38) | 0.91 ± 0.05 (49) | 0.69 ± 0.02 (51) | 0.49 ± 0.03 (41) | 59 |
| 32 | 2.16 ± 0.17 (10) | 1.73 ± 0.09 (16) | 1.22 ± 0.12 (32) | 0.83 ± 0.06 (41) | 0.36 ± 0.02 (57) | 47 |
| 33 | 0.82 ± 0.09 (66) | 0.69 ± 0.03 (67) | 0.46 ± 0.03 (74) | 0.17 ± 0.01 (88) | 0.48 ± 0.03 (42) | 101 |
| 34 | 1.29 ± 0.14 (46) | 1.01 ± 0.11 (51) | 0.66 ± 0.08 (63) | 0.22 ± 0.03 (84) | 0.66 ± 0.04 (20) | 97 |
| 35 | 1.51 ± 0.12 (37) | 1.19 ± 0.10 (42) | 0.85 ± 0.09 (53) | 0.47 ± 0.04 (66) | 0.70 ± 0.06 (16) | 76 |
| 36 | 1.11 ± 0.08 (54) | 0.94 ± 0.09 (54) | 0.81 ± 0.05 (55) | 0.22 ± 0.02 (84) | 0.60 ± 0.06 (28) | 97 |

TABLE 7-continued

| 37 | 0.95 ± 0.11 (61) | 0.79 ± 0.13 (62) | 0.46 ± 0.09 (74) | 0.06 ± 0.01 (96) | 0.59 ± 0.07 (29) | 110 |
|---|---|---|---|---|---|---|
| 38 | 0.74 ± 0.09 (69) | 0.60 ± 0.06 (71) | 0.42 ± 0.03 (77) | 0.16 ± 0.04 (89) | 0.23 ± 0.01 (72) | 102 |
| 39 | 0.86 ± 0.13 (64) | 0.62 ± 0.11 (70) | 0.49 ± 0.07 (73) | 0.04 ± 0.01 (97) | 0.53 ± 0.03 (36) | 111 |
| 42 | 0.99 ± 0.09 (59) | 0.95 ± 0.09 (54) | 0.62 ± 0.08 (65) | 0.03 ± 0.01 (98) | 0.54 ± 0.01 (35) | 113 |
| 41 | 0.97 ± 0.10 (60) | 1.04 ± 0.12 (50) | 0.93 ± 0.11 (48) | 0.75 ± 0.09 (46) | 0.71 ± 0.11 (14) | 53 |
| 42 | 1.61 ± 0.07 (33) | 1.31 ± 0.09 (36) | 0.94 ± 0.08 (47) | 0.34 ± 0.09 (76) | 0.58 ± 0.08 (30) | 87 |
| 43 | 1.29 ± 0.19 (46) | 1.14 ± 0.11 (45) | 1.02 ± 0.14 (43) | 0.81 ± 0.11 (42) | 0.57 ± 0.09 (31) | 48 |

$^a$Potency was expressed as % inhibition of edema for the tested compounds relative to % inhibition of edema for indomethacin "reference standard" at 4 h effect.

Example 3: Ulcerogenic Liability of Curcumin Conjugates

Materials and Methods

Ulcerogenic liability for the most promising anti-inflammatory active agents was evaluated. The ulcerogenic liability was investigated in albino mice using the standard method. Animals of either sex (pregnant females were excluded) weighing 20-25 g were divided into 8 groups of 6 animals each. The animals were fasted 18 h before drug administration. Tested compounds were suspended in saline solution (0.9%) by the aid of a few drops of Tween 80 and were administered orally for three successive days to fasted rats at a dose of 10 mg/kg (animal body weight) indomethacin mol equivalent. The control group animals were given saline solution only with few drops of Tween 80. The animals were sacrificed by cervical dislocation and the stomach was removed, opened along the greater curvature and rinsed with saline. The gastric mucosa was examined with a magnifying lens (10×) for the presence of lesions and erosions. The ulcer index was calculated and the degree of ulcerogenic effect was expressed in terms of:

1. percentage incidence of ulcer divided by 10;
2. average number of ulcers per stomach; and
3. average severity of ulcers;

The ulcer index is the value that resulted from the sum of the above three values.

Results

Table 8 below shows the results of the ulcerogenic liability of the most promising anti-inflammatory active agents. The results revealed that all of the synthesized curcumin conjugates were less ulcerogenic (ulcer indexes=0-4.67) than indomethacin (ulcer index=13.67) and nearly all of the synthesized curcumin conjugates (except Cbz-DL-Ala-Cur) were less ulcerogenic than ibuprofen (ulcer index=4.33). In addition, several of the synthesized curcumin conjugates (ulcer index=0) were comparable to the control (ulcer index=0).

TABLE 8

Ulcerogenic liability of the most promising anti-inflammatory active agents.

| Entry | Compd. | Number of animals with ulcer | % Incidence of ulcer divided by 10 | Average of ulcer number | Average severity of ulcer | Ulcer index |
|---|---|---|---|---|---|---|
| 1 | Control | 0/6 | 0 | 0 | 0 | 0 |
| 2 | Indomethacin | 6/6 | 10 | 2 | 1.67 | 13.67 |
| 3 | Ibuprofen | 2/6 | 3.33 | 0.33 | 0.67 | 4.33 |
| 4 | Curcumin | 2/6 | 3.33 | 0.33 | 0.33 | 3.99 |
| 5 | Cbz-DL-Ala-Cur | 2/6 | 3.33 | 0.67 | 0.67 | 4.67 |
| 6 | Cbz-Met-Cur | 2/6 | 3.33 | 0.33 | 0.33 | 3.99 |
| 7 | Fmoc-Gly-Cur | 0/6 | 0 | 0 | 0 | 0 |
| 8 | Fmoc-Met-Cur | 0/6 | 0 | 0 | 0 | 0 |
| 9 | Z-D-Ala-Cur | 0/6 | 0 | 0 | 0 | 0 |
| 10 | Z-D-Met-Cur | 0/6 | 0 | 0 | 0 | 0 |
| 11 | Boc-L-Met-Cur | 0/6 | 0 | 0 | 0 | 0 |
| 12 | Boc-D-Met-Cur | 0/6 | 0 | 0 | 0 | 0 |
| 13 | HCl-Gly-Cur | 0/6 | 0 | 0 | 0 | 0 |
| 14 | HCl-D-Ala-Cur | 0/6 | 0 | 0 | 0 | 0 |
| 15 | HCl-β-Ala-Cur | 0/6 | 0 | 0 | 0 | 0 |
| 16 | HCl-L-Met-Cur | 0/6 | 0 | 0 | 0 | 0 |
| 17 | HCl-D-Met-Cur | 0/6 | 0 | 0 | 0 | 0 |

Example 4: Immunomodulatory Effects of Curcumin Conjugates

Materials and Methods

Immunomodulatory effects of the synthesized curcumin conjugates on the proliferative response of PHA-stimulated splenocytes were evaluated. The effect of curcumin and its amino acid conjugates on splenocyte viability and proliferation in response to a T cell miotgen (Phytohaemagglutinin; PHA) was evaluated using the MTT assay. Freshly prepared splenocytes ($1 \times 10^6$ cells/200 µl/well) were cultured in a 96-well U-bottom microtiter plate (Nunc) in complete medium. Cells were treated with tested compounds at a final concentration of 10 µM, vehicle (DMSO) or left untreated in triplicate then incubated at 37° C. and 5% $CO_2$. When testing the immunoregulatory effects of the compounds on splenocyte stimulation, PHA (5 µg/ml) was added to the culture media to induce T cell proliferation. The proliferative response to PHA+vehicle and vehicle alone served as controls. After 72 hr, media were removed after pelleting the cells by centrifugation and MTT salt solution (5 mg/ml) was added into each well then incubated at 37° C. for 4 h. Afterwards, formazan crystals were dissolved by adding 150 µl 10% sodium dodecyl sulfate (SDS). Absorbance was measured with a spectrophotometer at 570 nm and reference wavelength of 690 nm. The results of cell viability were expressed as the percentage of viable cells standard deviation using equation (3):

$$\% \text{ of viable cells} = \frac{\text{Optical density } (O.D.) \text{ of tested compound}}{O.D. \text{ of vehicle}} \times 100. \quad (3)$$

Splenocyte stimulation index was determined as the ratio of O.D. values in tested compounds versus vehicle control cultures.

Results

Table 9 below shows the results of the immunomodulatory effects of the synthesized curcumin conjugates on the proliferative response of PHA-stimulated splenocytes. Given the marginal cytotoxic activity of curcumin derivatives at 10 µM, a low concentration (5 µM) was used to evaluate the regulatory effect of the tested compounds on phytohaemagglutinin (PHA) induced proliferation of splenocytes as assessed by MTT assay. In the presence of PHA (T cell mitogen), splenocyte proliferation was markedly increased by 2.76 fold relative to untreated control cells which was further potentiated to 3.81 fold by exposure of splenocytes to compound Cbz-Phe-Cur. Some of the curcumin derivatives had negligible effects on splenocyte proliferation. However, some curcumin conjugates significantly suppressed mitogen-induced T cell proliferation.

Overall, the synthesized conjugates show significant antiproliferative activity that could possibly serve as immunosuppressant in immune-mediated disorders. Furthermore, conjugate Cbz-Phe-Cur enhances lymphocyte response to mitogen suggesting that this compound has potential therapeutic value as an immunostimulant. Additionally, the exhibited biological properties are correlated with the anti-inflammatory properties revealed through in-vivo acute carrageenan induced paw edema in rats.

TABLE 9

The immunomodulatory effect of curcumin derivatives on proliferative response of PHA-stimulated splenocytes.

| Entry | Compd. | Stimulation Index (average ± SD)* | Potency** (%) |
|---|---|---|---|
| 1 | Control | 1.00 ± 0.24 | — |
| 2 | PHA | 2.78 ± 0.28 | — |
| 3 | Cyclosporin A | 1.21 ± 0.13 | 100.26 |
| 4 | Curcumin | 1.52 ± 0.10 | 79.45 |
| 5 | Cbz-Gly-Cur | 2.64 ± 0.10 | 45.77 |
| 6 | Cbz-Ala-Cur | 2.70 ± 0.25 | 44.89 |
| 7 | Cbz-DL-Ala-Cur | 1.18 ± 0.09 | 102.70 |
| 8 | Cbz-Val-Cur | 2.87 ± 0.11 | 42.11 |
| 9 | Cbz-Leu-Cur | 2.83 ± 0.17 | 42.79 |
| 10 | Cbz-Met-Cur | 1.22 ± 0.29 | 99.31 |
| 11 | Cbz-Phe-Cur | 2.91 ± 0.13 | 41.53 |
| 12 | Cbz-Trp-Cur | 2.60 ± 0.12 | 46.48 |
| 13 | Fmoc-Gly-Cur | 1.76 ± 0.20 | 68.80 |
| 14 | Fmoc-Ala-Cur | 2.22 ± 0.41 | 54.40 |
| 15 | Fmoc-Val-Cur | 2.55 ± 0.13 | 47.53 |
| 16 | Fmoc-Leu-Cur | 2.16 ± 0.13 | 56.14 |
| 17 | Fmoc-Met-Cur | 1.07 ± 0.16 | 112.59 |
| 18 | Fmoc-Phe-Cur | 1.78 ± 0.10 | 68.14 |
| 19 | Z-D-Ala-Cur | 1.59 ± 0.14 | 76.01 |
| 20 | Z-D-Met-Cur | 1.37 ± 0.29 | 88.46 |
| 21 | Z-L-Gln-Cur | 2.37 ± 0.16 | 51.10 |
| 22 | Boc-Gly-Cur | 2.11 ± 0.16 | 57.37 |
| 23 | Boc-L-Phe-Cur | 2.56 ± 0.14 | 47.21 |
| 24 | Boc-L-Ala-Cur | 2.71 ± 0.28 | 44.61 |
| 25 | Boc-DL-Ala-Cur | 1.78 ± 0.07 | 67.92 |

TABLE 9-continued

The immunomodulatory effect of curcumin derivatives on proliferative response of PHA-stimulated splenocytes.

| Entry | Compd. | Stimulation Index (average ± SD)* | Potency** (%) |
|---|---|---|---|
| 26 | Boc-D-Ala-Cur | 2.07 ± 0.12 | 58.32 |
| 27 | Boc-β-Ala-Cur | 1.70 ± 0.24 | 71.13 |
| 28 | Boc-L-Met-Cur | 1.37 ± 0.10 | 88.46 |
| 29 | Boc-D-Met-Cur | 2.53 ± 0.08 | 47.74 |
| 30 | Boc-L-Val-Cur | 1.84 ± 0.06 | 65.59 |
| 31 | Boc-L-Ile-Cur | 2.07 ± 0.10 | 58.32 |
| 32 | Boc-L-Gln-Cur | 2.14 ± 0.23 | 56.60 |
| 33 | HCl-Gly-Cur | 0.99 ± 0.16 | 122.41 |
| 34 | HCl-L-Phe-Cur | 1.41 ± 0.31 | 85.59 |
| 35 | HCl-L-Ala-Cur | 1.14 ± 0.18 | 105.80 |
| 36 | HCl-DL-Ala-Cur | 1.91 ± 0.15 | 63.23 |
| 37 | HCl-D-Ala-Cur | 1.35 ± 0.07 | 89.59 |
| 38 | HCl-β-Ala-Cur | 1.39 ± 0.98 | 87.36 |
| 39 | HCl-L-Met-Cur | 1.49 ± 0.06 | 81.29 |
| 40 | HCl-D-Met-Cur | 1.01 ± 0.15 | 120.31 |
| 41 | HCl-L-Val-Cur | 2.05 ± 0.15 | 58.97 |
| 42 | HCl-L-Ile-Cur | 1.59 ± 0.17 | 76.01 |
| 43 | HCl-L-Gln-Cur | 2.22 ± 0.20 | 54.54 |

*Average of triplicate experiments ± standard deviation (SD)
**Potency was expressed as % inhibition of stimulation index for the tested compounds relative to % inhibition of stimulation index for indomethacin "reference standard".

Example 5: Effects of Curcumin Conjugates on Production of Nitric Oxide

Materials and Methods

The effects of the synthesized curcumin conjugates on the production of nitric oxide (µM) by lipopolysaccharide-stimulated peritoneal macrophages were evaluated.

Two milliliters of macrophage cells were seeded in 12-well tissue culture plates in nitrite-free medium supplemented with 0.1% bovine serum albumin and incubated at 37° C. LPS±epinephrine, norepinephrine, or dopamine at 5×106 M concentrations was added to some wells. The concentrations of LPS used ranged from 0.5 to 10 ng/ml. After incubation for 24 h, supernatants were collected for measuring nitric oxide (NO) by spectrophotometry. The production of NO was determined from the accumulation of nitrite ($NO_2$), the metabolic end product of NO metabolism, in the medium using the Greiss reagent. About equal volumes (100 µl) of sample and Greiss reagent (1:1 mixture of 1% sulfanilamide in 5% phosphoric acid, and 0.1% a-naphthylamine in distilled water) were mixed and incubated at room temperature for 15 min, and absorbance was measured at 532 nm on a spectrophotometer.

Results

Table 10 below shows the effects of the synthesized curcumin conjugates on the production of nitric oxide by lipopolysaccharide (LPS)-stimulated peritoneal macrophages. The results show that the synthesized curcumin conjugates inhibited the production of nitric oxide by peritoneal macrophages stimulated with LPS alone. As shown in Table 10, several of the curcumin conjugates including Cbz-DL-Ala-Cur, Cbz-Met-Cur, Fmoc-Met-Cur, Z-D-Met-Cur, Boc-L-Met-Cur, HCl-Gly-Cur, HCl-L-Phe-Cur, HCl-L-Ala-Cur, HCl-D-Ala-Cur, HCl-β-Ala-Cur, HCl-L-Met-Cur, and HCl-D-Met-Cur (potency=45.41%, 44.44%, 47.91%, 40.84%, 40.84%, 49.98%, 39.74%, 46.24%, 41.26%, 41.68%, 37.94%, 49.57%, respectively) demonstrated greater inhibition of nitric oxide production than curcumin (potency=37.11%).

TABLE 10

The effects of various curcumin derivatives on the production of nitric oxide (µM) by lipopolysaccharide-stimulated peritoneal macrophages.

| Entry | Compd. | Stimulation Index (average ± SD)* | Potency** (%) |
|---|---|---|---|
| 1 | LPS | 27.31 ± 2.56 | 0.00 |
| 2 | Curcumin | 17.18 ± 0.65 | 37.11 |
| 3 | Cbz-Gly-Cur | 24.55 ± 0.66 | 10.11 |
| 4 | Cbz-Ala-Cur | 24.89 ± 1.65 | 8.86 |
| 5 | Cbz-DL-Ala-Cur | 14.91 ± 0.62 | 45.41 |
| 6 | Cbz-Val-Cur | 25.76 ± 0.99 | 5.68 |
| 7 | Cbz-Leu-Cur | 26.06 ± 0.65 | 4.57 |
| 8 | Cbz-Met-Cur | 15.17 ± 2.30 | 44.44 |
| 9 | Cbz-Phe-Cur | 26.33 ± 0.52 | 3.60 |
| 10 | Cbz-Trp-Cur | 24.28 ± 0.82 | 11.08 |
| 11 | Fmoc-Gly-Cur | 18.73 ± 1.29 | 31.43 |
| 12 | Fmoc-Ala-Cur | 21.79 ± 2.71 | 20.22 |
| 13 | Fmoc-Val-Cur | 23.91 ± 0.87 | 12.46 |
| 14 | Fmoc-Leu-Cur | 21.34 ± 0.86 | 21.88 |
| 15 | Fmoc-Met-Cur | 14.23 ± 1.05 | 47.91 |
| 16 | Fmoc-Phe-Cur | 18.84 ± 0.69 | 31.01 |
| 17 | Z-D-Ala-Cur | 17.63 ± 0.92 | 35.45 |
| 18 | Z-D-Met-Cur | 16.16 ± 1.90 | 40.84 |
| 19 | Boc-Gly-Cur | 18.12 ± 1.41 | 33.65 |
| 20 | Boc-L-Ala-Cur | 21.30 ± 1.72 | 22.02 |
| 21 | Boc-DL-Ala-Cur | 18.88 ± 0.46 | 30.88 |
| 22 | Boc-D-Ala-Cur | 20.81 ± 0.82 | 23.82 |
| 23 | Boc-β-Ala-Cur | 18.35 ± 1.61 | 32.81 |
| 24 | Boc-L-Met-Cur | 16.16 ± 0.64 | 40.84 |
| 25 | Boc-L-Val-Cur | 19.29 ± 0.39 | 29.35 |
| 26 | Boc-L-Ile-Cur | 20.81 ± 0.68 | 23.82 |
| 27 | Boc-L-Gln-Cur | 21.22 ± 1.50 | 22.29 |
| 28 | HCl-Gly-Cur | 13.66 ± 1.05 | 49.98 |
| 29 | HCl-L-Phe-Cur | 16.46 ± 2.05 | 39.74 |
| 30 | HCl-L-Ala-Cur | 14.68 ± 1.20 | 46.24 |
| 31 | HCl-DL-Ala-Cur | 19.75 ± 0.97 | 27.69 |
| 32 | HCl-D-Ala-Cur | 16.04 ± 0.46 | 41.26 |
| 33 | HCl-β-Ala-Cur | 15.93 ± 0.29 | 41.68 |
| 34 | HCl-L-Met-Cur | 16.95 ± 0.40 | 37.94 |
| 35 | HCl-D-Met-Cur | 13.77 ± 0.96 | 49.57 |
| 36 | HCl-L-Val-Cur | 20.65 ± 0.99 | 24.37 |
| 37 | HCl-L-Ile-Cur | 17.63 ± 1.14 | 35.45 |
| 38 | HCl-L-Gln-Cur | 21.75 ± 1.31 | 20.35 |

*Average of triplicate experiments ± standard deviation (SD)
**% Inhibition of nitric oxide production for the tested compounds relative to lipopolysaccharide-stimulated macrophages.

Example 6: Antimicrobial Properties of Curcumin Conjugates

Materials and Methods

The antimicrobial properties of the synthesized curcumin conjugates were evaluated. The synthesized conjugates in addition to the parent and standards were screened for their antimicrobial properties against a variety of Gram-positive bacteria (*Staphylococcus aureus* ATCC25923 and *Streptococcus pyogenes* ATCC19615), Gram-negative bacteria (*Salmonella typhi* ATCC19430, *Pseudomonas aeruginosa* ATCC27853), and fungi *Candida albicans* by the agar dilution standard method. The tested compounds were dissolved in dimethylsulfoxide (DMSO). An inoculum of approximately $1.5 \times 10^8$ colony-forming units (CFU) per spot was applied to the surfaces of Mueller-Hinton agar plates containing graded concentrations of the respective compounds. The plates were incubated at 37° C. for 18 h. The spot with the lowest concentration of compound showing no growth was defined as the MIC (minimum inhibitory concentration). All the organisms used in this study were standard strains obtained from American Type Culture Collection (ATCC). All the MIC experiments were performed in duplicates (2 wells/per compound). No difference in the readings (duplicates) was observed. A negative control (DMSO) was carried out for each experiment. Table 11 shows the experimentally observed MIC values for all the tested compounds.

Results

Table 11 below shows the results of the antimicrobial tests. The results show that the synthesized curcumin conjugates demonstrated much lower minimum inhibitory concentrations (MICs) against the microorganisms, *Staphylococcus aureus, Streptococcus pyogenes, Salmonella Typhi, Pseudomonas aeruginosa,* and *Candida albicans,* than the Norfloxacin, Ciprofloxacin, and Amphotericin B antibiotics. For example, Norfloxacin and Ciprofloxacin demonstrated MICs of 1250 µg/mL against *Staphylococcus aureus,* while the synthesized curcumin conjugates showed MICs of 2.0 µg/mL or less against *Staphylococcus aureus.* Several of the synthesized curcumin conjugates showed MICs of 0.5 µg/mL or less against *Staphylococcus aureus.* In addition, several of the synthesized curcumin conjugates showed MICs of 1.0 µg/mL or less against *Streptococcus pyogenes, Salmonella Typhi, Pseudomonas aeruginosa,* and *Candida albicans.*

TABLE 11

Antimicrobial properties of curcumin conjugates.

Minimum inhibitory concentration (MIC), µg/mL (µM)

| Entry | Compd. | *Staphylococcus aureus* (ATCC#25923) | *Streptococcus pyogenes* (ATCC#19615) | *Salmonella Typhi* (ATCC#19430) | *Pseudomonas aeruginosa* (ATCC#27853) | *Candida albicans* (local isolate) |
|---|---|---|---|---|---|---|
| 1 | Curcumin | 0.125 (0.339) | 0.125 (0.339) | 0.125 (0.339) | 0.125 (0.339) | 0.125 (0.339) |
| 2 | Norfloxacin | 1250 (3914.446) | 625 (1957.223) | 2.4 (7.516) | 4.8 (15.031) | — |
| 3 | Ciprofloxacin | 1250 (3772.446) | 1250 (3772.446) | 2.4 (7.243) | 4.8 (14.486) | — |
| 4 | Amphotericin B | — | — | — | — | 0.39 (0.422) |
| 5 | Cbz-Gly-Cur | 0.125 (0.166) | 0.125 (0.166) | 0.5 (0.666) | 1.0 (1.332) | 0.5 (0.666) |
| 6 | Cbz-Ala-Cur | 0.25 (0.321) | 0.125 (0.161) | 0.5 (0.642) | 2.0 (2.568) | 2.0 (2.568) |
| 7 | Cbz-DL-Ala-Cur | 0.5 (0.642) | 0.125 (0.161) | 0.5 (0.642) | 0.25 (0.321) | 0.5 (0.642) |
| 8 | Cbz-Val-Cur | 0.125 (0.150) | 0.5 (0.599) | 0.125 (0.150) | 0.25 (0.299) | 1.0 (1.198) |
| 9 | Cbz-Leu-Cur | 0.125 (0.145) | 0.125 (0.145) | 0.25 (0.290) | 0.125 (0.145) | 0.5 (0.579) |
| 10 | Cbz-Met-Cur | 0.125 (0.139) | 0.125 (0.139) | 0.125 (0.139) | 0.125 (0.139) | 2.0 (2.225) |
| 11 | Cbz-Phe-Cur | 0.125 (0.134) | 0.125 (0.134) | 0.125 (0.134) | 0.25 (0.269) | 2.0 (2.148) |
| 12 | Cbz-Trp-Cur | 0.125 (0.124) | 0.5 (0.496) | 0.125 (0.124) | 0.25 (0.248) | 1.0 (0.991) |
| 13 | Fmoc-Gly-Cur | 1.0 (1.079) | 1.0 (1.079) | 1.0 (1.079) | 1.0 (1.079) | 2.0 (2.158) |
| 14 | Fmoc-Ala-Cur | 0.5 (0.524) | 0.5 (0.524) | 0.25 (0.262) | 0.25 (0.262) | 1.0 (1.047) |
| 15 | Fmoc-Val-Cur | 0.25 (0.247) | 0.5 (0.494) | 0.5 (0.494) | 0.5 (0.494) | 0.5 (0.494) |
| 16 | Fmoc-Leu-Cur | 0.25 (0.241) | 0.5 (0.481) | 0.5 (0.481) | 0.25 (0.241) | 0.5 (0.481) |

TABLE 11-continued

Antimicrobial properties of curcumin conjugates.

Minimum inhibitory concentration (MIC), µg/mL (µM)

| Entry | Compd. | Staphylococcus aureus (ATCC#25923) | Streptococcus pyogenes (ATCC#19615) | Salmonella Typhi (ATCC#19430) | Pseudomonas aeruginosa (ATCC#27853) | Candida albicans (local isolate) |
|---|---|---|---|---|---|---|
| 17 | Fmoc-Met-Cur | 0.25 (0.233) | 0.125 (0.116) | 2.0 (1.860) | 2.0 (1.860) | 0.5 (0.465) |
| 18 | Fmoc-Phe-Cur | 0.25 (0.226) | 0.125 (0.113) | 0.25 (0.226) | 2.0 (1.806) | 0.5 (0.452) |
| 19 | Z-D-Ala-Cur | 0.5 (0.642) | 0.125 (0.161) | 0.5 (0.642) | 1.0 (1.284) | 0.5 (0.642) |
| 20 | Z-D-Met-Cur | 0.125 (0.139) | 0.125 (0.139) | 0.5 (0.556) | 1.0 (1.112) | 0.125 (0.139) |
| 21 | Z-L-Gln-Cur | 0.5 (0.560) | 0.125 (0.140) | 0.5 (0.560) | 1.0 (1.120) | 0.5 (0.560) |
| 22 | Boc-Gly-Cur | 0.25 (0.366) | 1.0 (1.465) | 0.125 (0.183) | 0.25 (0.366) | 0.5 (0.732) |
| 23 | Boc-L-Phe-Cur | 0.25 (0.290) | 0.125 (0.145) | 0.25 (0.290) | 1.0 (1.159) | 1.0 (1.159) |
| 24 | Boc-L-Ala-Cur | 0.125 (0.176) | 0.25 (0.352) | 0.125 (0.176) | 1.0 (1.407) | 1.0 (1.407) |
| 25 | Boc-DL-Ala-Cur | 0.25 (0.352) | 0.125 (0.176) | 0.25 (0.352) | 0.25 (0.352) | 0.5 (0.703) |
| 26 | Boc-D-Ala-Cur | 0.125 (0.176) | 1.0 (1.407) | 0.25 (0.352) | 0.25 (0.352) | 0.5 (0.703) |
| 27 | Boc-β-Ala-Cur | 0.25 (0.352) | 0.25 (0.352) | 0.5 (0.703) | 0.25 (0.352) | 0.5 (0.703) |
| 28 | Boc-L-Met-Cur | 2.0 (2.407) | 2.0 (2.407) | 2.0 (2.407) | 1.0 (1.203) | 1.0 (1.203) |
| 29 | Boc-D-Met-Cur | 0.25 (0.301) | 0.125 (0.150) | 1.0 (1.203) | 0.25 (0.301) | 0.5 (0.602) |
| 30 | Boc-L-Val-Cur | 0.25 (0.326) | 2.0 (2.608) | 0.25 (0.326) | 2.0 (2.608) | 1.0 (1.304) |
| 31 | Boc-L-Ile-Cur | 0.125 (0.157) | 0.25 (0.314) | 0.125 (0.157) | 1.0 (1.258) | 2.0 (2.516) |
| 32 | Boc-L-Gln-Cur | 0.125 (0.152) | 0.25 (0.303) | 0.125 (0.152) | 1.0 (1.212) | 2.0 (2.425) |
| 33 | HCl-Gly-Cur | 0.5 (0.900) | 0.25 (0.450) | 0.25 (0.450) | 1.0 (1.800) | 1.0 (1.800) |
| 34 | HCl-L-Phe-Cur | 0.25 (0.340) | 0.5 (0.680) | 0.125 (0.170) | 0.5 (0.680) | 0.5 (0.680) |
| 35 | HCl-L-Ala-Cur | 0.5 (0.857) | 0.5 (0.857) | 0.5 (0.857) | 0.25 (0.428) | 0.5 (0.857) |
| 36 | HCl-DL-Ala-Cur | 0.125 (0.214) | 0.25 (0.428) | 0.25 (0.428) | 0.5 (0.857) | 1.0 (1.714) |
| 37 | HCl-D-Ala-Cur | 0.125 (0.214) | 0.25 (0.428) | 0.25 (0.428) | 1.0 (1.714) | 0.125 (0.214) |
| 38 | HCl-β-Ala-Cur | 1.0 (1.714) | 1.0 (1.714) | 1.0 (1.714) | 1.0 (1.714) | 0.5 (0.857) |
| 39 | HCl-L-Met-Cur | 0.25 (0.355) | 0.5 (0.711) | 0.125 (0.178) | 0.5 (0.711) | 0.5 (0.711) |
| 40 | HCl-D-Met-Cur | 0.125 (0.178) | 0.25 (0.355) | 0.25 (0.355) | 1.0 (1.421) | 1.0 (1.421) |
| 41 | HCl-L-Val-Cur | 0.25 (0.391) | 0.125 (0.195) | 0.125 (0.195) | 0.25 (0.391) | 0.125 (0.195) |
| 42 | HCl-L-Ile-Cur | 0.25 (0.374) | 0.5 (0.749) | 0.125 (0.187) | 0.25 (0.374) | 0.125 (0.187) |
| 43 | HCl-L-Gln-Cur | 0.25 (0.358) | 0.5 (0.717) | 0.125 (0.179) | 0.5 (0.717) | 0.125 (0.179) |

Example 7: Anti-Tumor Properties of Curcumin Conjugates

Materials and Methods

Anti-tumor properties of curcumin conjugates were evaluated. The synthesized curcumin-amino acid conjugates and curcumin itself were screened for their antitumor properties against human tumor cell lines utilizing HepG2 (hepatocellular), MCF7 (breast), and HCT116 (colon) carcinoma cell lines by the standard mitochondrial dependent reduction of yellow MTT [3-(4,5-dimethylthiazol-2-yl)-2,5-diphenyl-tetrazolium bromide] to purple formazan technique. Cancer cells were obtained from the Egyptian Company for Production of Vaccines, Sera and Drugs (VACSERA), Cairo, Egypt. Media, chemicals and supplies for the bio-assay were obtained from Biowest, Gibco and Lonza Companies. Cells were suspended in RPMI-1640 medium for HepG2, DMEMF12 for MCF-7, and DMEM for HCT116 in addition to 1% antibiotic-antimycotic mixture (10 000 mg ml$^{-1}$ potassium penicillin, 10 000 mg streptomycin sulfate and 25 mg ml$^{-1}$ amphotericin B), 10% fetal bovine serum and 1% L-glutamine at 37° C., under 5% $CO_2$ and 95% humidity. Cells were seeded at a concentration of 10×10$^3$ cells per well in fresh complete growth medium in 96-well tissue culture microtiter plates for 24 h. Media was aspirated, 180 µL fresh medium (without serum) were added and cells were incubated with different concentrations of sample to give a final concentration of 100 µM. 0.5% DMSO was used as a negative control and doxorubicin was used as a positive control (standard reference). Triplicate wells were prepared for each individual tested compound/dose. After 72 h of incubation, the medium was aspirated, 40 µL MTT salt (2.5 mg ml$^1$) were added to each well and incubated for an additional 4 h at 37° C. To stop the reaction and dissolve the formed crystals, 200 µL of 10% sodium dodecyl sulfate (SDS) in deionized water were added to each well and incubated overnight at 37° C. The absorbance was then measured at 595 nm with a reference wavelength of 620 nm. Data were collected as mean values for experiments performed in triplicates for each compound which had been measured by MTT assay. Control experiments did not exhibit significant change compared to the DMSO vehicle.

For compounds exhibiting inhibitory properties against the tested cell line higher than 50% at the initial concentration utilized (100 µM), serial dilutions were conducted (100, 50, 25, 12.5 µM) utilizing the same methodology mentioned for determining the $IC_{50}$ (concentration required to produce 50% inhibition of cell growth compared to the control experiment). The percentage of cell survival was calculated according to equation (4):

$$\text{Surviving fraction} = \frac{\text{Optical density (O.D.) of treated cells}}{\text{O.D. of control cells}} \quad (4)$$

The $IC_{50}$ was determined using Graph-Pad PRISM version-5 software. Statistical calculations for determination of the mean and standard deviation (SD) values were determined by SPSS 16 software.

Results

Table 12 below shows anti-tumor properties of synthesized curcumin conjugates at a dose of 100 µM against various carcinoma cell lines, specifically, HepG2 (liver), MCF7 (breast), and HCT116 (colon) carcinoma cell lines. Anti-tumor properties of curcumin derivatives were investigated utilizing HepG2 (hepatocellular), MCF7 (breast) and HCT116 (colon) carcinoma cell lines by the standard mitochondrial dependent reduction of yellow MTT [3-(4,5-dimethylthiazol-2-yl)-2,5-diphenyl-tetrazolium bromide] to purple formazan technique. From the results obtained, it has been shown that, the antitumor properties of the synthesized curcumin-amino acid conjugates were drastically reduced relative to the starting agent, curcumin [$IC_{50}$ of curcumin=38.00, 16.00, 38.25 µM, are promising properties compared with doxorubicin (DNA intercalating agent) of $IC_{50}$=34.20, 20.90, 7.17 µM against HepG2, MCF7 and HCT116 carcinoma cell lines, respectively)]. This observation can be attributed to the low solubility in aqueous media of the tested conjugates possessing amino acids with protecting groups.

TABLE 12

Anti-tumor properties of the tested compounds at a dose of 100 µM against HepG2 (liver), MCF7 (breast) and HCT116 (colon) carcinoma cell lines.

| | | Percentage growth of tumor cell lines treated with the tested compounds (±SD) | | |
|---|---|---|---|---|
| Entry | Compd. | HepG2 | MCF7 | HCT116 |
| 1 | Curcumin | 0.4 ± 0.0 | 4.6 ± 0.2 | 2.4 ± 3.4 |
| 2 | Cbz-Gly-Cur | 79.8 ± 8.8 | 60.0 ± 2.7 | 88.1 ± 2.6 |
| 3 | Cbz-Ala-Cur | 82.3 ± 4.2 | 70.0 ± 4.1 | 86.6 ± 6.2 |
| 4 | Cbz-DL-Ala-Cur | 82.9 ± 4.1 | 62.7 ± 4.7 | 92.0 ± 2.1 |
| 5 | Cbz-Val-Cur | 92.4 ± 2.8 | 85.0 ± 0.0 | 111.7 ± 7.9 |
| 6 | Cbz-Leu-Cur | 85.1 ± 5.7 | 85.7 ± 1.2 | 94.7 ± 5.8 |
| 7 | Cbz-Met-Cur | 85.4 ± 2.4 | 71.0 ± 0.0 | 85.6 ± 2.4 |
| 8 | Cbz-Phe-Cur | 99.6 ± 8.7 | 69.3 ± 3.0 | 96.4 ± 4.0 |
| 9 | Cbz-Trp-Cur | 97.6 ± 6.8 | 79.5 ± 0.6 | 100.5 ± 7.0 |
| 10 | Fmoc-Gly-Cur | 82.1 ± 7.0 | 87.0 ± 1.5 | 95.8 ± 6.7 |
| 11 | Fmoc-Ala-Cur | 78.3 ± 5.1 | 73.6 ± 2.2 | 96.9 ± 3.2 |
| 12 | Fmoc-Val-Cur | 116.2 ± 3.3 | 83.2 ± 0.8 | 81.8 ± 5.8 |
| 13 | Fmoc-Leu-Cur | 103.2 ± 2.6 | 83.0 ± 1.1 | 99.5 ± 3.8 |
| 14 | Fmoc-Met-Cur | 92.4 ± 5.1 | 88.9 ± 5.0 | 96.4 ± 1.4 |
| 15 | Fmoc-Phe-Cur | 108.5 ± 3.6 | 84.7 ± 3.6 | 110.2 ± 7.3 |

TABLE 13

Anti-tumor properties of the tested compounds at a dose of 100 µM against HCT116 (colon), A-549 (lung), MCF7 (breast), PC3 (prostate), and HepG2 (liver) carcinoma cell lines.

| | | $IC_{50}{}^a$ (µM) | | | | |
|---|---|---|---|---|---|---|
| Entry | Compd. | HCT116 (colon) | A-549 (lung) | MCF7 (breast) | PC3 (prostate) | HepG2 (liver) |
| 1 | Z-D-Ala-Cur | >100.00 | >100.00 | 72.98 | >100.00 | >100.00 |
| 2 | Z-D-Met-Cur | >100.00 | >100.00 | >100.00 | >100.00 | >100.00 |
| 3 | Z-L-Gln-Cur | >100.00 | 46.09 | 10.21 | 90.65 | >100.00 |
| 4 | Boc-Gly-Cur | >100.00 | 80.87 | 17.23 | >100.00 | >100.00 |
| 5 | Boc-L-Phe-Cur | >100.00 | >100.00 | >100.00 | >100.00 | >100.00 |
| 6 | Boc-L-Ala-Cur | >100.00 | >100.00 | 25.11 | >100.00 | >100.00 |
| 7 | Boc-DL-Ala-Cur | >100.00 | 73.91 | 34.78 | >100.00 | >100.00 |
| 8 | Boc-D-Ala-Cur | >100.00 | 85.43 | 29.15 | >100.00 | >100.00 |
| 9 | Boc-β-Ala-Cur | >100.00 | >100.00 | 13.19 | >100.00 | >100.00 |
| 10 | Boc-L-Met-Cur | >100.00 | >100.00 | 36.30 | >100.00 | >100.00 |
| 11 | Boc-D-Met-Cur | >100.00 | >100.00 | 22.34 | >100.00 | >100.00 |
| 12 | Boc-L-Val-Cur | >100.00 | >100.00 | 100.00 | >100.00 | >100.00 |
| 13 | Boc-L-Ile-Cur | >100.00 | >100.00 | 49.57 | >100.00 | >100.00 |
| 14 | Boc-L-Gln-Cur | >100.00 | 30.87 | 8.48 | 39.13 | 70.64 |
| 15 | HCl-Gly-Cur | 36.17 | 18.91 | 9.15 | 38.70 | 39.79 |
| 16 | HCl-L-Phe-Cur | 65.63 | 33.48 | 11.52 | 74.35 | 56.17 |
| 17 | HCl-L-Ala-Cur | 38.75 | 21.74 | 10.65 | 31.52 | 33.83 |
| 18 | HCl-DL-Ala-Cur | 66.88 | 22.17 | 9.79 | 21.74 | 36.81 |
| 19 | HCl-D-Ala-Cur | 39.17 | 30.87 | 10.43 | 30.65 | 34.26 |
| 20 | HCl-β-Ala-Cur | 42.29 | 32.38 | 9.36 | 30.22 | 36.38 |
| 21 | HCl-L-Met-Cur | 61.88 | 32.83 | 11.30 | 42.61 | 39.79 |
| 22 | HCl-D-Met-Cur | 46.67 | 20.00 | 10.21 | 41.52 | 43.62 |
| 23 | HCl-L-Val-Cur | 66.46 | 20.43 | 10.43 | 34.57 | 39.15 |
| 24 | HCl-L-Ile-Cur | 36.67 | 20.85 | 10.21 | 34.35 | 38.94 |
| 25 | HCl-L-Gln-Cur | 41.04 | 21.06 | 9.15 | 34.35 | 39.15 |

$^a IC_{50}$ is the concentration required to produce 50% inhibition of cell growth compared to the negative control.

Additionally, Table 13 below shows anti-tumor properties of synthesized curcumin conjugates at a dose of 100 µM against HCT116 (colon), A-549 (lung), MCF7 (breast), PC3 (prostate), and HepG2 (liver) carcinoma cell lines. As can be seen from Table 13, the HCl curcumin conjugates (i.e., entry nos. 15-25) showed superior growth-inhibitory effects on the various carcinoma cell lines. That is, the HCl curcumin conjugates require lower concentrations for inhibiting cell growth when compared to other curcumin conjugates.

Example 8: Effects of Curcumin Conjugates on Doxorubicin Induced Cytotoxicity

Materials and Methods

The effects of curcumin conjugates on doxorubicin induced cytotoxicity were evaluated. In order to further examine whether curcumin derivatives can enhance conventional chemotherapeutic agents, MCF-7 cells were treated with 100 µM curcumin derivatives alone or in combination with 10 µM doxorubicin (DOX) for 48 hr. Control cultures received only medium, vehicle (DMSO), or vehicle+DOX. The percentage of viable cells was determined by MTT assay according to equation (5):

$$\text{Percentage of viable cells} = \frac{O.D. \text{ of tested compound} + DOX}{O.D. \text{ of tested compound}} \times 100 \quad (5)$$

Results

Table 14 shows the results of the effects of curcumin conjugates on doxorubicin induced cytotoxicity. To evaluate the effect of curcumin derivatives on enhancing DOX cytotoxicity, the effect of 100 μM curcumin derivatives alone and in combination with 10 μM DOX was studied on MCF7 cell line. After 48 hr exposure, curcumin derivatives alone had minimal effect on cell viability (less than 5%) whereas, treatment of cells with vehicle+DOX reduced the cell viability to 44.79%. The cytotoxic effect of DOX was only enhanced when simultaneously combined with Fmoc-Gly-Cur, Fmoc-Ala-Cur and Fmoc-Val-Cur resulting in a significant reduction of the percentage of viable cells to 30.35%, 37.5% and 25.15%, respectively, while the other derivatives had marginal impact on the antitumor activity of DOX.

TABLE 14

Effect of curcumin conjugates on doxorubicin induced cytotoxicity.

| | | Percentage of viable cells MCF-7 (average ± SD)* | |
|---|---|---|---|
| Entry | Compd. | 0 μM DOX | 10 μM DOX |
| 1 | DOX | 0 ± 0.00 | 50.15 ± 1.71 |
| 2 | Vehicle | 100.00 ± 1.78 | 44.79 ± 1.61 |
| 3 | Curcumin | 10.81 ± 4.70 | 3.16 ± 1.62 |
| 4 | Cbz-Gly-Cur | 97.37 ± 5.30 | 45.44 ± 1.88 |
| 5 | Cbz-Ala-Cur | 99.51 ± 4.47 | 46.65 ± 2.06 |
| 6 | Cbz-DL-Ala-Cur | 98.83 ± 4.55 | 45.70 ± 2.23 |
| 7 | Cbz-Val-Cur | 99.22 ± 2.15 | 49.68 ± 1.46 |
| 8 | Cbz-Leu-Cur | 98.15 ± 3.44 | 50.17 ± 4.94 |
| 9 | Cbz-Met-Cur | 96.30 ± 3.61 | 49.74 ± 0.33 |
| 10 | Cbz-Phe-Cur | 104.87 ± 4.50 | 43.40 ± 4.74 |
| 11 | Cbz-Trp-Cur | 98.25 ± 2.96 | 45.17 ± 4.04 |
| 12 | Fmoc-Gly-Cur | 98.44 ± 1.46 | 30.35 ± 1.32 |
| 13 | Fmoc-Ala-Cur | 99.22 ± 3.65 | 37.55 ± 2.72 |
| 14 | Fmoc-Val-Cur | 100.29 ± 1.95 | 25.15 ± 1.96 |
| 15 | Fmoc-Leu-Cur | 98.25 ± 2.98 | 41.16 ± 2.33 |
| 16 | Fmoc-Met-Cur | 99.32 ± 3.16 | 38.75 ± 1.65 |
| 17 | Fmoc-Phe-Cur | 98.35 ± 2.21 | 42.49 ± 2.71 |

*Average of triplicate experiments ± standard deviation (SD).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A curcumin conjugate of the general formula

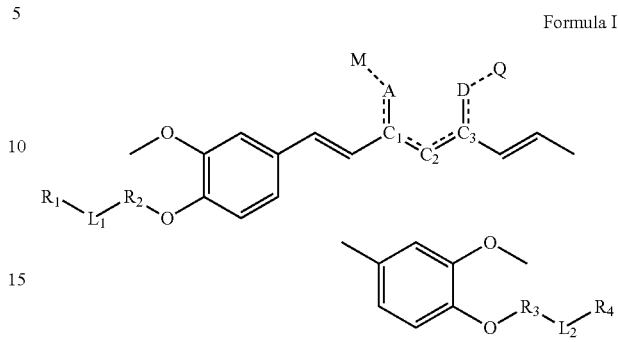

Formula I wherein the dotted lines between A and $C_1$, $C_1$ and $C_2$, $C_2$ and $C_3$ and $C_3$ and D indicate that a single or double bond may be present, as valence permits, wherein the dotted lines between A and M, and D and Q indicate that a single bond or no bond may be present, as valence permit, wherein $C_1$, $C_2$, and $C_3$ are carbon atoms, wherein A and D are oxygen atoms, wherein M and Q are independently absent, or hydrogen, as valence permits, wherein $R_2$ and $R_3$ can be one or more amino acids or salts thereof, nucleic acids, lipids, polysaccharides, polymers, substituted or unsubstituted alkyl groups, alkenyl groups, alkynyl groups, aryl groups, heteroaryl groups, or other organic groups containing between $C_1$ and $C_{10}$ carbon atoms, inclusive, wherein $R_1$ and $R_4$ can be carboxybenzyl (Cbz), or fluorenylmethyloxycarbonyl (FMOC), and wherein $L_1$ and $L_2$ can be independently absent, substituted or unsubstituted alkyl groups, alkenyl groups, alkynyl groups, aryl groups, heteroaryl groups, or other organic groups containing between $C_1$ and $C_{10}$ carbon atoms, inclusive or a combination thereof or pharmaceutically acceptable salt(s), polymorph(s), solvent(s), hydrate(s), crystal forms, and/or enantiomer(s) thereof.

2. The curcumin conjugate of claim 1, wherein M and Q are absent, the bond between A and $C_1$, and D and $C_3$ are double bonds, and the bonds between $C_1$ and $C_2$, and $C_2$ and $C_3$ are single bonds.

3. The curcumin conjugate of claim 1, wherein (i) the bond between $C_1$ and A is a double bond, M is absent, the bond between $C_1$ and $C_2$ is a single bond, the bond between $C_2$ and $C_3$ is a double bond, the bond between $C_3$ and D is a single bond, and Q is hydrogen, or (ii) the bond between $C_3$ and D is a double bond, Q is absent, the bond between $C_2$ and $C_3$ is a single bond, the bond between $C_1$ and $C_2$ is a double bond, the bond between $C_1$ and A is a single bond, and M is hydrogen.

4. The curcumin conjugate of claim 1, wherein $R_2$ and $R_3$ are each independently an amino acid and $R_1$ and $R_4$ are each independently carboxybenzyl (Cbz) or fluorenylmethyloxycarbonyl (FMOC).

5. The curcumin conjugate of claim 1, wherein the conjugate consists of the structure of any one of the following compounds:

2-4
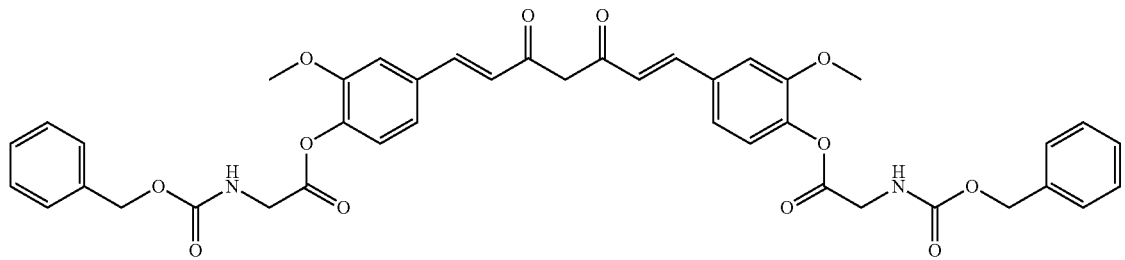
2-5
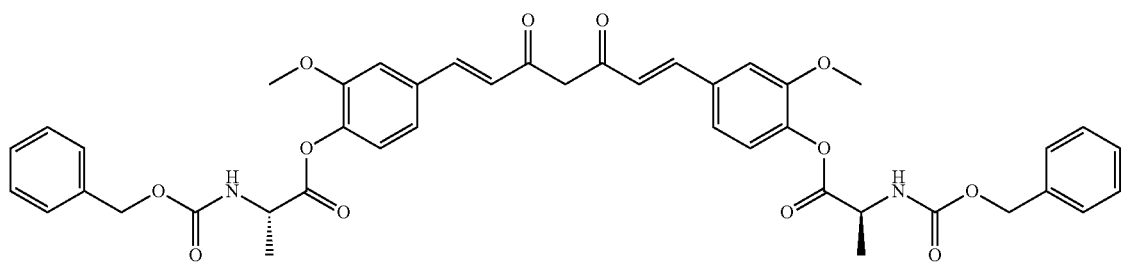
2-6
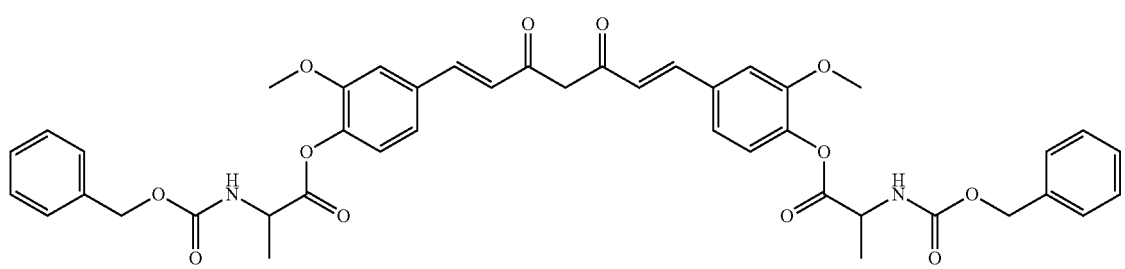
2-7
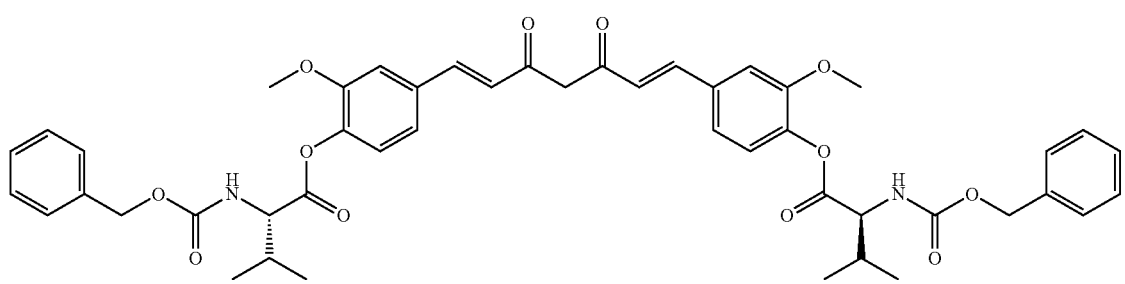
2-8
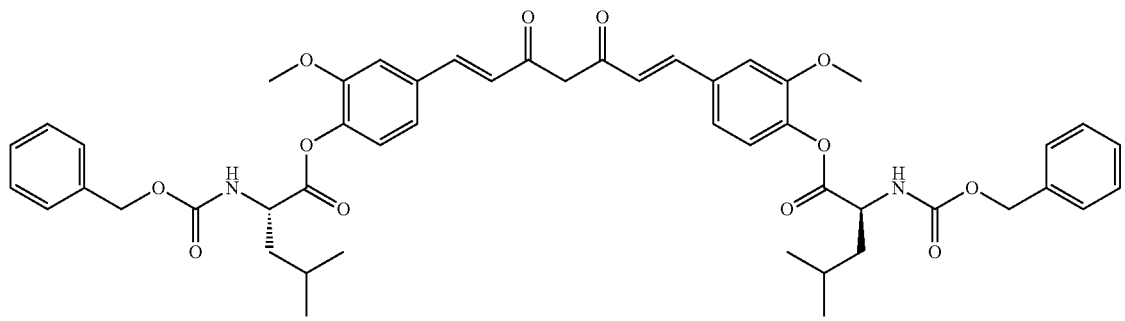

2-9
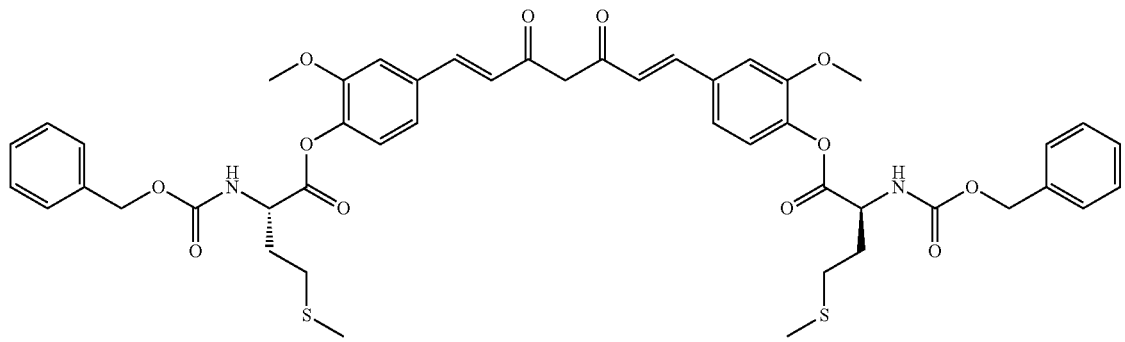
2-10
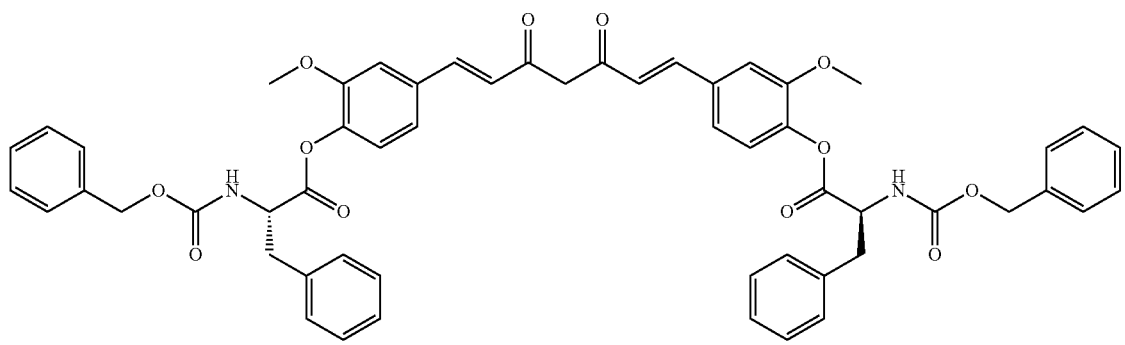
2-11
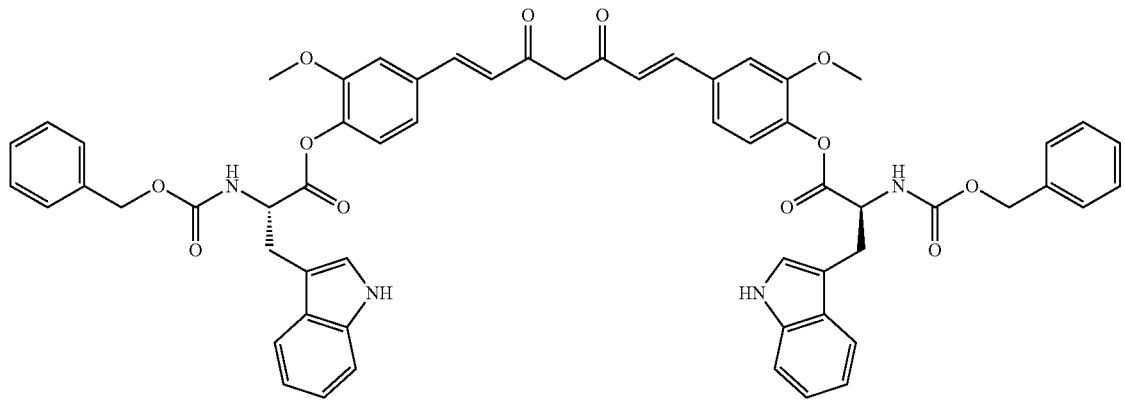
2-12
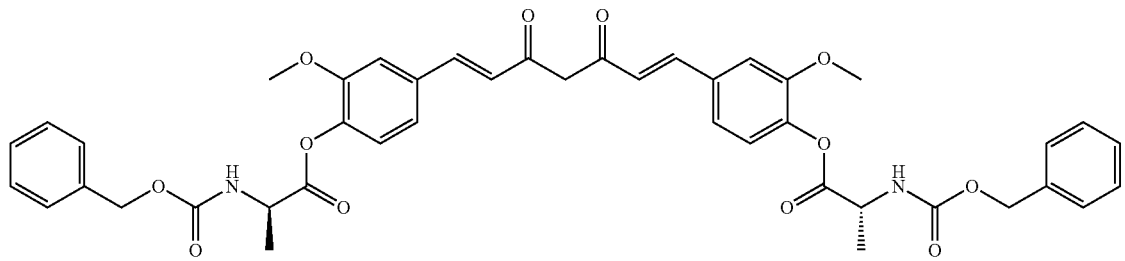

2-13
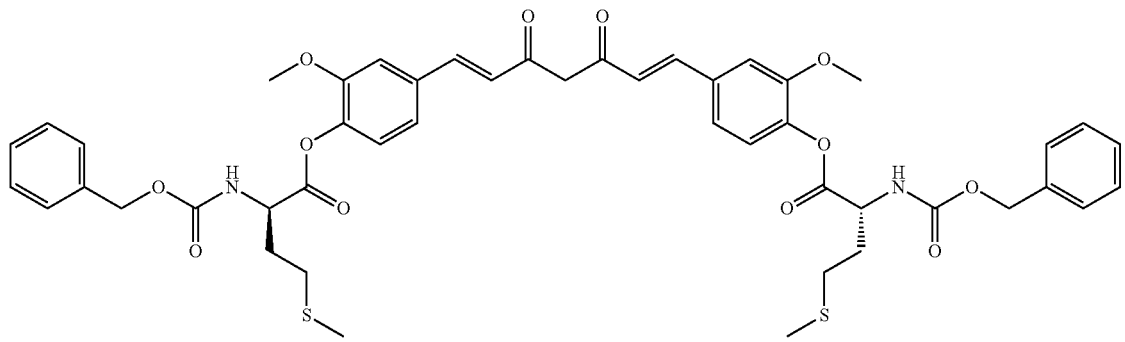
2-14
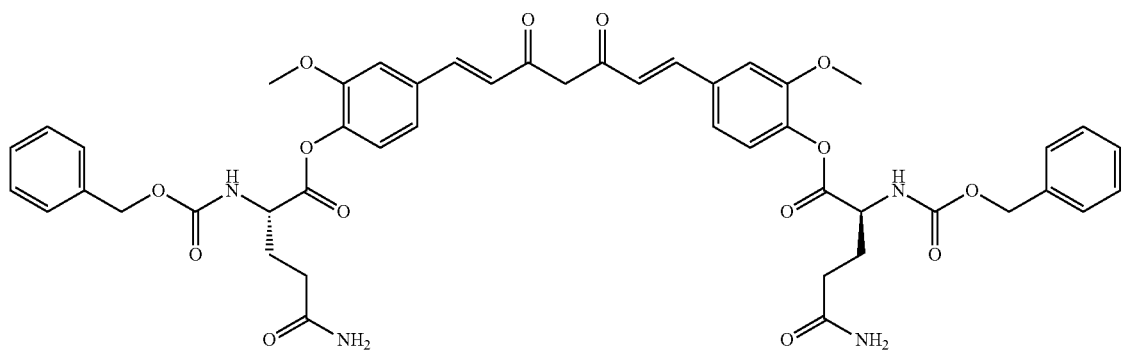
2-15
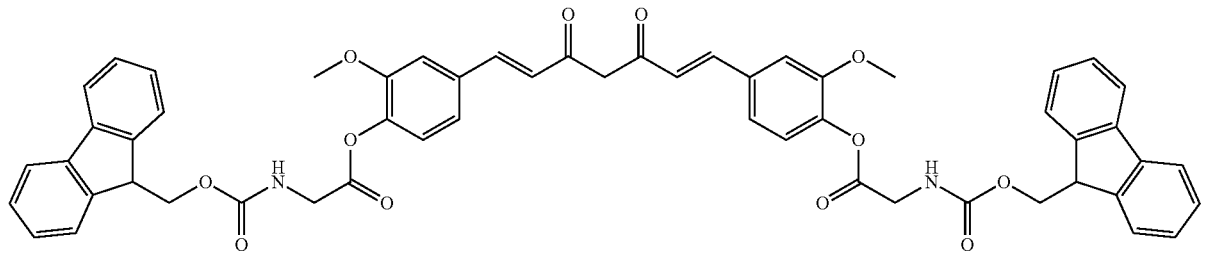
2-16
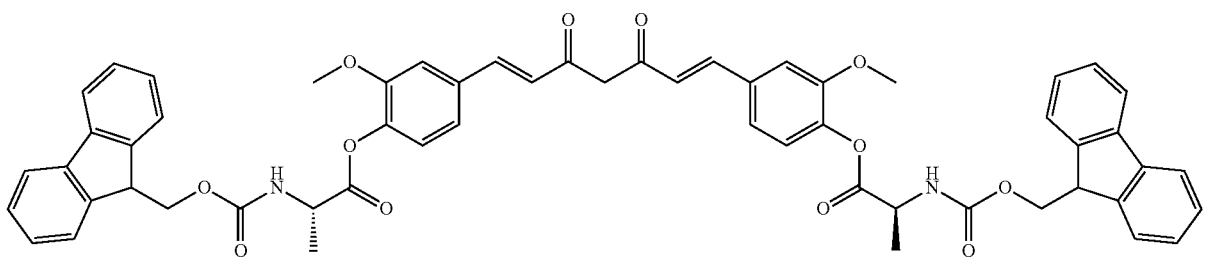
2-17
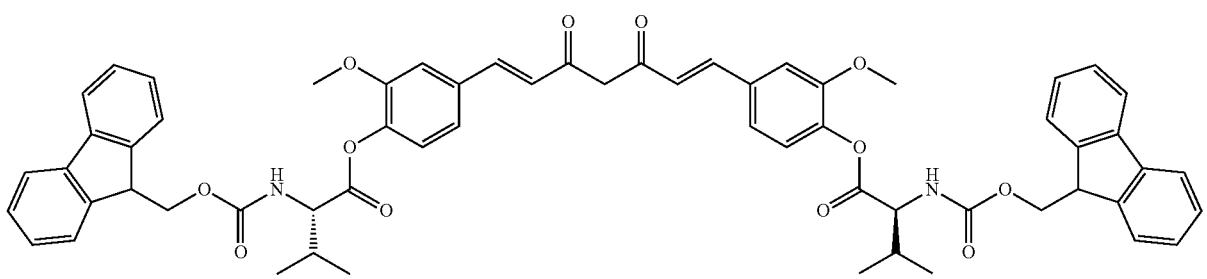

-continued 2-18
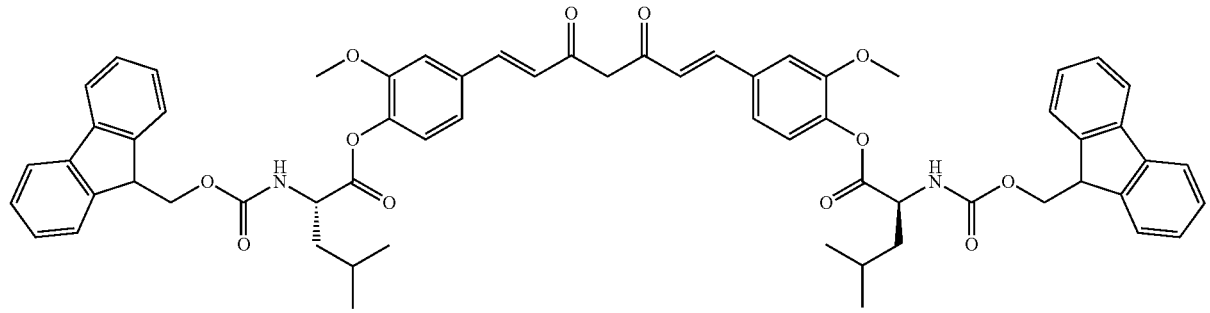

2-19
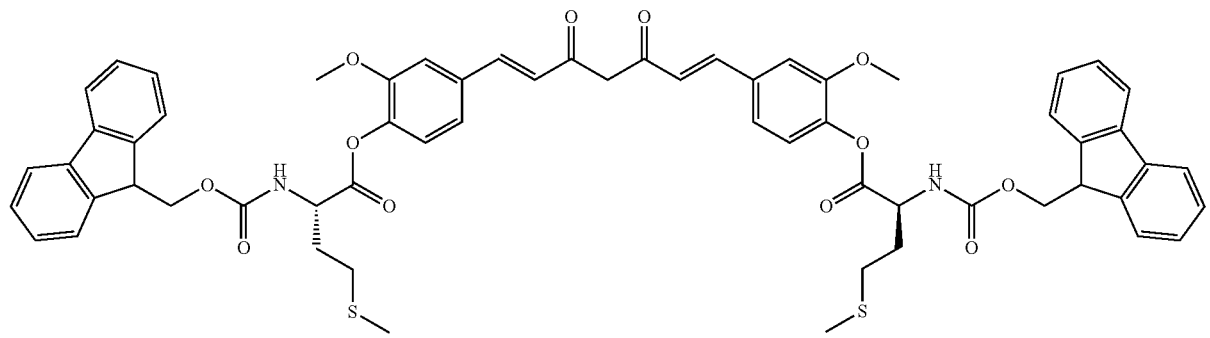

2-20
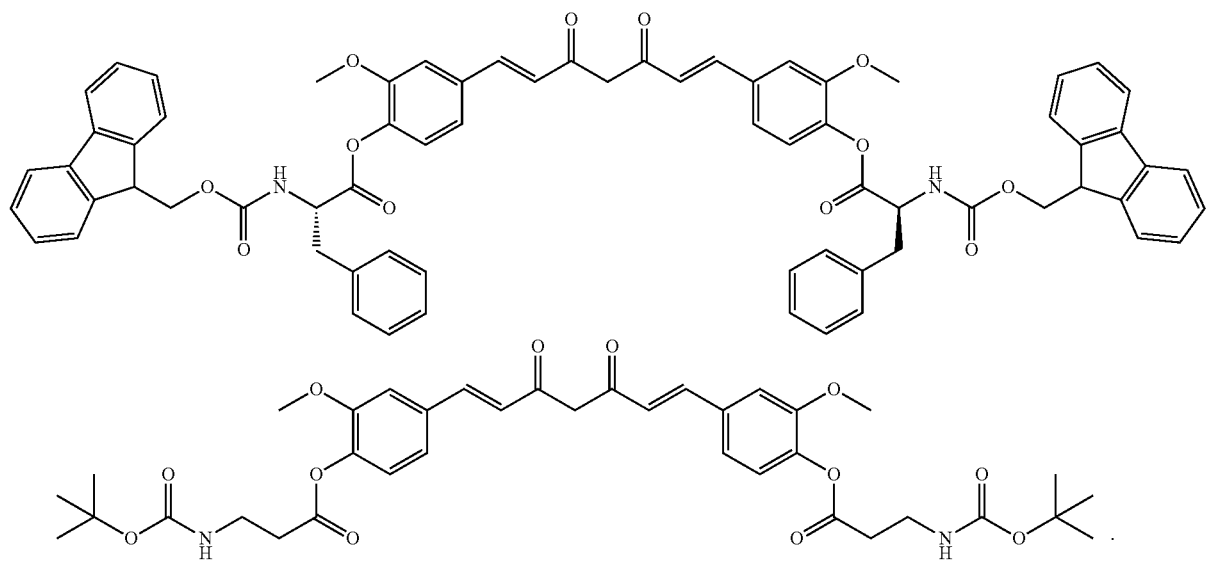

6. A pharmaceutical composition comprising an effective amount of at least one of the curcumin conjugates of claim 1.

7. The pharmaceutical composition of claim 6, further comprising a pharmaceutically acceptable excipient.

8. The pharmaceutical composition of claim 6, wherein the composition is formulated for oral delivery.

9. A pharmaceutical composition comprising a curcumin conjugate selected from the group consisting of ((1E,6E)-3,5-dioxohepta-1,6-diene-1,7-diyl)bis(2-methoxy-4,1-phenylene) bis(2-(((benzyloxy)carbonyl)amino)propanoate), ((1E,6E)-3,5-dioxohepta-1,6-diene-1,7-diyl)bis(2-methoxy-4,1-phenylene) (2S,2'S)-bis(2-(((benzyloxy)carbonyl)amino)-4-(methylthio)butanoate), ((1E,6E)-3,5-dioxohepta-1,6-diene-1,7-diyl)bis(2-methoxy-4,1-phenylene) bis(2-((((9H-fluoren-9-yl)methoxy)carbonyl)amino)acetate), ((1E,6E)-3,5-dioxohepta-1,6-diene-1,7-diyl)bis(2-methoxy-4,1-phenylene) (2S,2'S)-bis(2-(((((9H-fluoren-9-yl)methoxy)carbonyl)amino)-4-(methylthio)butanoate), ((1E,6E)-3,5-dioxohepta-1,6-diene-1,7-diyl)bis(2-methoxy-4,1-phenylene) (2R,2'R)-bis(2-(((benzyloxy)carbonyl)amino)propanoate), and ((1E,6E)-3,5-dioxohepta-1,6-diene-1,7-diyl)bis(2-methoxy-4,1-phenylene) (2R,2'R)-bis(2-(((benzyloxy)carbonyl)amino)-4-(methylthio)butanoate), or a combination thereof or pharmaceutically acceptable salt(s), polymorph(s), solvent(s), hydrate(s), crystal forms, and/or enantiomer(s) thereof.

10. The pharmaceutical composition of claim 6, wherein the composition is optically pure.

11. A method of treating cancer in a subject in need thereof comprising administering the subject an effective amount of the pharmaceutical composition of claim 6, wherein the cancer is breast cancer, colon cancer, liver cancer, lung cancer, or prostate cancer.

12. A method of treating an infection in a subject in need thereof comprising administering the subject an effective amount of the pharmaceutical composition of claim 6, wherein the infection is caused by a microbe selected from the group consisting of *Staphylococcus aureus, Streptococcus pyogenes, Salmonella Typhi, Pseudomonas aeruginosa,* and *Candida albicans*.

* * * * *